(12) United States Patent
Park et al.

(10) Patent No.: US 12,270,032 B2
(45) Date of Patent: *Apr. 8, 2025

(54) CODON-OPTIMIZED NUCLEOTIDE SEQUENCES ENCODING AN AP-1 TRANSCRIPTION FACTOR

(71) Applicant: Lyell Immunopharma, Inc., South San Francisco, CA (US)

(72) Inventors: Spencer Park, Seattle, WA (US); Queenie Vong, South San Francisco, CA (US); Blythe Sather, South San Francisco, CA (US); Byoung Ryu, South San Francisco, CA (US); Marc Lajoie, South San Francisco, CA (US)

(73) Assignee: LYELL IMMUNOPHARMA, INC., South San Francisco, CA (US)

( * ) Notice: Subject to any disclaimer, the term of this patent is extended or adjusted under 35 U.S.C. 154(b) by 182 days.

This patent is subject to a terminal disclaimer.

(21) Appl. No.: 17/679,977

(22) Filed: Feb. 24, 2022

(65) Prior Publication Data
US 2022/0307039 A1 Sep. 29, 2022

Related U.S. Application Data

(60) Provisional application No. 63/309,380, filed on Feb. 11, 2022, provisional application No. 63/263,231, filed on Oct. 28, 2021, provisional application No. 63/153,879, filed on Feb. 25, 2021.

(51) Int. Cl.
| | |
|---|---|
| C12N 15/67 | (2006.01) |
| A61K 39/00 | (2006.01) |
| A61P 35/00 | (2006.01) |
| C07K 14/725 | (2006.01) |
| C12N 5/078 | (2010.01) |
| C12N 15/861 | (2006.01) |

(52) U.S. Cl.
CPC .......... *C12N 15/67* (2013.01); *A61K 39/4611* (2023.05); *A61K 39/4631* (2023.05); *A61K 39/464402* (2023.05); *A61P 35/00* (2018.01); *C07K 14/7051* (2013.01); *C12N 5/0634* (2013.01); *C12N 15/8613* (2013.01); *C07K 2319/02* (2013.01); *C07K 2319/03* (2013.01); *C07K 2319/33* (2013.01)

(58) Field of Classification Search
CPC .. C12N 15/67; C12N 5/0634; C12N 15/8613; C12N 2740/16043; C12N 15/86; A61K 35/17; A61K 39/461; A61K 39/4631; A61P 35/00; C07K 14/7051; C07K 2319/02; C07K 2319/03; C07K 2319/33; C07K 2319/70; C07K 14/4702

See application file for complete search history.

(56) References Cited

U.S. PATENT DOCUMENTS

| | | | |
|---|---|---|---|
| 4,683,195 A | 7/1987 | Mullis et al. | |
| 10,822,413 B2 | 11/2020 | Liu et al. | |
| 2009/0226474 A1 | 9/2009 | Weidanz et al. | |
| 2014/0141067 A1 | 5/2014 | Bancel et al. | |
| 2016/0331844 A1* | 11/2016 | Fotin-Mleczek | .... A61K 48/005 |
| 2019/0092876 A1 | 3/2019 | Banham et al. | |
| 2019/0183932 A1 | 6/2019 | Mackall et al. | |
| 2019/0276801 A1 | 9/2019 | Jensen | |
| 2020/0030379 A1 | 1/2020 | Pule et al. | |
| 2020/0172879 A1 | 6/2020 | Suri et al. | |
| 2021/0299223 A1 | 9/2021 | Dipersio et al. | |
| 2023/0022654 A1 | 1/2023 | Park et al. | |

FOREIGN PATENT DOCUMENTS

| | | |
|---|---|---|
| CN | 101851668 A | 10/2010 |
| CN | 106636210 B | 7/2019 |
| WO | WO-2020028400 A1 | 2/2020 |
| WO | WO-2020223625 A1 | 11/2020 |
| WO | WO-2022182890 A1 | 9/2022 |

OTHER PUBLICATIONS

Leppä, S., Bohmann, D. Diverse functions of JNK signaling and c-Jun in stress response and apoptosis. Oncogene 18, 6158-6162 (1999). https://doi.org/10.1038/sj.onc.1203173 (Year: 1999).*

Lynn, R.C., Weber, E.W., Sotillo, E. et al. c-Jun overexpression in CAR T cells induces exhaustion resistance. Nature 576, 293-300 (2019). https://doi.org/10.1038/s41586-019-1805-z (Year: 2019).*

Carl H. June et al. ,CAR T cell immunotherapy for human cancer. Science359,1361-1365(2018).DOI:10.1126/science.aar6711 (Year: 2018).*

Wang X. et al. A transgene-encoded cell surface polypeptide for selection, in vivo tracking, and ablation of engineered cells. Blood. Aug. 4, 2011;118(5):1255-63. doi:10.1182/blood-2011-02-337360. Epub Jun. 7, 2011. PMID: 21653320; PMCID: PMC3152493. (Year: 2011).*

Holly Ahern. Biochemical, Reagents Kits Offer Scientists Good Return On Investment. The Scientist. Jul. 23, 1995. (Year: 1995).*

(Continued)

*Primary Examiner* — Richard A Schnizer
*Assistant Examiner* — Amanda M Zahorik
(74) *Attorney, Agent, or Firm* — Sterne, Kessler, Goldstein & Fox P.L.L.C.

(57) ABSTRACT

Disclosed herein are polynucleotides comprising a nucleotide sequence encoding an AP-1 transcription factor (i.e., c-Jun). In some aspects, the nucleotide sequence is codon-optimized. In some aspects, the polynucleotides comprise one or more additional nucleotide sequences encoding a linker, signal peptide, antigen-binding domain, spacer, transmembrane domain, costimulatory domain, intracellular signaling domain, truncated EGFR, and combinations thereof. Also disclosed herein are cells, vectors, and pharmaceutical compositions comprising such polynucleotides. The use of such polynucleotides, cells, vectors, and pharmaceutical compositions to treat a disease or disorder (e.g., cancer) is also provided.

20 Claims, 7 Drawing Sheets
Specification includes a Sequence Listing.

(56) References Cited

OTHER PUBLICATIONS

NCBI Genbank Accession No. NM_002228.4 (Year: 2019).*
NCBI Genbank Accession No. AY890408 (Year: 2005).*
NCBI Genbank Accession No. AY893924.1 (Year: 2016).*
NCBI Reference Sequence: NC_000001.11 positions 58783070-58782078 (Year: 2014).*
Inouye S, Sahara-Miura Y, Sato J, Suzuki T. Codon optimization of genes for efficient protein expression in mammalian cells by selection of only preferred human codons. Protein Expr Purif. May 2015;109:47-54. doi: 10.1016/j.pep.2015.02.002. Epub Feb. 7, 2015. PMID: 25665506. (Year: 2015).*
Ahern, H. Biochemical, reagents kits offer scientists good return on investment. The Scientist Magazine®. https://www.the-scientist.com/biochemical-reagents-kits-offer-scientists-good-return-on-investment-58425 (Year: 1995).*
Berge, V.D., et al., "RNA Sequencing Data: Hitchhiker's Guide to Expression Analysis," Annual Review of Biomedical Data Science 2(1):139-173, Annual Reviews, United States (Jul. 2019).
Brennan, A., et al., "Selective Antagonism of cJun for Cancer Therapy," Journal of Experimental & Clinical Cancer Research 39(1):184, BioMed Central, England (Sep. 2020).
Ferguson, K.M., "Structure-based View of Epidermal Growth Factor Receptor Regulation," Annual Review of Biophysics 37:353-373, Annual Reviews, United States (Feb. 2008).
Geraci, F., et al., "Editorial: RNA-Seq Analysis: Methods, Applications and Challenges," Frontiers in Genetics 11:220, Frontiers Research Foundation, Switzerland (Mar. 2020).
Hedger, G., et al., "The Juxtamembrane Regions of Human Receptor Tyrosine Kinases Exhibit Conserved Interaction Sites With Anionic Lipids," Scientific Reports 5:9198, Nature Publishing Group, United Kingdom (Mar. 2015).
Kabadi, A.M. and Gersbach, C.A., "Engineering Synthetic Tale and CRISPR/cas9 Transcription Factors for Regulating Gene Expression," Methods 69(2):188-197, Academic Press, United States (Sep. 2014).
Kudla, G., et al., "High Guanine and Cytosine Content Increases mRNA Levels in Mammalian Cells," PLoS Biology 4(6):e180, Public Library of Science, United States (Jun. 2006).
Milone, M.C., et al., "Chimeric Receptors Containing CD137 Signal Transduction Domains Mediate Enhanced Survival of T Cells and Increased Antileukemic Efficacy in Vivo," Molecular Therapy 17(8): 1453-1464, Cell Press, United States (Aug. 2009).
Nissim, L., et al., "Multiplexed and Programmable Regulation of Gene Networks With an Integrated RNA and CRISPR/Cas Toolkit in Human Cells," Molecular Cell 54(4):698-710, Cell Press, United States (May 2014).
Pandelakis, M., et al., "CRISPR-Based Synthetic Transcription Factors in Vivo: the Future of Therapeutic Cellular Programming," Cell Systems 10(1):1-14, Cell Press, United States (Jan. 2020).
Pietrobon, V., et al., "Improving CAR T-Cell Persistence," International Journal of Molecular Sciences 22(19):10828, MDPI, Switzerland (Oct. 2021).
Sharp, P.M. and Li, W.H., "The Codon Adaptation Index—a Measure of Directional Synonymous Codon Usage Bias, and Its Potential Applications," Nucleic Acids Research 15(3):1281-1295, Oxford University Press, England (Feb. 1987).
Sturm, G., et al., "Comprehensive Evaluation of Transcriptome-based Cell-type Quantification Methods for Immuno-oncology," Bioinformatics 35(14):i436-i445, Oxford University Press, England (Jul. 2019).
Yang, Z., et al., "Contextual Reprogramming of CAR-T Cells for Treatment of HER2 + Cancers," Journal of Translational Medicine 19(1):459, BioMed Central, England (Nov. 2021).
Yang, Z., et al., "Context-dependent Reversible Modulation of cJUN Expression by Car T Cells for Cancer Treatment," Journal for Immunotherapy of Cancer 9(Suppl 2):A164, 2021).
Zhao, S., et al., "Piggybac Transposon Vectors: the Tools of the human gene encoding," Translational Lung Cancer Research 5(1):120-125, Pioneer Bioscience Publishing Company, China (Feb. 2016).

* cited by examiner

SEQUENCE LISTING

<160> NUMBER OF SEQ ID NOS: 74

<210> SEQ ID NO 1
<211> LENGTH: 993
<212> TYPE: DNA
<213> ORGANISM: Artificial Sequence
<220> FEATURE:
<223> OTHER INFORMATION: Codon-optimized c-Jun nucleotide sequence #1

<400> SEQUENCE: 1

| | | | | | |
|---|---|---|---|---|---|
| atgacagcca | agatggaaac | cacattctac | gacgacgccc | tgaacgcctc | attcctgcct | 60 |
| tctgagagcg | gaccttacgg | ctacagcaat | cctaagatcc | tgaaacagag | catgaccctt | 120 |
| aacctggctg | atcctgttgg | aagcctgaaa | cctcacctga | gccaaaaaa  | cagcgacctg | 180 |
| ctcaccagcc | ctgatgtggg | cctgctgaag | ctggcctctc | agagctgga  | acggctgatc | 240 |
| atccagagca | gcaacggcca | catcacaacc | accctaccc  | ctacacaatt | cctgtgccct | 300 |
| aagaacgtga | ccgacgagca | ggagggcttc | gccgaaggct | ttgtgcgggc | cctggcagaa | 360 |
| ctgcactctc | agaacaccct | gcctagcgtg | acctccgccg | cccagcctgt | caacggcgcc | 420 |
| ggaatggtgg | cccctgccgt | ggcttctgtg | gccggcggca | gcggcagcgg | cggattcagc | 480 |
| gcctctctgc | actctgagcc | tcctgtctac | gccaatctgt | ctaatttcaa | ccccggagcc | 540 |
| ctgtccagcg | gcggcggagc | tcctagctac | ggcgctgctg | gactggcctt | ccccgcccag | 600 |
| ccccagcaac | agcagcagcc | tccacaccac | ctgccccagc | agatgcccgt | gcagcaccct | 660 |
| agactgcagg | ccctgaagga | agaacccaa  | acagtgcctg | agatgcctgg | cgagacacct | 720 |
| ccactgagcc | ccatcgacat | ggaaagccag | agcggatca  | aggccgagag | aaagagaatg | 780 |
| cggaacagaa | tcgccgctag | caagtgcaga | aagcggaagc | tggaaagaat | cgccagactg | 840 |
| gaagagaagg | tgaagaccct | gaaagcccaa | aatagcgagc | tggccagcac | cgccaacatg | 900 |
| ctgcgggaac | aggtggccca | gctgaagcag | aaggtgatga | accacgtgaa | ctctggttgt | 960 |
| cagctgatgc | tgacccagca | gctccagacc | ttc | | | 993 |

<210> SEQ ID NO 2
<211> LENGTH: 993
<212> TYPE: DNA
<213> ORGANISM: Artificial Sequence
<220> FEATURE:
<223> OTHER INFORMATION: Codon-optimized c-Jun nucleotide sequence #2

<400> SEQUENCE: 2

| | | | | | |
|---|---|---|---|---|---|
| atgacagcca | agatggaaac | caccttctac | gacgacgccc | tcaacgcctc | cttcctgcct | 60 |
| tctgagagcg | gtccttacgg | ctacagcaac | cccaagatcc | tgaagcaaag | catgaccctg | 120 |
| aacctggccg | accccgttgg | ctccctgaaa | cctcacctga | gccaaaaaa  | cagcgacctg | 180 |
| ctgaccagcc | ctgatgtggg | cctgctgaag | ctggcctctc | agagctgga  | aagactgatt | 240 |
| atccagagca | gcaacggcca | catcaccaca | acacctaccc | ctacacagtt | cctgtgccct | 300 |
| aagaacgtga | ctgatgagca | ggagggcttt | gccgagggct | tcgtgagagc | cctggctgag | 360 |
| ctgcattctc | agaacaccct | gcctagcgtg | acctctgccg | cccagcctgt | taatggcgcc | 420 |
| ggcatggtgg | cccctgccgt | ggcctctgtg | gccggaggca | gcggcagcgg | cggattcagc | 480 |
| gcctctctgc | acagcgagcc | ccccgtctac | gccaacctga | gcaatttcaa | ccctggcgcc | 540 |
| ctgtccagcg | gcggcggcgc | ccctagctat | ggcgctgccg | gcctggcctt | ccccgctcag | 600 |
| ccccagcagc | agcaacagcc | tccacaccac | ctgccccagc | agatgcccgt | gcagcacccc | 660 |
| agactgcagg | ccctgaagga | agaacctcag | accgtgcccg | agatgcctgg | cgagacccct | 720 |

```
cctctgagcc ctatcgacat ggaaagccag gagagaatca aggccgagag gaagcggatg    780
cggaacagaa tcgccgccag caagtgcaga aaaagaaagc tggaacggat cgccagactg    840
gaggagaagg tgaagacact gaaagcccaa aattctgaac tggcctctac cgccaatatg    900
ctgcgcgagc aggtggctca actgaagcag aaggtgatga accacgtgaa cagcggatgt    960
cagctgatgc tgacacagca gctgcagact ttt                                 993
```

<210> SEQ ID NO 3
<211> LENGTH: 993
<212> TYPE: DNA
<213> ORGANISM: Artificial Sequence
<220> FEATURE:
<223> OTHER INFORMATION: Codon-optimized c-Jun nucleotide sequence #3

<400> SEQUENCE: 3

```
atgaccgcca agatggaaac caccttctac gacgacgccc tgaacgccag ctttctgcct     60
tctgagtctg gccctacgg ctacagcaac cccaagatcc tgaagcagag catgaccctg    120
aacctggccg atcctgtggg cagcctgaaa cctcacctga gccaagaa cagcgacctg     180 ctgacaagcc ctgatgtggg cctgctgaaa ctggcctctc tgagctgga acggctgatc    240 atccagagca gcaacggcca catcaccacc acacctacac caacacagtt tctgtgcccc    300
aagaacgtga ccgacgagca gagggattc gccgagggct tgttagagc cctggccgaa    360 ctgcacagcc agaataccct gcctagcgtg acatctgccg ctcagcctgt taatggcgcc    420
ggaatggttg ctcctgccgt ggcttctgtt gctggcggat ctggatctgg cggctttagc    480
gcctctctgc actctgagcc tccagtgtac gccaacctga gcaacttcaa ccctggcgct    540 cttagtctg gtggcggagc accttcttat ggcgctgccg gattggcctt tcctgctcag    600
cctcagcagc agcaacagcc tcctcatcat ctgccccagc agatgcctgt gcagcaccct    660
agactgcagg ccctgaaaga ggaaccccag acagtccctg agatgccggg cgaaacacct    720
cctctgagcc ccatcgacat ggaaagccaa gagcggatca aggccgagcg gaagcggatg    780
agaaatagaa tcgccgcctc caagtgccgg aagaggaagc tggaaagaat cgcccggctg    840
gaagagaaag tgaaaaccct gaaggcccag aactccgagc tggcctctac cgccaacatg    900
ctgagagaac aggtggccca gctgaaaacag aaagtcatga accacgtgaa cagcggctgc    960
cagctgatgc tgacacagca gctgcagacc ttc                                 993
```

<210> SEQ ID NO 4
<211> LENGTH: 993
<212> TYPE: DNA
<213> ORGANISM: Artificial Sequence
<220> FEATURE:
<223> OTHER INFORMATION: Codon-optimized c-Jun nucleotide sequence #4

<400> SEQUENCE: 4

```
atgactgcca aaatggagac tacattctat gacgacgccc tcaatgccag tttttttgccg     60 agtgaatccg gccccctacgg ctattcaaac cctaagatcc tcaagcaatc aatgaccctc    120
aatcttgctg acccagttgg ctccctgaaa ccccatctca gagctaaaaa tagtgacctc    180
cttacttccc ctgatgttgg actcctcaaa cttgcttctc ccgaactcga acgcttgatc    240
attcaatctt ccaacggcca catcacaaca cacccacac ccacccagtt tctttgccca    300
aaaaatgtca ccgatgaaca ggaaggtttc gcggaaggat cgtccgcgc gctggccgaa    360 ctgcactccc agaatacact tccttcagtt acgtcagccg cccagccagt gaatggtgcg    420
```

| ggaatggttg | ctcctgcggt | cgcttctgtc | gcaggggggct | ccggttctgg | cggatttagc | 480 |
| gcctctctgc | attccgagcc | acctgtatat | gctaatcttt | ctaattttaa | ccccggagcc | 540 |
| ttgtctagcg | gcggtggtgc | ccccagctac | ggtgctgcag | gactcgcctt | cccagctcaa | 600 |
| cctcagcagc | agcaacaacc | cccccatcac | cttccccaac | agatgccagt | acaacatcca | 660 |
| aggctccagg | ccctcaaaga | ggaaccacag | acggtgcccg | aaatgcctgg | cgaaactcca | 720 |
| ccactttccc | ctattgatat | ggaatcccaa | gagcgcatca | aggccgaaag | aaagcgaatg | 780 |
| cggaatagaa | tagcagcttc | aaaatgtaga | aaacggaaat | tggaacgaat | cgcacggttg | 840 |
| gaagaaaagg | tgaagacctt | gaaagcccag | aacagtgagc | tcgcctctac | cgctaacatg | 900 |
| ctgcgcgagc | aagtcgcaca | acttaagcag | aaggtgatga | accatgtgaa | tagcggatgt | 960 |
| caacttatgc | tgactcaaca | gttgcaaacc | ttt        |            |            | 993 |

<210> SEQ ID NO 5
<211> LENGTH: 993
<212> TYPE: DNA
<213> ORGANISM: Artificial Sequence
<220> FEATURE:
<223> OTHER INFORMATION: Codon-optimized c-Jun nucleotide sequence #5

<400> SEQUENCE: 5

| atgaccgcga | aaatggagac | aacattttac | gatgatgcac | tgaacgcctc | ttttctgcca | 60 |
| agtgaatccg | gcccctacgg | atactcaaac | cctaagattc | tgaaacagtc | tatgactctc | 120 |
| aacctggccg | acccagttgg | cagtctgaag | cctcatttgc | gagccaagaa | tagtgatctg | 180 |
| ctgacctccc | cagacgtggg | actgctgaaa | ctcgcctcac | ctgaacttga | gcgcttgatt | 240 |
| atacagtcat | ccaatgggca | catcacaaca | cacctactc | ctacccagtt | tctgtgcccc | 300 |
| aaaaacgtca | ccgatgagca | ggagggattc | gcggaaggct | ttgtgcgcgc | cctggctgaa | 360 |
| ttgcatagtc | agaacactct | tcccagcgta | accagcgccg | cccaaccagt | gaatggagcc | 420 |
| ggtatggtgg | ctcccgcggt | ggctagtgtt | gcggggggggt | caggctctgg | tgggttcagt | 480 |
| gcttctcttc | actctgaacc | cctgtgtat | gccaatctgt | ctaactttaa | ccctggggcc | 540 |
| ctctcctctg | gtgggggtgc | cccagctac | ggagcggccg | gctggccctt | tcctgcccag | 600 |
| cctcagcagc | agcagcaacc | cctcatcat | cttccgcagc | agatgccagt | acagcatcca | 660 |
| cgcctgcagg | ctcttaagga | ggagcccag | acggtgcccg | aaatgcccgg | ggaaactcca | 720 |
| cccttgtccc | ccattgacat | ggagtcccag | gagcggatca | aggctgaaag | aaagaggatg | 780 |
| cggaatcgca | tcgcagcctc | taaatgccgc | aagcggaaac | ttgagaggat | cgcgcggttg | 840 |
| gaggaaaaag | taaaaaacctt | gaaggcacag | aactctgagc | tggcgagtac | tgccaacatg | 900 |
| ctcagagaac | aagtcgcaca | gctgaagcag | aaagtgatga | accatgtgaa | cagcggttgt | 960 |
| cagctgatgc | tgactcagca | gctgcagacc | ttc        |            |            | 993 |

<210> SEQ ID NO 6
<211> LENGTH: 993
<212> TYPE: DNA
<213> ORGANISM: Artificial Sequence
<220> FEATURE:
<223> OTHER INFORMATION: Codon-optimized c-Jun nucleotide sequence #6

<400> SEQUENCE: 6

| atgaccgcca | agatggagac | cacattctac | gatgacgctc | tgaacgcttc | ctttctgcct | 60 |
| tccgagtccg | gcccctacgg | ctactccaat | cccaagattc | tgaagcagag | catgacactg | 120 |
| aatctggctg | atcccgtggg | atctctgaag | cctcatctga | gagccaagaa | ttccgatctg | 180 |

```
ctgacaagcc ccgacgtggg actgctcaaa ctggccagcc ccgaactgga gaggctcatt      240
atccagagct ccaacggcca catcaccaca acacctaccc ctacccagtt tctctgtccc      300
aagaacgtga cagacgagca agagggattt gccgaaggct tcgtgagagc cctcgccgaa      360
ctgcatagcc agaacacact gccttccgtg accagcgctg ctcaacccgt gaacggcgct      420
ggcatggtcg ctcccgccgt cgccagcgtg gctggaggaa gcggatccgg aggcttcagc      480
gcttccctcc acagcgaacc tcccgtgtac gctaatctga gcaacttcaa ccccggcgct      540
ctgagcagcg aggaggagc tcctagctat ggagctgccg actggctttt cccgcccag       600 ccccagcagc agcagcagcc ccccatcat ctgcctcagc agatgcccgt gcagcatccc       660
agactccaag ctctgaagga ggagcctcag accgtccccg agatgcccgg cgaaaccccc     720
cctctgtccc ccatcgacat ggaaagccaa gagaggatca aggccgagag aaagaggatg      780
aggaatagaa tcgccgccag caagtgtaga aagaggaagc tggagaggat cgccagactg      840
gaggagaagg tgaagaccct caaggctcag aattccgagc tggccagcac agccaacatg      900
ctgagagagc aagtggccca gctcaagcag aaggtgatga accacgtcaa cagcggatgc      960
cagctgatgc tcacccagca gctgcagacc ttc                                  993

<210> SEQ ID NO 7
<211> LENGTH: 993
<212> TYPE: DNA
<213> ORGANISM: Artificial Sequence
<220> FEATURE:
<223> OTHER INFORMATION: Codon-optimized c-Jun nucleotide sequence #7

<400> SEQUENCE: 7
atgaccgcta aaatggaaac cactttctat gacgatgccc tgaacgcctc cttccttccg      60
tccgagtccg accctacgg atactcaaat cctaagatcc tcaaacagtc gatgaccctc      120
aacctggccg acccgtggg atccctgaag ccgcacttgc gcgccaagaa ctccgacctc      180
ctgacgagcc cagacgtggg cctgctgaag ctcgcatcac ccgaacttga gcggttgatc      240
attcagtcct ccaacggaca tatcaccacc actcccaccc caactcagtt tctgtgtccg      300
aagaacgtga ccgatgagca agagggattc gccgagggat tcgtgcgggc cctggccgag      360
ctgcatagcc agaacaccct tccatccgtg acctcggcgg ctcagcctgt gaacggcgcg      420
ggaatggtcg cgcccgccgt ggcctcggtg gccgggggca gcggcagcgg gggattttcc      480
gcgtcgctgc actccgagcc gccggtgtac gccaacctgt caaacttcaa ccctggggcc      540
ctgagctccg cggtggagc accttcgtac ggcgccgctg gctggcgtt ccccgcgcaa        600 ccacagcagc aacagcagcc ccctcaccac ctcccccaac aaatgcctgt gcagcacccg      660
aggctgcagg ccctcaagga agaacccag actgtgccgg aaatgccggg ggagactccg      720
ccgctgtccc ctatcgacat ggaatcacag gaacgcatta aggcagagcg gaagcgcatg      780
cggaaccgga ttgccgcctc caagtgccgc aagagaaagc tcgaaagaat cgccagattg      840
gaagaaaagg tcaagactct gaaggcccag aactctgagc tggcatccac cgctaatatg      900
ctgagggaac aagtggccca gctgaaacag aaggtcatga accacgtcaa cagcggttgc      960
cagctgatgc tgacccagca actccagaca ttc                                  993

<210> SEQ ID NO 8
<211> LENGTH: 993
<212> TYPE: DNA
<213> ORGANISM: Artificial Sequence
<220> FEATURE:
```

<223> OTHER INFORMATION: Codon-optimized c-Jun nucleotide sequence #8

<400> SEQUENCE: 8

```
atgaccgcca agatggagac caccttctac gacgacgccc tgaacgccag cttcctgccc    60
agcgagagcg accctacgg ctactctaac cccaagatcc tgaaacagag catgacactg   120
aatctggccg accccgtggg cagcctgaag cctcaccttaa gagccaagaa cagcgacctg   180
ctgaccagcc ccgacgtggg cctgctgaag ctcgcctctc cagagttaga gagactgatc   240
atccagtcca gcaacggcca catcacaacc accccaaccc tacccagtt cctgtgcccc   300
aagaacgtga ccgacgagca ggagggcttc gccgagggct tgtgagagc cctggccgag   360
ttgcactctc agaacaccct gccctccgtg accagcgccg ctcaacctgt gaacggcgca   420
ggaatggttg ctcctgccgt ggccagcgtt gcaggcggat ctggaagtgg aggcttctcc   480
gcctcccttc acagcgagcc tcccgtgtac gccaacctga gcaacttcaa ccccggcgcc   540
ctgagcagtg gaggaggcgc tcccagctat ggagcagctg gattagcctt ccccgcccag   600
ccacagcagc agcaacagcc tccccaccac ctgcctcagc aaatgcctgt gcagcaccct   660
cggctgcagg cccttaagga ggagcccag accgttcctg atgcctgg cgagacccct   720
cccctgagcc ctatcgacat ggagtccag gagcggatca aggccgagcg gaagcggatg   780
cggaaccgga tcgctgcttc caagtgccgg aagagaaagc tggagagaat cgcccggctg   840
gaggagaagg tgaagaccct gaaggcccag aactccgagc tggcctccac cgccaacatg   900
ctgcgggagc aggttgcaca gctgaagcag aaggtcatga ccacgtgaa cagcggctgc   960
cagctgatgc tgacccagca gctgcagacc ttc                              993
```

<210> SEQ ID NO 9
<211> LENGTH: 1059
<212> TYPE: DNA
<213> ORGANISM: Artificial Sequence
<220> FEATURE:
<223> OTHER INFORMATION: Codon-optimized c-Jun nucleotide sequence #9

<400> SEQUENCE: 9

```
atgacagcga agatggagac aaccttctat gacgatgctc ttaacgcctc cttcctgcct    60
tccgaaagcg ggccctacgg gtactctaat cctaagatac ttagcaatc gatgactctc   120
aacctcgctg accggttgg ctcactgaaa ccacacctga gctaagaa tagtgacctg   180
ctcactagtc ccgatgtcgg gcttctgaag ctggcctctc ccgagctgga gaggcttatc   240
atccaatcat caaatggcca catcaccact accccaacac caactcaatt cctttgccct   300
aaaaacgtga ccgacgaaca ggaaggcttc gccgagggtt tgtccgggc cttggccgag   360
ctgcattctc aaaatacact gccaagcgtc acttctgcgg cgcagccggt taacggagca   420
gggatggtgg ctcccgccgt tgctagcgtg gccgcggtt ccggctccgg cggtttctct   480
gcctccttgc attctgagcc accagtctac gcgaacctgt ccaactttaa tccgggggcg   540
ctgagtagcg gaggcggcgc ccctagctat ggggcagctg gactggcctt ccggcacaa   600
ccccaacaac aacagcaacc gccacaccat cttcctcaac aaatgccagt gcaacatcca   660
cgcttacaag ccctcaagga ggaaccccag accgtgcctg atgcccgg cgaaaccccg   720
ccattgagcc ctattgacat ggaaagtcaa gagagaatta aggcagagcg caagagaatg   780
aggaaccgga tcgcagcatc taagtgccgc aaacggaaat ggagcggat cgctcgcttg   840
gaggagaagg tcaagactct caaggcccag aactccgagc ttgcgagcac agctaatatg   900
ctgcgcgagc aggtggccca gttaaaacaa aaggtcatga ccatgtgaa cagcggctgt   960
```

```
cagctgatgc ttacgcaaca gctgcaaacc tttggctccg gtgcaacgaa cttcagcctg    1020
ctgaagcagg ccggagatgt tgaggaaaat ccaggtccc                            1059
```

<210> SEQ ID NO 10
<211> LENGTH: 993
<212> TYPE: DNA
<213> ORGANISM: Artificial Sequence
<220> FEATURE:
<223> OTHER INFORMATION: Codon-optimized c-Jun nucleotide sequence #10

<400> SEQUENCE: 10

```
atgacggcca aaatggagac tacgttctac gatgacgcac tcaacgcgtc cttcctgccc     60
tctgagagtg acccctatgg ctactccaat ccaaagatcc tgaagcagtc tatgaccctc    120
aacctggcgg acccggtggg ctcccttaag ccgcacttgc gcgccaagaa ctccgacctg    180
ctgacctccc ctgatgtggg cctcctcaag ctcgctagcc ctgaattgga gaggctgatc    240
atccagagct caaatggcca catcaccacc acacctaccc aacccagtt cctgtgccca    300 aaaaacgtga ccgacgagca ggagggcttc gcggagggct cgtcagagc tctggccgag    360 ctgcactcac agaacacgct cccttccgtg acctccgctg cccagccggt caatggcgct    420
ggaatggtgg ctccggctgt ggcctctgtt gccgcggct ccggctccgg aggcttttca    480
gcttctctgc attctgagcc cccagtgtac gctaacctga gcaacttcaa ccccggggcg    540
ctcagctccg gtggcggtgc cccgagctac ggcgcggctg ggctggcgtt ccccgctcag    600
cctcagcagc aacagcaacc tccccaccac ctgccacagc agatgcctgt gcagcaccca    660
cgcctgcagg ccttgaagga ggaacctcag actgtgccag atgcccgg cgagaccca    720 ccctgtccc cgattgacat ggagagccag gagcgcatca aggcagagcg caagcgtatg    780
cgcaaccgca tcgcggcctc caagtgccga aagcgcaagc tggagcggat tgctcgcctg    840
gaggagaagg tgaagaccct gaaggccag aattccgagc tggcctcgac cgccaacatg    900
ctacgagaac aggtcgcgca gctgaaacag aaggtcatga accatgtcaa cagcgggtgc    960
cagctgatgt tgacccagca gcttcagacc ttc                                 993
```

<210> SEQ ID NO 11
<211> LENGTH: 993
<212> TYPE: DNA
<213> ORGANISM: Artificial Sequence
<220> FEATURE:
<223> OTHER INFORMATION: Wild-type c-Jun - coding region

<400> SEQUENCE: 11

```
atgactgcaa agatggaaac gaccttctat gacgatgccc tcaacgcctc gttcctcccg     60
tccgagagcg gaccttatgg ctacagtaac cccaagatcc tgaaacagag catgaccctg    120
aacctggccg acccagtggg gagcctgaag ccgcacctcc gcgccaagaa ctcggacctc    180
ctcacctcgc ccgacgtggg gctgctcaag ctggcgtcgc ccgagctgga gcgcctgata    240
atccagtcca gcaacgggca tcaccacc cgccgaccc ccacccagtt cctgtgcccc    300
aagaacgtga cagatgagca gggggcttc gccgagggct cgtgcgcgc cctggccgaa    360 ctgcacagcc agaacacgct gcccagcgtc acgtcgcgg cgcagccggt caacgggca    420 ggcatggtgg ctcccgcggt agcctcggtg caggggca gcggcagcgg cggcttcagc    480
gccagcctgc acagcgagcc gccggtctac gcaaacctca gcaacttcaa cccaggcgcg    540
ctgagcagcg gcggcggggc gccctccta ggcgcggccg gctggcctt tcccgcgcaa    600
```

| cccccagcagc agcagcagcc gccgcaccac ctgccccagc agatgcccgt gcagcacccg | 660 |
| cggctgcagg ccctgaagga ggagcctcag acagtgcccg agatgcccgg cgagacaccg | 720 |
| cccctgtccc ccatcgacat ggagtcccag gagcggatca aggcggagag gaagcgcatg | 780 |
| aggaaccgca tcgctgcctc caagtgccga aaaaggaagc tggagagaat cgcccggctg | 840 |
| gaggaaaaag tgaaaacctt gaaagctcag aactcggagc tggcgtccac ggccaacatg | 900 |
| ctcagggaac aggtggcaca gcttaaacag aaagtcatga accacgttaa cagtgggtgc | 960 |
| caactcatgc taacgcagca gttgcaaaca ttt | 993 |

<210> SEQ ID NO 12
<211> LENGTH: 3257
<212> TYPE: DNA
<213> ORGANISM: Artificial Sequence
<220> FEATURE:
<223> OTHER INFORMATION: Wild-type c-Jun

<400> SEQUENCE: 12

| gctcagagtt gcactgagtg tggctgaagc agcgaggcgg gagtggaggt gcgcggagtc | 60 |
| aggcagacag acagacacag ccagccagcc aggtcggcag tatagtccga actgcaaatc | 120 |
| ttatttctt ttcaccttct ctctaactgc ccagagctag cgcctgtggc tcccgggctg | 180 |
| gtgtttcggg agtgtccaga gagcctggtc tccagccgcc cccggaagga gagccctgct | 240 |
| gcccaggcgc tgttgacagc ggcggaaagc agcggtaccc acgcgcccgc cggggggaagt | 300 |
| cggcgagcgg ctgcagcagc aaagaacttt cccggctggg aggaccggag acaagtggca | 360 |
| gagtcccgga gccaacttttt gcaagccttt cctgcgtctt aggcttctcc acggcggtaa | 420 |
| agaccagaag gcggcggaga gccacgcaag agaagaagga cgtgcgctca gcttcgctcg | 480 |
| caccggttgt tgaacttggg cgagcgcgag ccgcggctgc cgggcgcccc ctccccctag | 540 |
| cagcggagga ggggacaagt cgtcggagtc cgggcggcca agacccgccg ccggccggcc | 600 |
| actgcagggt ccgcactgat ccgctccgcg gggagagccg ctgctctggg aagtgagttc | 660 |
| gcctgcggac tccgaggaac cgctgcgcac gaagagcgct cagtgagtga ccgcgacttt | 720 |
| tcaaagccgg gtagcgcgcg cgagtcgaca agtaagagtg cggaggcat cttaattaac | 780 |
| cctgcgctcc ctggagcgag ctggtgagga gggcgcagcg gggacgacag ccagcgggtg | 840 |
| cgtgcgctct tagagaaact ttccctgtca aaggctccgg ggggcgcggg tgtccccgc | 900 |
| ttgccacagc cctgttgcgg ccccgaaact tgtgcgcgca gcccaaacta acctcacgtg | 960 |
| aagtgacgga ctgttctatg actgcaaaga tggaaacgac cttctatgac gatgccctca | 1020 |
| acgcctcgtt cctcccgtcc gagagcggac cttatggcta cagtaacccc aagatcctga | 1080 |
| aacagagcat gaccctgaac ctggccgacc cagtggggag cctgaagccg cacctccgcg | 1140 |
| ccaagaactc ggacctcctc acctcgcccg acgtggggct gctcaagctg gcgtcgcccg | 1200 |
| agctggagcg cctgataatc cagtccagca cgggcacat caccaccacg ccgacccca | 1260 |
| cccagttcct gtgccccaag aacgtgacag atgagcagga gggcttcgcc gagggcttcg | 1320 |
| tgcgcgccct ggccgaactg cacagccaga acacgctgcc cagcgtcacg tcggcggcgc | 1380 |
| agccggtcaa cggggcaggc atggtggctc ccgcggtagc ctcggtggca gggggcagcg | 1440 |
| gcagcggcgg cttcagcgcc agcctgcaca gcgagccgcc ggtctacgca aacctcagca | 1500 |
| acttcaaccc aggcgcgctg agcagcggcg gcggggcgcc ctcctacggc gcggccggcc | 1560 |
| tggccttttcc cgcgcaaccc cagcagcagc agcagccgcc gcaccacctg ccccagcaga | 1620 |
| tgcccgtgca gcacccgcgg ctgcaggccc tgaaggagga gcctcagaca gtgcccgaga | 1680 |

```
tgcccggcga gacaccgccc ctgtccccca tcgacatgga gtcccaggag cggatcaagg    1740
cggagaggaa gcgcatgagg aaccgcatcg ctgcctccaa gtgccgaaaa aggaagctgg    1800
agagaatcgc ccggctggag gaaaaagtga aaaccttgaa agctcagaac tcggagctgg    1860
cgtccacggc caacatgctc agggaacagg tggcacagct aaacagaaa gtcatgaacc    1920 acgttaacag tgggtgccaa ctcatgctaa cgcagcagtt gcaaacattt tgaagagaa    1980 ccgtcggggg ctgaggggca acgaagaaaa aaaataacac agagagacag acttgagaac    2040
ttgacaagtt gcgacggaga gaaaaagaa gtgtccgaga actaaagcca agggtatcca    2100
agttggactg ggttgcgtcc tgacggcgcc cccagtgtgc acgagtggga aggacttggc    2160
gcgccctccc ttggcgtgga gccagggagc ggccgcctgc gggctgcccc gctttgcgga    2220
cgggctgtcc ccgcgcgaac ggaacgttgg acttttcgtt aacattgacc aagaactgca    2280
tggacctaac attcgatctc attcagtatt aaggggggga gggggagggg gttacaaact    2340
gcaatagaga ctgtagattg cttctgtagt actccttaag aacacaaagc gggggagggg    2400
ttggggaggg gcggcaggag ggaggtttgt gagagcgagg ctgagcctac agatgaactc    2460
tttctggcct gccttcgtta actgtgtatg tacatatata tattttttaa tttgatgaaa    2520
gctgattact gtcaataaac agcttcatgc ctttgtaagt tatttcttgt ttgtttgttt    2580
gggtatcctg cccagtgttg tttgtaaata agagatttgg agcactctga gtttaccatt    2640
tgtaataaag tatataattt ttttatgttt tgtttctgaa aattccagaa aggatattta    2700
agaaaataca ataaactatt ggaaagtact cccctaacct cttttctgca tcatctgtag    2760
atactagcta tctaggtgga gttgaaagag ttaagaatgt cgattaaaat cactctcagt    2820
gcttcttact attaagcagt aaaaactgtt ctctattaga ctttagaaat aaatgtacct    2880
gatgtacctg atgctatggt caggttatac tcctcctccc ccagctatct atatggaatt    2940
gcttaccaaa ggatagtgcg atgtttcagg aggctggagg aagggggtt gcagtggaga    3000 gggacagccc actgagaagt caaacatttc aaagtttgga ttgtatcaag tggcatgtgc    3060
tgtgaccatt tataatgtta gtagaaattt tacaataggt gcttattctc aaagcaggaa    3120
ttggtggcag attttacaaa agatgtatcc ttccaatttg gaatcttctc tttgacaatt    3180
cctagataaa aagatggcct ttgcttatga atatttataa cagcattctt gtcacaataa    3240
atgtattcaa ataccaa                                                  3257
```

<210> SEQ ID NO 13
<211> LENGTH: 331
<212> TYPE: PRT
<213> ORGANISM: Artificial Sequence
<220> FEATURE:
<223> OTHER INFORMATION: Wild-type c-Jun

<400> SEQUENCE: 13

```
Met Thr Ala Lys Met Glu Thr Thr Phe Tyr Asp Asp Ala Leu Asn Ala
1               5                   10                  15

Ser Phe Leu Pro Ser Glu Ser Gly Pro Tyr Gly Tyr Ser Asn Pro Lys
            20                  25                  30

Ile Leu Lys Gln Ser Met Thr Leu Asn Leu Ala Asp Pro Val Gly Ser
        35                  40                  45

Leu Lys Pro His Leu Arg Ala Lys Asn Ser Asp Leu Leu Thr Ser Pro
    50                  55                  60

Asp Val Gly Leu Leu Lys Leu Ala Ser Pro Glu Leu Glu Arg Leu Ile
65                  70                  75                  80
```

```
Ile Gln Ser Ser Asn Gly His Ile Thr Thr Thr Pro Thr Pro Thr Gln
                85                  90                  95

Phe Leu Cys Pro Lys Asn Val Thr Asp Glu Gln Glu Gly Phe Ala Glu
            100                 105                 110

Gly Phe Val Arg Ala Leu Ala Glu Leu His Ser Gln Asn Thr Leu Pro
        115                 120                 125

Ser Val Thr Ser Ala Ala Gln Pro Val Asn Gly Ala Gly Met Val Ala
130                 135                 140

Pro Ala Val Ala Ser Val Ala Gly Gly Ser Gly Ser Gly Gly Phe Ser
145                 150                 155                 160

Ala Ser Leu His Ser Glu Pro Pro Val Tyr Ala Asn Leu Ser Asn Phe
                165                 170                 175

Asn Pro Gly Ala Leu Ser Ser Gly Gly Gly Ala Pro Ser Tyr Gly Ala
            180                 185                 190

Ala Gly Leu Ala Phe Pro Ala Gln Pro Gln Gln Gln Gln Pro Pro
        195                 200                 205

His His Leu Pro Gln Gln Met Pro Val Gln His Pro Arg Leu Gln Ala
    210                 215                 220

Leu Lys Glu Glu Pro Gln Thr Val Pro Glu Met Pro Gly Glu Thr Pro
225                 230                 235                 240

Pro Leu Ser Pro Ile Asp Met Glu Ser Gln Glu Arg Ile Lys Ala Glu
                245                 250                 255

Arg Lys Arg Met Arg Asn Arg Ile Ala Ala Ser Lys Cys Arg Lys Arg
            260                 265                 270

Lys Leu Glu Arg Ile Ala Arg Leu Glu Glu Lys Val Lys Thr Leu Lys
        275                 280                 285

Ala Gln Asn Ser Glu Leu Ala Ser Thr Ala Asn Met Leu Arg Glu Gln
290                 295                 300

Val Ala Gln Leu Lys Gln Lys Val Met Asn His Val Asn Ser Gly Cys
305                 310                 315                 320

Gln Leu Met Leu Thr Gln Gln Leu Gln Thr Phe
                325                 330

<210> SEQ ID NO 14
<211> LENGTH: 19
<212> TYPE: PRT
<213> ORGANISM: Artificial Sequence
<220> FEATURE:
<223> OTHER INFORMATION: P2A Linker

<400> SEQUENCE: 14

Ala Thr Asn Phe Ser Leu Leu Lys Gln Ala Gly Asp Val Glu Glu Asn
1               5                   10                  15

Pro Gly Pro

<210> SEQ ID NO 15
<211> LENGTH: 18
<212> TYPE: PRT
<213> ORGANISM: Artificial Sequence
<220> FEATURE:
<223> OTHER INFORMATION: T2A Linker

<400> SEQUENCE: 15

Glu Gly Arg Gly Ser Leu Leu Thr Cys Gly Asp Val Glu Glu Asn Pro
1               5                   10                  15

Gly Pro
```

```
<210> SEQ ID NO 16
<211> LENGTH: 22
<212> TYPE: PRT
<213> ORGANISM: Artificial Sequence
<220> FEATURE:
<223> OTHER INFORMATION: F2A Linker

<400> SEQUENCE: 16

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 17
<211> LENGTH: 20
<212> TYPE: PRT
<213> ORGANISM: Artificial Sequence
<220> FEATURE:
<223> OTHER INFORMATION: E2A Linker

<400> SEQUENCE: 17

Gln Cys Thr Asn Tyr Ala Leu Leu Lys Leu Ala Gly Asp Val Glu Ser
1               5                   10                  15

Asn Pro Gly Pro
            20

<210> SEQ ID NO 18
<211> LENGTH: 4
<212> TYPE: PRT
<213> ORGANISM: Artificial Sequence
<220> FEATURE:
<223> OTHER INFORMATION: Furin Cleavage Site

<400> SEQUENCE: 18

Arg Ala Lys Arg
1

<210> SEQ ID NO 19
<211> LENGTH: 1210
<212> TYPE: PRT
<213> ORGANISM: Artificial Sequence
<220> FEATURE:
<223> OTHER INFORMATION: EGFR Isoform 1

<400> SEQUENCE: 19

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125
```

```
Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Asn Cys Gln
            195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
```

-continued

```
        545                 550                 555                 560
Glu Cys Leu Pro Gln Ala Met Asn Ile Thr Cys Thr Gly Arg Gly Pro
                        565                 570                 575
Asp Asn Cys Ile Gln Cys Ala His Tyr Ile Asp Gly Pro His Cys Val
                        580                 585                 590
Lys Thr Cys Pro Ala Gly Val Met Gly Glu Asn Asn Thr Leu Val Trp
                        595                 600                 605
Lys Tyr Ala Asp Ala Gly His Val Cys His Leu Cys His Pro Asn Cys
                        610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                        645                 650                 655
Leu Leu Val Val Ala Leu Gly Ile Gly Leu Phe Met Arg Arg Arg His
                        660                 665                 670
Ile Val Arg Lys Arg Thr Leu Arg Arg Leu Leu Gln Glu Arg Glu Leu
                        675                 680                 685
Val Glu Pro Leu Thr Pro Ser Gly Glu Ala Pro Asn Gln Ala Leu Leu
                        690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                        725                 730                 735
Lys Val Lys Ile Pro Val Ala Ile Lys Glu Leu Arg Glu Ala Thr Ser
                        740                 745                 750
Pro Lys Ala Asn Lys Glu Ile Leu Asp Glu Ala Tyr Val Met Ala Ser
                        755                 760                 765
Val Asp Asn Pro His Val Cys Arg Leu Leu Gly Ile Cys Leu Thr Ser
                        770                 775                 780
Thr Val Gln Leu Ile Thr Gln Leu Met Pro Phe Gly Cys Leu Leu Asp
785                 790                 795                 800
Tyr Val Arg Glu His Lys Asp Asn Ile Gly Ser Gln Tyr Leu Leu Asn
                        805                 810                 815
Trp Cys Val Gln Ile Ala Lys Gly Met Asn Tyr Leu Glu Asp Arg Arg
                        820                 825                 830
Leu Val His Arg Asp Leu Ala Ala Arg Asn Val Leu Val Lys Thr Pro
                        835                 840                 845
Gln His Val Lys Ile Thr Asp Phe Gly Leu Ala Lys Leu Leu Gly Ala
                        850                 855                 860
Glu Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                        885                 890                 895
Val Trp Ser Tyr Gly Val Thr Val Trp Glu Leu Met Thr Phe Gly Ser
                        900                 905                 910
Lys Pro Tyr Asp Gly Ile Pro Ala Ser Glu Ile Ser Ser Ile Leu Glu
                        915                 920                 925
Lys Gly Glu Arg Leu Pro Gln Pro Pro Ile Cys Thr Ile Asp Val Tyr
                        930                 935                 940
Met Ile Met Val Lys Cys Trp Met Ile Asp Ala Asp Ser Arg Pro Lys
945                 950                 955                 960
Phe Arg Glu Leu Ile Ile Glu Phe Ser Lys Met Ala Arg Asp Pro Gln
                        965                 970                 975
```

Arg Tyr Leu Val Ile Gln Gly Asp Glu Arg Met His Leu Pro Ser Pro
                980                 985                 990

Thr Asp Ser Asn Phe Tyr Arg Ala Leu Met Asp Glu Glu Asp Met Asp
            995                 1000                1005

Asp Val Val Asp Ala Asp Glu Tyr Leu Ile Pro Gln Gln Gly Phe
        1010                1015                1020

Phe Ser Ser Pro Ser Thr Ser Arg Thr Pro Leu Leu Ser Ser Leu
        1025                1030                1035

Ser Ala Thr Ser Asn Asn Ser Thr Val Ala Cys Ile Asp Arg Asn
        1040                1045                1050

Gly Leu Gln Ser Cys Pro Ile Lys Glu Asp Ser Phe Leu Gln Arg
        1055                1060                1065

Tyr Ser Ser Asp Pro Thr Gly Ala Leu Thr Glu Asp Ser Ile Asp
        1070                1075                1080

Asp Thr Phe Leu Pro Val Pro Glu Tyr Ile Asn Gln Ser Val Pro
        1085                1090                1095

Lys Arg Pro Ala Gly Ser Val Gln Asn Pro Val Tyr His Asn Gln
        1100                1105                1110

Pro Leu Asn Pro Ala Pro Ser Arg Asp Pro His Tyr Gln Asp Pro
        1115                1120                1125

His Ser Thr Ala Val Gly Asn Pro Glu Tyr Leu Asn Thr Val Gln
        1130                1135                1140

Pro Thr Cys Val Asn Ser Thr Phe Asp Ser Pro Ala His Trp Ala
        1145                1150                1155

Gln Lys Gly Ser His Gln Ile Ser Leu Asp Asn Pro Asp Tyr Gln
        1160                1165                1170

Gln Asp Phe Phe Pro Lys Glu Ala Lys Pro Asn Gly Ile Phe Lys
        1175                1180                1185

Gly Ser Thr Ala Glu Asn Ala Glu Tyr Leu Arg Val Ala Pro Gln
        1190                1195                1200

Ser Ser Glu Phe Ile Gly Ala
        1205                1210

<210> SEQ ID NO 20
<211> LENGTH: 405
<212> TYPE: PRT
<213> ORGANISM: Artificial Sequence
<220> FEATURE:
<223> OTHER INFORMATION: EGFR Isoform 2

<400> SEQUENCE: 20

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
        130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Asn Cys Gln
            195                 200                 205

Lys Leu Thr Lys Ile Ile Cys Ala Gln Gln Cys Ser Gly Arg Cys Arg
        210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
        290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
        370                 375                 380

Pro Pro Leu Asp Pro Gln Glu Leu Asp Ile Leu Lys Thr Val Lys Glu
385                 390                 395                 400

Ile Thr Gly Leu Ser
            405

<210> SEQ ID NO 21
<211> LENGTH: 705
<212> TYPE: PRT
<213> ORGANISM: Artificial Sequence
<220> FEATURE:
<223> OTHER INFORMATION: EGFR Isoform 3

<400> SEQUENCE: 21

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

```
Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
        130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480
```

-continued

```
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
        515                 520                 525
Val Ser Arg Gly Arg Glu Cys Val Asp Lys Cys Asn Leu Leu Glu Gly
    530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
        595                 600                 605
Lys Tyr Ala Asp Ala Gly His Val Cys His Leu Cys His Pro Asn Cys
    610                 615                 620
Thr Tyr Gly Pro Gly Asn Glu Ser Leu Lys Ala Met Leu Phe Cys Leu
625                 630                 635                 640
Phe Lys Leu Ser Ser Cys Asn Gln Ser Asn Asp Gly Ser Val Ser His
                645                 650                 655
Gln Ser Gly Ser Pro Ala Ala Gln Glu Ser Cys Leu Gly Trp Ile Pro
            660                 665                 670
Ser Leu Leu Pro Ser Glu Phe Gln Leu Gly Trp Gly Cys Ser His
        675                 680                 685
Leu His Ala Trp Pro Ser Ala Ser Val Ile Ile Thr Ala Ser Ser Cys
    690                 695                 700
His
705

<210> SEQ ID NO 22
<211> LENGTH: 628
<212> TYPE: PRT
<213> ORGANISM: Artificial Sequence
<220> FEATURE:
<223> OTHER INFORMATION: EGFR Isoform 4

<400> SEQUENCE: 22

Met Arg Pro Ser Gly Thr Ala Gly Ala Ala Leu Leu Ala Leu Leu Ala
1               5                   10                  15
Ala Leu Cys Pro Ala Ser Arg Ala Leu Glu Glu Lys Lys Val Cys Gln
            20                  25                  30
Gly Thr Ser Asn Lys Leu Thr Gln Leu Gly Thr Phe Glu Asp His Phe
        35                  40                  45
Leu Ser Leu Gln Arg Met Phe Asn Asn Cys Glu Val Val Leu Gly Asn
    50                  55                  60
Leu Glu Ile Thr Tyr Val Gln Arg Asn Tyr Asp Leu Ser Phe Leu Lys
65                  70                  75                  80
Thr Ile Gln Glu Val Ala Gly Tyr Val Leu Ile Ala Leu Asn Thr Val
                85                  90                  95
Glu Arg Ile Pro Leu Glu Asn Leu Gln Ile Ile Arg Gly Asn Met Tyr
            100                 105                 110
Tyr Glu Asn Ser Tyr Ala Leu Ala Val Leu Ser Asn Tyr Asp Ala Asn
        115                 120                 125
```

-continued

```
Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
            165                 170                 175

Ser Met Asp Phe Gln Asn His Leu Gly Ser Cys Gln Lys Cys Asp Pro
        180                 185                 190

Ser Cys Pro Asn Gly Ser Cys Trp Gly Ala Gly Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
            245                 250                 255

Glu Ala Thr Cys Lys Asp Thr Cys Pro Pro Leu Met Leu Tyr Asn Pro
        260                 265                 270

Thr Thr Tyr Gln Met Asp Val Asn Pro Glu Gly Lys Tyr Ser Phe Gly
    275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
            325                 330                 335

Cys Asn Gly Ile Gly Ile Gly Glu Phe Lys Asp Ser Leu Ser Ile Asn
        340                 345                 350

Ala Thr Asn Ile Lys His Phe Lys Asn Cys Thr Ser Ile Ser Gly Asp
    355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
            405                 410                 415

Leu His Ala Phe Glu Asn Leu Glu Ile Ile Arg Gly Arg Thr Lys Gln
        420                 425                 430

His Gly Gln Phe Ser Leu Ala Val Val Ser Leu Asn Ile Thr Ser Leu
    435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
            485                 490                 495

Asn Ser Cys Lys Ala Thr Gly Gln Val Cys His Ala Leu Cys Ser Pro
        500                 505                 510

Glu Gly Cys Trp Gly Pro Glu Pro Arg Asp Cys Val Ser Cys Arg Asn
    515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
```

```
545             550             555             560
Glu Cys Leu Pro Gln Ala Met Asn Ile Thr Cys Thr Gly Arg Gly Pro
                565             570             575

Asp Asn Cys Ile Gln Cys Ala His Tyr Ile Asp Gly Pro His Cys Val
            580             585             590

Lys Thr Cys Pro Ala Gly Val Met Gly Glu Asn Asn Thr Leu Val Trp
        595             600             605

Lys Tyr Ala Asp Ala Gly His Val Cys His Leu Cys His Pro Asn Cys
    610             615             620

Thr Tyr Gly Ser
625

<210> SEQ ID NO 23
<211> LENGTH: 335
<212> TYPE: PRT
<213> ORGANISM: Artificial Sequence
<220> FEATURE:
<223> OTHER INFORMATION: EGFRt #1

<400> SEQUENCE: 23

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
                20                  25                  30

Ser Gly Asp Leu His Ile Leu Pro Val Ala Phe Arg Gly Asp Ser Phe
            35                  40                  45

Thr His Thr Pro Pro Leu Asp Pro Gln Glu Leu Asp Ile Leu Lys Thr
        50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
```

```
                275                 280                 285
Pro Asn Cys Thr Tyr Gly Cys Thr Gly Pro Gly Leu Glu Gly Cys Pro
    290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335

<210> SEQ ID NO 24
<211> LENGTH: 338
<212> TYPE: PRT
<213> ORGANISM: Artificial Sequence
<220> FEATURE:
<223> OTHER INFORMATION: EGFRt #2

<400> SEQUENCE: 24

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
    290                 295                 300

Thr Asn Gly Pro Lys Ile Pro Ser Ile Ala Thr Gly Met Val Gly Ala
```

```
                305                 310                 315                 320
Leu Leu Leu Leu Leu Val Val Ala Leu Gly Ile Gly Leu Phe Met Arg
                325                 330                 335
Arg Arg

<210> SEQ ID NO 25
<211> LENGTH: 6
<212> TYPE: PRT
<213> ORGANISM: Artificial Sequence
<220> FEATURE:
<223> OTHER INFORMATION: Juxtamembrane Domain #5

<400> SEQUENCE: 25

Lys Ser Gly Ser Gly Ser
1               5

<210> SEQ ID NO 26
<211> LENGTH: 4
<212> TYPE: PRT
<213> ORGANISM: Artificial Sequence
<220> FEATURE:
<223> OTHER INFORMATION: Juxtamembrane Domain #7

<400> SEQUENCE: 26

Lys Arg Ser Asp
1

<210> SEQ ID NO 27
<211> LENGTH: 5
<212> TYPE: PRT
<213> ORGANISM: Artificial Sequence
<220> FEATURE:
<223> OTHER INFORMATION: Juxtamembrane Domain #8

<400> SEQUENCE: 27

Lys Arg Ser Asp Lys
1               5

<210> SEQ ID NO 28
<211> LENGTH: 5
<212> TYPE: PRT
<213> ORGANISM: Artificial Sequence
<220> FEATURE:
<223> OTHER INFORMATION: Juxtamembrane Domain #9

<400> SEQUENCE: 28

Ser Gly Gly Gly Gly
1               5

<210> SEQ ID NO 29
<211> LENGTH: 5
<212> TYPE: PRT
<213> ORGANISM: Artificial Sequence
<220> FEATURE:
<223> OTHER INFORMATION: Juxtamembrane Domain #10

<400> SEQUENCE: 29

Ser Gly Ala Gly Gly
1               5

<210> SEQ ID NO 30
<211> LENGTH: 5
<212> TYPE: PRT
<213> ORGANISM: Artificial Sequence
<220> FEATURE:
<223> OTHER INFORMATION: Juxtamembrane Domain #11
```

```
<400> SEQUENCE: 30

Lys Arg Ala Asp Lys
1               5

<210> SEQ ID NO 31
<211> LENGTH: 14
<212> TYPE: PRT
<213> ORGANISM: Artificial Sequence
<220> FEATURE:
<223> OTHER INFORMATION: Juxtamembrane Domain #12

<400> SEQUENCE: 31

Arg Arg Arg Ser Gly Gly Gly Gly Ser Gly Gly Gly Gly Ser
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Juxtamembrane Domain #13

<400> SEQUENCE: 32

Ser Gly Gly Gly Gly Ser Gly Gly Gly Gly Ser
1               5                   10

<210> SEQ ID NO 33
<211> LENGTH: 7
<212> TYPE: PRT
<213> ORGANISM: Artificial Sequence
<220> FEATURE:
<223> OTHER INFORMATION: Juxtamembrane Domain #14

<400> SEQUENCE: 33

Gly Gly Gly Gly Ser Asn Asn
1               5

<210> SEQ ID NO 34
<211> LENGTH: 9
<212> TYPE: PRT
<213> ORGANISM: Artificial Sequence
<220> FEATURE:
<223> OTHER INFORMATION: Juxtamembrane Domain #15

<400> SEQUENCE: 34

Arg Arg Arg His Ile Val Arg Lys Arg
1               5

<210> SEQ ID NO 35
<211> LENGTH: 8
<212> TYPE: PRT
<213> ORGANISM: Artificial Sequence
<220> FEATURE:
<223> OTHER INFORMATION: Juxtamembrane Domain #16

<400> SEQUENCE: 35

Arg Arg Arg His Ile Val Arg Lys
1               5

<210> SEQ ID NO 36
<211> LENGTH: 7
<212> TYPE: PRT
<213> ORGANISM: Artificial Sequence
<220> FEATURE:
<223> OTHER INFORMATION: Juxtamembrane Domain #17
```

-continued

```
<400> SEQUENCE: 36

Arg Arg Arg His Ile Val Arg
1               5

<210> SEQ ID NO 37
<211> LENGTH: 6
<212> TYPE: PRT
<213> ORGANISM: Artificial Sequence
<220> FEATURE:
<223> OTHER INFORMATION: Juxtamembrane Domain #18

<400> SEQUENCE: 37

Arg Arg Arg His Ile Val
1               5

<210> SEQ ID NO 38
<211> LENGTH: 5
<212> TYPE: PRT
<213> ORGANISM: Artificial Sequence
<220> FEATURE:
<223> OTHER INFORMATION: Juxtamembrane Domain #19

<400> SEQUENCE: 38

Arg Arg Arg His Ile
1               5

<210> SEQ ID NO 39
<211> LENGTH: 4
<212> TYPE: PRT
<213> ORGANISM: Artificial Sequence
<220> FEATURE:
<223> OTHER INFORMATION: Juxtamembrane Domain #20

<400> SEQUENCE: 39

Arg Arg Arg His
1

<210> SEQ ID NO 40
<211> LENGTH: 5
<212> TYPE: PRT
<213> ORGANISM: Artificial Sequence
<220> FEATURE:
<223> OTHER INFORMATION: Linker

<400> SEQUENCE: 40

Gly Gly Gly Ser Gly
1               5

<210> SEQ ID NO 41
<211> LENGTH: 353
<212> TYPE: PRT
<213> ORGANISM: Artificial Sequence
<220> FEATURE:
<223> OTHER INFORMATION: immunoglobulin heavy constant alpha 1

<400> SEQUENCE: 41

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60
```

```
Thr Thr Ser Ser Gln Leu Thr Leu Pro Ala Thr Gln Cys Leu Ala Gly
 65                  70                  75                  80

Lys Ser Val Thr Cys His Val Lys His Tyr Thr Asn Pro Ser Gln Asp
                 85                  90                  95

Val Thr Val Pro Cys Pro Val Pro Ser Thr Pro Pro Thr Pro Ser Pro
                100                 105                 110

Ser Thr Pro Pro Thr Pro Ser Pro Ser Cys Cys His Pro Arg Leu Ser
                115                 120                 125

Leu His Arg Pro Ala Leu Glu Asp Leu Leu Leu Gly Ser Glu Ala Asn
            130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
                180                 185                 190

Ala Glu Pro Trp Asn His Gly Lys Thr Phe Thr Cys Thr Ala Ala Tyr
                195                 200                 205

Pro Glu Ser Lys Thr Pro Leu Thr Ala Thr Leu Ser Lys Ser Gly Asn
            210                 215                 220

Thr Phe Arg Pro Glu Val His Leu Leu Pro Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
                260                 265                 270

Arg Glu Lys Tyr Leu Thr Trp Ala Ser Arg Gln Glu Pro Ser Gln Gly
            275                 280                 285

Thr Thr Thr Phe Ala Val Thr Ser Ile Leu Arg Val Ala Ala Glu Asp
            290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
                340                 345                 350

Tyr

<210> SEQ ID NO 42
<211> LENGTH: 340
<212> TYPE: PRT
<213> ORGANISM: Artificial Sequence
<220> FEATURE:
<223> OTHER INFORMATION: immunoglobulin heavy constant alpha 2

<400> SEQUENCE: 42

Ala Ser Pro Thr Ser Pro Lys Val Phe Pro Leu Ser Leu Asp Ser Thr
  1               5                  10                  15

Pro Gln Asp Gly Asn Val Val Ala Cys Leu Val Gln Gly Phe Phe
                 20                  25                  30

Pro Gln Glu Pro Leu Ser Val Thr Trp Ser Glu Ser Gly Gln Asn Val
             35                  40                  45

Thr Ala Arg Asn Phe Pro Pro Ser Gln Asp Ala Ser Gly Asp Leu Tyr
 50                  55                  60

Thr Thr Ser Ser Gln Leu Thr Leu Pro Ala Thr Gln Cys Pro Asp Gly
```

```
                65                  70                  75                  80
Lys Ser Val Thr Cys His Val Lys His Tyr Thr Asn Ser Ser Gln Asp
                    85                  90                  95
Val Thr Val Pro Cys Arg Val Pro Pro Pro Cys Cys His Pro
                100                 105                 110
Arg Leu Ser Leu His Arg Pro Ala Leu Glu Asp Leu Leu Gly Ser
                115                 120                 125
Glu Ala Asn Leu Thr Cys Thr Leu Thr Gly Leu Arg Asp Ala Ser Gly
            130                 135                 140
Ala Thr Phe Thr Trp Thr Pro Ser Ser Gly Lys Ser Ala Val Gln Gly
145                 150                 155                 160
Pro Pro Glu Arg Asp Leu Cys Gly Cys Tyr Ser Val Ser Ser Val Leu
                165                 170                 175
Pro Gly Cys Ala Gln Pro Trp Asn His Gly Glu Thr Phe Thr Cys Thr
                180                 185                 190
Ala Ala His Pro Glu Leu Lys Thr Pro Leu Thr Ala Asn Ile Thr Lys
                195                 200                 205
Ser Gly Asn Thr Phe Arg Pro Glu Val His Leu Leu Pro Pro Pro Ser
            210                 215                 220
Glu Glu Leu Ala Leu Asn Glu Leu Val Thr Leu Thr Cys Leu Ala Arg
225                 230                 235                 240
Gly Phe Ser Pro Lys Asp Val Leu Val Arg Trp Leu Gln Gly Ser Gln
                245                 250                 255
Glu Leu Pro Arg Glu Lys Tyr Leu Thr Trp Ala Ser Arg Gln Glu Pro
                260                 265                 270
Ser Gln Gly Thr Thr Thr Tyr Ala Val Thr Ser Ile Leu Arg Val Ala
            275                 280                 285
Ala Glu Asp Trp Lys Lys Gly Glu Thr Phe Ser Cys Met Val Gly His
            290                 295                 300
Glu Ala Leu Pro Leu Ala Phe Thr Gln Lys Thr Ile Asp Arg Met Ala
305                 310                 315                 320
Gly Lys Pro Thr His Ile Asn Val Ser Val Val Met Ala Glu Ala Asp
                325                 330                 335
Gly Thr Cys Tyr
            340

<210> SEQ ID NO 43
<211> LENGTH: 330
<212> TYPE: PRT
<213> ORGANISM: Artificial Sequence
<220> FEATURE:
<223> OTHER INFORMATION: immunoglobulin gamma 2A chain C region

<400> SEQUENCE: 43

Ala Lys Thr Thr Ala Pro Ser Val Tyr Pro Leu Ala Pro Val Cys Gly
1               5                   10                  15
Asp Thr Thr Gly Ser Ser Val Thr Leu Gly Cys Leu Val Lys Gly Tyr
                20                  25                  30
Phe Pro Glu Pro Val Thr Leu Thr Trp Asn Ser Gly Ser Leu Ser Ser
            35                  40                  45
Gly Val His Thr Phe Pro Ala Val Leu Gln Ser Asp Leu Tyr Thr Leu
        50                  55                  60
Ser Ser Ser Val Thr Val Thr Ser Ser Thr Trp Pro Ser Gln Ser Ile
65                  70                  75                  80
Thr Cys Asn Val Ala His Pro Ala Ser Ser Thr Lys Val Asp Lys Lys
```

85                  90                  95

Ile Glu Pro Arg Gly Pro Thr Ile Lys Pro Cys Pro Cys Lys Cys
                100                 105                 110

Pro Ala Pro Asn Leu Leu Gly Gly Pro Ser Val Phe Ile Phe Pro Pro
                115                 120                 125

Lys Ile Lys Asp Val Leu Met Ile Ser Leu Ser Pro Ile Val Thr Cys
            130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
                180                 185                 190

His Gln Asp Trp Met Ser Gly Lys Glu Phe Lys Cys Lys Val Asn Asn
            195                 200                 205

Lys Asp Leu Pro Ala Pro Ile Glu Arg Thr Ile Ser Lys Pro Lys Gly
        210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
                260                 265                 270

Asn Tyr Lys Asn Thr Glu Pro Val Leu Asp Ser Asp Gly Ser Tyr Phe
            275                 280                 285

Met Tyr Ser Lys Leu Arg Val Glu Lys Lys Asn Trp Val Glu Arg Asn
        290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 44
<211> LENGTH: 330
<212> TYPE: PRT
<213> ORGANISM: Artificial Sequence
<220> FEATURE:
<223> OTHER INFORMATION: immunoglobulin heavy constant gamma 1

<400> SEQUENCE: 44

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro

```
                115                 120                 125
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 45
<211> LENGTH: 326
<212> TYPE: PRT
<213> ORGANISM: Artificial Sequence
<220> FEATURE:
<223> OTHER INFORMATION: immunoglobulin heavy constant gamma 2

<400> SEQUENCE: 45

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
```

```
                145                 150                 155                 160
Val Glu Val His Asn Ala Lys Thr Lys Pro Arg Glu Glu Gln Phe Asn
                        165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
                195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
                275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 46
<211> LENGTH: 377
<212> TYPE: PRT
<213> ORGANISM: Artificial Sequence
<220> FEATURE:
<223> OTHER INFORMATION: immunoglobulin heavy constant gamma 3

<400> SEQUENCE: 46

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
                100                 105                 110

Arg Cys Pro Glu Pro Lys Ser Cys Asp Thr Pro Pro Cys Pro Arg
            115                 120                 125

Cys Pro Glu Pro Lys Ser Cys Asp Thr Pro Pro Cys Pro Arg Cys
        130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
```

```
            180                 185                 190
Val Val Asp Val Ser His Glu Asp Pro Glu Val Gln Phe Lys Trp Tyr
            195                 200                 205
Val Asp Gly Val Glu Val His Asn Ala Lys Thr Lys Pro Arg Glu Glu
            210                 215                 220
Gln Tyr Asn Ser Thr Phe Arg Val Val Ser Val Leu Thr Val Leu His
225                 230                 235                 240
Gln Asp Trp Leu Asn Gly Lys Glu Tyr Lys Cys Lys Val Ser Asn Lys
            245                 250                 255
Ala Leu Pro Ala Pro Ile Glu Lys Thr Ile Ser Lys Thr Lys Gly Gln
            260                 265                 270
Pro Arg Glu Pro Gln Val Tyr Thr Leu Pro Pro Ser Arg Glu Glu Met
            275                 280                 285
Thr Lys Asn Gln Val Ser Leu Thr Cys Leu Val Lys Gly Phe Tyr Pro
            290                 295                 300
Ser Asp Ile Ala Val Glu Trp Glu Ser Ser Gly Gln Pro Glu Asn Asn
305                 310                 315                 320
Tyr Asn Thr Thr Pro Pro Met Leu Asp Ser Asp Gly Ser Phe Phe Leu
            325                 330                 335
Tyr Ser Lys Leu Thr Val Asp Lys Ser Arg Trp Gln Gln Gly Asn Ile
            340                 345                 350
Phe Ser Cys Ser Val Met His Glu Ala Leu His Asn Arg Phe Thr Gln
            355                 360                 365
Lys Ser Leu Ser Leu Ser Pro Gly Lys
            370                 375

<210> SEQ ID NO 47
<211> LENGTH: 327
<212> TYPE: PRT
<213> ORGANISM: Artificial Sequence
<220> FEATURE:
<223> OTHER INFORMATION: immunoglobulin heavy constant gamma 4

<400> SEQUENCE: 47

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
            50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Ser Cys Pro Ala Pro
            100                 105                 110
Glu Phe Leu Gly Gly Pro Ser Val Phe Leu Phe Pro Pro Lys Pro Lys
            115                 120                 125
Asp Thr Leu Met Ile Ser Arg Thr Pro Glu Val Thr Cys Val Val Val
            130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
```

```
              165                 170                 175
Asn Ser Thr Tyr Arg Val Val Ser Val Leu Thr Val Leu His Gln Asp
                180                 185                 190
Trp Leu Asn Gly Lys Glu Tyr Lys Cys Lys Val Ser Asn Lys Gly Leu
                195                 200                 205
Pro Ser Ser Ile Glu Lys Thr Ile Ser Lys Ala Lys Gly Gln Pro Arg
            210                 215                 220
Glu Pro Gln Val Tyr Thr Leu Pro Pro Ser Gln Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
                260                 265                 270
Thr Thr Pro Pro Val Leu Asp Ser Asp Gly Ser Phe Phe Leu Tyr Ser
            275                 280                 285
Arg Leu Thr Val Asp Lys Ser Arg Trp Gln Glu Gly Asn Val Phe Ser
            290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 48
<211> LENGTH: 384
<212> TYPE: PRT
<213> ORGANISM: Artificial Sequence
<220> FEATURE:
<223> OTHER INFORMATION: immunoglobulin heavy constant delta

<400> SEQUENCE: 48

Ala Pro Thr Lys Ala Pro Asp Val Phe Pro Ile Ile Ser Gly Cys Arg
1               5                  10                  15
His Pro Lys Asp Asn Ser Pro Val Val Leu Ala Cys Leu Ile Thr Gly
                20                  25                  30
Tyr His Pro Thr Ser Val Thr Val Thr Trp Tyr Met Gly Thr Gln Ser
            35                  40                  45
Gln Pro Gln Arg Thr Phe Pro Glu Ile Gln Arg Arg Asp Ser Tyr Tyr
        50                  55                  60
Met Thr Ser Ser Gln Leu Ser Thr Pro Leu Gln Gln Trp Arg Gln Gly
65              70                  75                  80
Glu Tyr Lys Cys Val Val Gln His Thr Ala Ser Lys Ser Lys Lys Glu
                85                  90                  95
Ile Phe Arg Trp Pro Glu Ser Pro Lys Ala Gln Ala Ser Ser Val Pro
                100                 105                 110
Thr Ala Gln Pro Gln Ala Glu Gly Ser Leu Ala Lys Ala Thr Thr Ala
            115                 120                 125
Pro Ala Thr Thr Arg Asn Thr Gly Arg Gly Gly Glu Glu Lys Lys Lys
            130                 135                 140
Glu Lys Glu Lys Glu Glu Gln Glu Glu Arg Glu Thr Lys Thr Pro Glu
145                 150                 155                 160
Cys Pro Ser His Thr Gln Pro Leu Gly Val Tyr Leu Leu Thr Pro Ala
                165                 170                 175
Val Gln Asp Leu Trp Leu Arg Asp Lys Ala Thr Phe Thr Cys Phe Val
                180                 185                 190
Val Gly Ser Asp Leu Lys Asp Ala His Leu Thr Trp Glu Val Ala Gly
```

```
                195                 200                 205
Lys Val Pro Thr Gly Gly Val Glu Gly Leu Leu Glu Arg His Ser
    210                 215                 220
Asn Gly Ser Gln Ser Gln His Ser Arg Leu Thr Leu Pro Arg Ser Leu
225                 230                 235                 240
Trp Asn Ala Gly Thr Ser Val Thr Cys Thr Leu Asn His Pro Ser Leu
            245                 250                 255
Pro Pro Gln Arg Leu Met Ala Leu Arg Glu Pro Ala Ala Gln Ala Pro
                260                 265                 270
Val Lys Leu Ser Leu Asn Leu Leu Ala Ser Ser Asp Pro Pro Glu Ala
            275                 280                 285
Ala Ser Trp Leu Leu Cys Glu Val Ser Gly Phe Ser Pro Pro Asn Ile
290                 295                 300
Leu Leu Met Trp Leu Glu Asp Gln Arg Glu Val Asn Thr Ser Gly Phe
305                 310                 315                 320
Ala Pro Ala Arg Pro Pro Gln Pro Arg Ser Thr Thr Phe Trp Ala
            325                 330                 335
Trp Ser Val Leu Arg Val Pro Ala Pro Pro Ser Pro Gln Pro Ala Thr
                340                 345                 350
Tyr Thr Cys Val Val Ser His Glu Asp Ser Arg Thr Leu Leu Asn Ala
            355                 360                 365
Ser Arg Ser Leu Glu Val Ser Tyr Val Thr Asp His Gly Pro Met Lys
370                 375                 380
```

<210> SEQ ID NO 49
<211> LENGTH: 428
<212> TYPE: PRT
<213> ORGANISM: Artificial Sequence
<220> FEATURE:
<223> OTHER INFORMATION: immunoglobulin heavy constant chain epsilon

<400> SEQUENCE: 49

```
Ala Ser Thr Gln Ser Pro Ser Val Phe Pro Leu Thr Arg Cys Cys Lys
1               5                   10                  15
Asn Ile Pro Ser Asn Ala Thr Ser Val Thr Leu Gly Cys Leu Ala Thr
                20                  25                  30
Gly Tyr Phe Pro Glu Pro Val Met Val Thr Trp Asp Thr Gly Ser Leu
            35                  40                  45
Asn Gly Thr Thr Met Thr Leu Pro Ala Thr Thr Leu Thr Leu Ser Gly
    50                  55                  60
His Tyr Ala Thr Ile Ser Leu Leu Thr Val Ser Gly Ala Trp Ala Lys
65                  70                  75                  80
Gln Met Phe Thr Cys Arg Val Ala His Thr Pro Ser Ser Thr Asp Trp
                85                  90                  95
Val Asp Asn Lys Thr Phe Ser Val Cys Ser Arg Asp Phe Thr Pro Pro
                100                 105                 110
Thr Val Lys Ile Leu Gln Ser Ser Cys Asp Gly Gly Gly His Phe Pro
            115                 120                 125
Pro Thr Ile Gln Leu Leu Cys Leu Val Ser Gly Tyr Thr Pro Gly Thr
        130                 135                 140
Ile Asn Ile Thr Trp Leu Glu Asp Gly Gln Val Met Asp Val Asp Leu
145                 150                 155                 160
Ser Thr Ala Ser Thr Thr Gln Glu Gly Glu Leu Ala Ser Thr Gln Ser
                165                 170                 175
Glu Leu Thr Leu Ser Gln Lys His Trp Leu Ser Asp Arg Thr Tyr Thr
```

```
                 180                 185                 190
Cys Gln Val Thr Tyr Gln Gly His Thr Phe Glu Asp Ser Thr Lys Lys
            195                 200                 205
Cys Ala Asp Ser Asn Pro Arg Gly Val Ser Ala Tyr Leu Ser Arg Pro
            210                 215                 220
Ser Pro Phe Asp Leu Phe Ile Arg Lys Ser Pro Thr Ile Thr Cys Leu
225                 230                 235                 240
Val Val Asp Leu Ala Pro Ser Lys Gly Thr Val Asn Leu Thr Trp Ser
            245                 250                 255
Arg Ala Ser Gly Lys Pro Val Asn His Ser Thr Arg Lys Glu Glu Lys
            260                 265                 270
Gln Arg Asn Gly Thr Leu Thr Val Thr Ser Thr Leu Pro Val Gly Thr
            275                 280                 285
Arg Asp Trp Ile Glu Gly Glu Thr Tyr Gln Cys Arg Val Thr His Pro
            290                 295                 300
His Leu Pro Arg Ala Leu Met Arg Ser Thr Thr Lys Thr Ser Gly Pro
305                 310                 315                 320
Arg Ala Ala Pro Glu Val Tyr Ala Phe Ala Thr Pro Glu Trp Pro Gly
            325                 330                 335
Ser Arg Asp Lys Arg Thr Leu Ala Cys Leu Ile Gln Asn Phe Met Pro
            340                 345                 350
Glu Asp Ile Ser Val Gln Trp Leu His Asn Glu Val Gln Leu Pro Asp
            355                 360                 365
Ala Arg His Ser Thr Thr Gln Pro Arg Lys Thr Lys Gly Ser Gly Phe
            370                 375                 380
Phe Val Phe Ser Arg Leu Glu Val Thr Arg Ala Glu Trp Glu Gln Lys
385                 390                 395                 400
Asp Glu Phe Ile Cys Arg Ala Val His Glu Ala Ala Ser Pro Ser Gln
            405                 410                 415
Thr Val Gln Arg Ala Val Ser Val Asn Pro Gly Lys
            420                 425

<210> SEQ ID NO 50
<211> LENGTH: 453
<212> TYPE: PRT
<213> ORGANISM: Artificial Sequence
<220> FEATURE:
<223> OTHER INFORMATION: immunoglobulin heavy constant mu

<400> SEQUENCE: 50

Gly Ser Ala Ser Ala Pro Thr Leu Phe Pro Leu Val Ser Cys Glu Asn
1               5                   10                  15
Ser Pro Ser Asp Thr Ser Ser Val Ala Val Gly Cys Leu Ala Gln Asp
            20                  25                  30
Phe Leu Pro Asp Ser Ile Thr Phe Ser Trp Lys Tyr Lys Asn Asn Ser
            35                  40                  45
Asp Ile Ser Ser Thr Arg Gly Phe Pro Ser Val Leu Arg Gly Gly Lys
        50                  55                  60
Tyr Ala Ala Thr Ser Gln Val Leu Leu Pro Ser Lys Asp Val Met Gln
65                  70                  75                  80
Gly Thr Asp Glu His Val Val Cys Lys Val Gln His Pro Asn Gly Asn
                85                  90                  95
Lys Glu Lys Asn Val Pro Leu Pro Val Ile Ala Glu Leu Pro Pro Lys
            100                 105                 110
Val Ser Val Phe Val Pro Pro Arg Asp Gly Phe Phe Gly Asn Pro Arg
```

```
            115                 120                 125
Lys Ser Lys Leu Ile Cys Gln Ala Thr Gly Phe Ser Pro Arg Gln Ile
    130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
    210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
    290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
        355                 360                 365

Gly Gln Pro Leu Ser Pro Glu Lys Tyr Val Thr Ser Ala Pro Met Pro
    370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Val Ala
                405                 410                 415

His Glu Ala Leu Pro Asn Arg Val Thr Glu Arg Thr Val Asp Lys Ser
            420                 425                 430

Thr Gly Lys Pro Thr Leu Tyr Asn Val Ser Leu Val Met Ser Asp Thr
        435                 440                 445

Ala Gly Thr Cys Tyr
    450

<210> SEQ ID NO 51
<211> LENGTH: 9
<212> TYPE: PRT
<213> ORGANISM: Artificial Sequence
<220> FEATURE:
<223> OTHER INFORMATION: Spacer

<400> SEQUENCE: 51

Lys Pro Cys Pro Pro Cys Lys Cys Pro
1               5
```

```
<210> SEQ ID NO 52
<211> LENGTH: 24
<212> TYPE: PRT
<213> ORGANISM: Artificial Sequence
<220> FEATURE:
<223> OTHER INFORMATION: EGFR Signal Peptide

<400> SEQUENCE: 52

Met Arg Pro Ser Gly Thr Ala Gly Ala Ala Leu Leu Ala Leu Leu Ala
1               5                   10                  15

Ala Leu Cys Pro Ala Ser Arg Ala
            20

<210> SEQ ID NO 53
<211> LENGTH: 22
<212> TYPE: PRT
<213> ORGANISM: Artificial Sequence
<220> FEATURE:
<223> OTHER INFORMATION: GM-CSF Signal Peptide

<400> SEQUENCE: 53

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 54
<211> LENGTH: 20
<212> TYPE: PRT
<213> ORGANISM: Artificial Sequence
<220> FEATURE:
<223> OTHER INFORMATION: Human Ig Kappa Signal Peptide

<400> SEQUENCE: 54

Met Val Leu Gln Thr Gln Val Phe Ile Ser Leu Leu Leu Trp Ile Ser
1               5                   10                  15

Gly Ala Tyr Gly
            20

<210> SEQ ID NO 55
<211> LENGTH: 16
<212> TYPE: PRT
<213> ORGANISM: Artificial Sequence
<220> FEATURE:
<223> OTHER INFORMATION: Human CD33 Signal Peptide

<400> SEQUENCE: 55

Met Pro Leu Leu Leu Leu Leu Pro Leu Leu Trp Ala Gly Ala Leu Ala
1               5                   10                  15

<210> SEQ ID NO 56
<211> LENGTH: 121
<212> TYPE: PRT
<213> ORGANISM: Artificial Sequence
<220> FEATURE:
<223> OTHER INFORMATION: R12 VH

<400> SEQUENCE: 56

Gln Glu Gln Leu Val Glu Ser Gly Gly Arg Leu Val Thr Pro Gly Gly
1               5                   10                  15

Ser Leu Thr Leu Ser Cys Lys Ala Ser Gly Phe Asp Phe Ser Ala Tyr
                20                  25                  30

Tyr Met Ser Trp Val Arg Gln Ala Pro Gly Lys Gly Leu Glu Trp Ile
            35                  40                  45
```

```
Ala Thr Ile Tyr Pro Ser Ser Gly Lys Thr Tyr Tyr Ala Thr Trp Val
 50                  55                  60

Asn Gly Arg Phe Thr Ile Ser Ser Asp Asn Ala Gln Asn Thr Val Asp
 65                  70                  75                  80

Leu Gln Met Asn Ser Leu Thr Ala Ala Asp Arg Ala Thr Tyr Phe Cys
                 85                  90                  95

Ala Arg Asp Ser Tyr Ala Asp Asp Gly Ala Leu Phe Asn Ile Trp Gly
            100                 105                 110

Pro Gly Thr Leu Val Thr Ile Ser Ser
        115                 120

<210> SEQ ID NO 57
<211> LENGTH: 5
<212> TYPE: PRT
<213> ORGANISM: Artificial Sequence
<220> FEATURE:
<223> OTHER INFORMATION: R12 VH CDR1

<400> SEQUENCE: 57

Ala Tyr Tyr Met Ser
1               5

<210> SEQ ID NO 58
<211> LENGTH: 17
<212> TYPE: PRT
<213> ORGANISM: Artificial Sequence
<220> FEATURE:
<223> OTHER INFORMATION: R12 VH CDR2

<400> SEQUENCE: 58

Thr Ile Tyr Pro Ser Ser Gly Lys Thr Tyr Tyr Ala Thr Trp Val Asn
1               5                  10                  15

Gly

<210> SEQ ID NO 59
<211> LENGTH: 12
<212> TYPE: PRT
<213> ORGANISM: Artificial Sequence
<220> FEATURE:
<223> OTHER INFORMATION: R12 VH CDR3

<400> SEQUENCE: 59

Asp Ser Tyr Ala Asp Asp Gly Ala Leu Phe Asn Ile
1               5                  10

<210> SEQ ID NO 60
<211> LENGTH: 112
<212> TYPE: PRT
<213> ORGANISM: Artificial Sequence
<220> FEATURE:
<223> OTHER INFORMATION: R12 VL

<400> SEQUENCE: 60

Glu Leu Val Leu Thr Gln Ser Pro Ser Val Ser Ala Ala Leu Gly Ser
1               5                  10                  15

Pro Ala Lys Ile Thr Cys Thr Leu Ser Ser Ala His Lys Thr Asp Thr
            20                  25                  30

Ile Asp Trp Tyr Gln Gln Leu Gln Gly Glu Ala Pro Arg Tyr Leu Met
        35                  40                  45

Gln Val Gln Ser Asp Gly Ser Tyr Thr Lys Arg Pro Gly Val Pro Asp
    50                  55                  60

Arg Phe Ser Gly Ser Ser Ser Gly Ala Asp Arg Tyr Leu Ile Ile Pro
```

```
                65                  70                  75                  80
Ser Val Gln Ala Asp Asp Glu Ala Asp Tyr Tyr Cys Gly Ala Asp Tyr
                    85                  90                  95

Ile Gly Gly Tyr Val Phe Gly Gly Gly Thr Gln Leu Thr Val Thr Gly
                100                 105                 110
```

<210> SEQ ID NO 61
<211> LENGTH: 12
<212> TYPE: PRT
<213> ORGANISM: Artificial Sequence
<220> FEATURE:
<223> OTHER INFORMATION: R12 VL CDR1

<400> SEQUENCE: 61

```
Thr Leu Ser Ser Ala His Lys Thr Asp Thr Ile Asp
1               5                   10
```

<210> SEQ ID NO 62
<211> LENGTH: 7
<212> TYPE: PRT
<213> ORGANISM: Artificial Sequence
<220> FEATURE:
<223> OTHER INFORMATION: R12 VL CDR2

<400> SEQUENCE: 62

```
Gly Ser Tyr Thr Lys Arg Pro
1               5
```

<210> SEQ ID NO 63
<211> LENGTH: 9
<212> TYPE: PRT
<213> ORGANISM: Artificial Sequence
<220> FEATURE:
<223> OTHER INFORMATION: R12 VL CDR3

<400> SEQUENCE: 63

```
Gly Ala Asp Tyr Ile Gly Gly Tyr Val
1               5
```

<210> SEQ ID NO 64
<211> LENGTH: 5
<212> TYPE: PRT
<213> ORGANISM: Artificial Sequence
<220> FEATURE:
<223> OTHER INFORMATION: Gly/Ser Linker #1
<220> FEATURE:
<221> NAME/KEY: misc_feature
<222> LOCATION: (1)..(5)
<223> OTHER INFORMATION: wherein the sequence can be repeated by an
      integer greater than one

<400> SEQUENCE: 64

```
Gly Gly Gly Ser Gly
1               5
```

<210> SEQ ID NO 65
<211> LENGTH: 5
<212> TYPE: PRT
<213> ORGANISM: Artificial Sequence
<220> FEATURE:
<223> OTHER INFORMATION: Gly/Ser Linker #2
<220> FEATURE:
<221> NAME/KEY: misc_feature
<222> LOCATION: (1)..(5)
<223> OTHER INFORMATION: wherein the sequence can be repeated by an
      integer greater than one

<400> SEQUENCE: 65

Gly Gly Gly Gly Ser
1               5

<210> SEQ ID NO 66
<211> LENGTH: 4
<212> TYPE: PRT
<213> ORGANISM: Artificial Sequence
<220> FEATURE:
<223> OTHER INFORMATION: Gly/Ser Linker #3
<220> FEATURE:
<221> NAME/KEY: misc_feature
<222> LOCATION: (1)..(4)
<223> OTHER INFORMATION: wherein the sequence can be repeated by an
      integer greater than one

<400> SEQUENCE: 66

Gly Gly Gly Ser
1

<210> SEQ ID NO 67
<211> LENGTH: 3
<212> TYPE: PRT
<213> ORGANISM: Artificial Sequence
<220> FEATURE:
<223> OTHER INFORMATION: Gly/Ser Linker #4
<220> FEATURE:
<221> NAME/KEY: misc_feature
<222> LOCATION: (1)..(3)
<223> OTHER INFORMATION: wherein the sequence can be repeated by an
      integer greater than one

<400> SEQUENCE: 67

Gly Gly Ser
1

<210> SEQ ID NO 68
<211> LENGTH: 6
<212> TYPE: PRT
<213> ORGANISM: Artificial Sequence
<220> FEATURE:
<223> OTHER INFORMATION: Gly/Ser Linker #5

<400> SEQUENCE: 68

Gly Ser Gly Ser Gly Ser
1               5

<210> SEQ ID NO 69
<211> LENGTH: 5
<212> TYPE: PRT
<213> ORGANISM: Artificial Sequence
<220> FEATURE:
<223> OTHER INFORMATION: Gly/Ser Linker #6

<400> SEQUENCE: 69

Gly Gly Ser Gly Gly
1               5

<210> SEQ ID NO 70
<211> LENGTH: 7
<212> TYPE: PRT
<213> ORGANISM: Artificial Sequence
<220> FEATURE:
<223> OTHER INFORMATION: Gly/Ser Linker #7

<400> SEQUENCE: 70

Ser Gly Gly Ser Gly Gly Ser
1               5

```
<210> SEQ ID NO 71
<211> LENGTH: 15
<212> TYPE: PRT
<213> ORGANISM: Artificial Sequence
<220> FEATURE:
<223> OTHER INFORMATION: Gly/Ser Linker #8

<400> SEQUENCE: 71

Gly Gly Ser Gly Gly Ser Gly Gly Ser Gly Gly Ser Gly Gly Gly
1               5                   10                  15

<210> SEQ ID NO 72
<211> LENGTH: 16
<212> TYPE: PRT
<213> ORGANISM: Artificial Sequence
<220> FEATURE:
<223> OTHER INFORMATION: Gly/Ser Linker #9

<400> SEQUENCE: 72

Gly Gly Ser Gly Gly Ser Gly Gly Gly Gly Ser Gly Gly Gly Gly Ser
1               5                   10                  15

<210> SEQ ID NO 73
<211> LENGTH: 18
<212> TYPE: PRT
<213> ORGANISM: Artificial Sequence
<220> FEATURE:
<223> OTHER INFORMATION: Gly/Ser Linker #10

<400> SEQUENCE: 73

Gly Gly Ser Gly Gly Ser Gly Gly Ser Gly Gly Ser Gly Gly Ser Gly
1               5                   10                  15

Gly Ser

<210> SEQ ID NO 74
<211> LENGTH: 15
<212> TYPE: PRT
<213> ORGANISM: Artificial Sequence
<220> FEATURE:
<223> OTHER INFORMATION: Gly/Ser Linker #11

<400> SEQUENCE: 74

Gly Gly Gly Gly Ser Gly Gly Gly Gly Ser Gly Gly Gly Gly Ser
1               5                   10                  15
```

CODON-OPTIMIZED NUCLEOTIDE SEQUENCES ENCODING AN AP-1 TRANSCRIPTION FACTOR

CROSS-REFERENCE TO RELATED APPLICATION

This application claims the priority benefit of U.S. Provisional Application No. 63/153,879, filed on Feb. 25, 2021; 63/263,231, filed on Oct. 28, 2021; and 63/309,380, filed on Feb. 11, 2022; each of which is herein incorporated by reference in its entirety.

REFERENCE TO SEQUENCE LISTING SUBMITTED ELECTRONICALLY VIA EFS-WEB

The content of the electronically submitted sequence listing (Name: 4385_0680004_Seqlisting_ST25.txt, Size: 99,323 bytes; and Date of Creation: Feb. 24, 2022) submitted in this application is incorporated herein by reference in its entirety.

FIELD OF THE DISCLOSURE

The presently disclosed subject matter generally relates to polynucleotides, polypeptides, cells, vectors, uses, and kits relating to codon-optimized nucleotide sequences encoding an AP-1 transcription factor.

BACKGROUND OF THE DISCLOSURE

Cancer immunotherapy relies on harnessing T cells—the immune system's primary killers of infected and diseased cells—to attack and kill tumor cells. However, the ability of immune cells to target and kill tumor cells is dampened by the presence of various inhibitors of the immune response that are present within the tumor microenvironment. Therefore, while CAR T cells have had various successes in treating certain cancers (e.g., KYMRIAH™ (tisagenlecleucel, Novartis) and YESCARTA™ (axicabtagene ciloleucel, Kite/Gilead) has been approved by the FDA), challenges remain. For instance, the success of CAR T cell immunotherapy is often limited by the extent of CAR T expansion in a recipient's body, which typically requires a large infusion of cells. Additionally, exhaustion and loss of persistence of the transferred CAR T cells have been observed, leading to loss of clinical efficacy and potential relapse.

Therefore, there remains a need for new and improved treatment options with acceptable safety profile and high efficacy in cancer patients.

BRIEF SUMMARY OF THE DISCLOSURE

Provided herein is a polynucleotide comprising: a) a nucleotide sequence having at least 89%, at least 90%, at least about 95%, at least about 96%, at least about 97%, at least about 98%, at least about 99%, or about 100% sequence identity to the nucleic acid sequence as set forth in SEQ ID NO: 1; b) a nucleotide sequence having at least 90%, at least about 95%, at least about 96%, at least about 97%, at least about 98%, at least about 99%, or about 100% sequence identity to the nucleic acid sequence as set forth in SEQ ID NO: 2; c) a nucleotide sequence having at least about 30%, at least about 40%, at least about 50%, at least about 60%, at least about 70%, at least about 80%, at least about 90%, at least about 95%, at least about 96%, at least about 97%, at least about 98%, at least about 99%, or about 100% sequence identity to the nucleic acid sequence as set forth in SEQ ID NO: 4; d) a nucleotide sequence having at least 79%, at least 80%, at least 81%, at least 82%, at least 83%, at least 84%, at least 85%, at least 86%, at least 87%, at least 88%, at least 89%, at least 90%, at least about 95%, at least about 96%, at least about 97%, at least about 98%, at least about 99%, or about 100% sequence identity to the nucleic acid sequence as set forth in SEQ ID NO: 5; e) a nucleotide sequence having at least 88%, at least 89%, at least 90%, at least about 95%, at least about 96%, at least about 97%, at least about 98%, at least about 99%, or about 100% sequence identity to the nucleic acid sequence as set forth in SEQ ID NO: 6; f) a nucleotide sequence having at least 82%, at least 83%, at least 84%, at least 85%, at least 90%, at least about 95%, at least about 96%, at least about 97%, at least about 98%, at least about 99%, or about 100% sequence identity to the nucleic acid sequence as set forth in SEQ ID NO: 7; g) a nucleotide sequence having at least 90%, at least about 95%, at least about 96%, at least about 97%, at least about 98%, at least about 99%, or about 100% sequence identity to the nucleic acid sequence as set forth in SEQ ID NO: 8; h) a nucleotide sequence having at least 55%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or about 100% sequence identity to the nucleic acid sequence as set forth in SEQ ID NO: 9; or i) a nucleotide sequence having at least 85%, at least 86%, at least 87%, at least 88%, at least 89%, at least about 90%, at least about 95%, at least about 96%, at least about 97%, at least about 98%, at least about 99%, or about 100% sequence identity to the nucleic acid sequence as set forth in SEQ ID NO: 10; wherein the nucleotide sequence encodes an AP-1 transcription factor.

Provided herein is a polynucleotide comprising a nucleotide sequence having at least 89%, at least 90%, at least about 95%, at least about 96%, at least about 97%, at least about 98%, or at least about 99% sequence identity to the nucleic acid sequence as set forth in SEQ ID NO: 1; wherein the nucleotide sequence encodes an AP-1 transcription factor. In certain aspects, the nucleotide sequence comprises the nucleic acid sequence as set forth in SEQ ID NO: 1.

Also provided herein is a polynucleotide comprising a nucleotide sequence having at least 90%, at least about 95%, at least about 96%, at least about 97%, at least about 98%, or at least about 99% sequence identity to the nucleic acid sequence as set forth in SEQ ID NO: 2; wherein the nucleotide sequence encodes an AP-1 transcription factor. In some aspects, the nucleotide sequence comprises the nucleic acid sequence as set forth in SEQ ID NO: 2.

Provided herein is a polynucleotide comprising a nucleotide sequence having at least about 30%, at least about 40%, at least about 50%, at least about 60%, at least about 70%, at least about 80%, at least about 90%, at least about 95%, at least about 96%, at least about 97%, at least about 98%, or at least about 99% sequence identity to the nucleic acid sequence as set forth in SEQ ID NO: 4; wherein the nucleotide sequence encodes an AP-1 transcription factor. In some aspects, the nucleotide sequence comprises the nucleic acid sequence as set forth in SEQ ID NO: 4.

Present disclosure further provides a polynucleotide comprising a nucleotide sequence having at least 79%, at least 80%, at least 81%, at least 82%, at least 83%, at least 84%, at least 85%, at least 86%, at least 87%, at least 88%, at least 89%, at least 90%, at least about 95%, at least about 96%, at least about 97%, at least about 98%, or at least about 99% sequence identity to the nucleic acid sequence as set forth in SEQ ID NO: 5; wherein the nucleotide sequence encodes an AP-1 transcription factor. In certain aspects, the nucleotide sequence comprises the nucleic acid sequence as set forth in SEQ ID NO: 5.

Provided herein is a polynucleotide comprising a nucleotide sequence having at least 88%, at least 89%, at least 90%, at least about 95%, at least about 96%, at least about 97%, at least about 98%, or at least about 99% sequence identity to the nucleic acid sequence as set forth in SEQ ID NO: 6; wherein the nucleotide sequence encodes an AP-1 transcription factor. In some aspects, the nucleotide sequence comprises the nucleic acid sequence as set forth in SEQ ID NO: 6.

Provided herein is a polynucleotide comprising a nucleotide sequence having at least 82%, at least 83%, at least 84%, at least 85%, at least 90%, at least about 95%, at least about 96%, at least about 97%, at least about 98%, or at least about 99% sequence identity to the nucleic acid sequence as set forth in SEQ ID NO: 7; wherein the nucleotide sequence encodes an AP-1 transcription factor. In certain aspects, the nucleotide sequence comprises the nucleic acid sequence as set forth in SEQ ID NO: 7.

Provided herein is a polynucleotide comprising a nucleotide sequence having at least 90%, at least about 95%, at least about 96%, at least about 97%, at least about 98%, or at least about 99% sequence identity to the nucleic acid sequence as set forth in SEQ ID NO: 8; wherein the nucleotide sequence encodes an AP-1 transcription factor. In some aspects, the nucleotide sequence comprises the nucleic acid sequence as set forth in SEQ ID NO: 8.

Provided herein is a polynucleotide comprising a nucleotide sequence having at least 55%, at least about 55%, at least about 60%, at least about 65%, at least about 70%, at least about 75%, at least about 80%, at least about 85%, at least 90%, at least about 95%, at least about 96%, at least about 97%, at least about 98%, or at least about 99% sequence identity to the nucleic acid sequence as set forth in SEQ ID NO: 9; wherein the nucleotide sequence encodes an AP-1 transcription factor. In certain aspects, the nucleotide sequence comprises the nucleic acid sequence as set forth in SEQ ID NO: 9.

Also provided herein is a polynucleotide comprising a nucleotide sequence having at least 85%, at least 86%, at least 87%, at least 88%, at least 89%, at least 90%, at least about 95%, at least about 96%, at least about 97%, at least about 98%, or at least about 99% sequence identity to the nucleic acid sequence as set forth in SEQ ID NO: 10, wherein the nucleotide sequence encoding an AP-1 transcription factor. In some aspects, the nucleotide sequence comprises the nucleic acid sequence as set forth in SEQ ID NO: 10.

In some aspects, the AP-1 transcription factor encoded by any one of the above polynucleotides comprises an amino acid sequence having at least about 90%, at least about 95%, at least about 96%, at least about 97%, at least about 98%, or at least about 99% sequence identity to the sequence as set forth in SEQ ID NO: 13.

In some aspects, a polynucleotide of the present disclosure further comprises a nucleotide sequence encoding a ligand binding protein. In certain aspects, the ligand binding protein comprises a chimeric antigen receptor (CAR), a T cell receptor (TCR), a chimeric antibody-T cell receptor (caTCR), a chimeric signaling receptor (CSR), T cell receptor mimic (TCR mimic), or combinations thereof. In some aspects, the CAR is designed as a standard CAR, a split CAR, an off-switch CAR, an on-switch CAR, a first-generation CAR, a second-generation CAR, a third-generation CAR, or a fourth-generation CAR.

In some aspects, the ligand binding protein comprises an antigen-binding domain, a transmembrane domain, a costimulatory domain, and/or an intracellular signaling domain. In certain aspects, the antigen-binding domain specifically binds an antigen selected from the group consisting of AFP (alpha-fetoprotein), αvβ6 or another integrin, BCMA, Braf, B7-H3, B7-H6, CA9 (carbonic anhydrase 9), CCL-1 (C—C motif chemokine ligand 1), CD5, CD19, CD20, CD21, CD22, CD23, CD24, CD30, CD33, CD38, CD40, CD44, CD44v6, CD44v7/8, CD45, CD47, CD56, CD66e, CD70, CD74, CD79a, CD79b, CD98, CD123, CD138, CD171, CD352, CEA (carcinoembryonic antigen), Claudin 18.2, Claudin 6, c-MET, DLL3 (delta-like protein 3), DLL4, ENPP3 (ectonucleotide pyrophosphatase/phosphodiesterase family member 3), EpCAM, EPG-2 (epithelial glycoprotein 2), EPG-40, ephrinB2, EPHa2 (ephrine receptor A2), ERBB dimers, estrogen receptor, ETBR (endothelin B receptor), FAP-α (fibroblast activation protein α), fetal AchR (fetal acetylcholine receptor), FBP (a folate binding protein), FCRL5, FR-α (folate receptor alpha), GCC (guanyl cyclase C), GD2, GD3, GPC2 (glypican-2), GPC3, gp100 (glycoprotein 100), GPNMB (glycoprotein NMB), GPRC5D (G Protein Coupled Receptor 5D), HER2, HER3, HER4, hepatitis B surface antigen, HLA-A1 (human leukocyte antigen A1), HLA-A2 (human leukocyte antigen A2), HMW-MAA (human high molecular weight-melanoma-associated antigen), IGF1R (insulin-like growth factor 1 receptor), Ig kappa, Ig lambda, IL-22Ra (IL-22 receptor alpha), IL-13Ra2 (IL-13 receptor alpha 2), KDR (kinase insert domain receptor), LI cell adhesion molecule (LI-CAM), Liv-1, LRRC8A (leucine rich repeat containing 8 Family member A), Lewis Y, melanoma-associated antigen (MAGE)-A1, MAGE-A3, MAGE-A6, MART-1 (melan A), murine cytomegalovirus (MCMV), MCSP (melanoma-associated chondroitin sulfate proteoglycan), mesothelin, mucin 1 (MUC1), MUC16, MHC/peptide complexes (e.g., HLA-A complexed with peptides derived from AFP, KRAS, NY-ESO, MAGE-A, and WT1), NCAM (neural cell adhesion molecule), Nectin-4, NKG2D (natural killer group 2 member D) ligands, NY-ESO, oncofetal antigen, PD-1, PD-L1, PRAME (preferentially expressed antigen of melanoma), progesterone receptor, PSA (prostate specific antigen), PSCA (prostate stem cell antigen), PSMA (prostate specific membrane antigen), ROR1, ROR2, SIRPα (signal-regulatory protein alpha), SLIT, SLITRK6 (NTRK-like protein 6), STEAP1 (six transmembrane epithelial antigen of the prostate 1), survivin, TAG72 (tumor-associated glycoprotein 72), TPBG (trophoblast glycoprotein), Trop-2, VEGFR1 (vascular endothelial growth factor receptor 1), VEGFR2, and antigens from HIV, HBV, HCV, HPV, and other pathogens, and any combination thereof.

In some aspects, the antigen-binding domain specifically binds ROR1. In certain aspects, the antigen-binding domain specifically binds GPC2.

In some aspects, the costimulatory domain of a ligand binding protein comprises interleukin-2 receptor (IL-2R), interleukin-12 receptor (IL-12R), IL-7, IL-21, IL-23, IL-15, CD2, CD3, CD4, CD7, CD8, CD27, CD28, CD30, CD40, 4-1BB/CD137, ICOS, lymphocyte function-associated antigen-1 (LFA-1), LIGHT, NKG2C, OX40, DAP10, or any combination thereof. In some aspects, the costimulatory domain comprises a 4-1BB/CD137 costimulatory domain.

In some aspects, the transmembrane domain of a ligand binding protein described herein comprises a transmembrane domain regions of KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKG2D, NKG2C, CD19, or any combination thereof. In certain aspects, the transmembrane domain comprises a CD28 transmembrane domain.

In some aspects, the intracellular signaling domain of a ligand binding domain comprises an intracellular signaling domain region derived from CD3 zeta, FcR gamma, common FcR gamma (FCER1G), Fc gamma RIIa, FcR beta (Fc Epsilon Rib), CD3 gamma, CD3 delta, CD3 epsilon, CD22, CD79a, CD79b, CD278 ("ICOS"), FcεRI, CD66d, CD32, DAP10, DAP12, or any combination thereof. In certain aspects, the intracellular signaling domain comprises a CD3 zeta intracellular signaling domain.

In some aspects, a ligand binding domain that is encoded by a polynucleotide of the present disclosure comprises a TCR, wherein the TCR specifically binds a tumor antigen/MHC complex. In certain aspects, the tumor antigen is derived from AFP, CD19, BCMA, CLL-1, CS1, CD38, CD19, TSHR, CD123, CD22, CD30, CD171, CD33, EGFRvIII, GD2, GD3, Tn Ag, PSMA, ROR1, ROR2, GPC1, GPC2, FLT3, FAP, TAG72, CD44v6, CEA, EPCAM, B7H3, KIT, IL-13Ra2, mesothelin, IL-11Ra, PSCA, PRSS21, VEGFR2, LewisY, CD24, PDGFR-beta, SSEA-4, CD20, folate receptor alpha, ERBB2 (Her2/neu), MUC1, MUC16, EGFR, NCAM, prostase, PAP, ELF2M, Ephrin B2, IGF-I receptor, CAIX, LMP2, gp100, bcr-abl, tyrosinase, EphA2, fucosyl GM1, sLe, GM3, TGS5, HMWMAA, o-acetyl-GD2, folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6,E7, MAGE A1, ETV6-AML, sperm protein 17, XAGE1, Tie 2, MAD-CT-1, MAD-CT-2, Fos-related antigen 1, p53, p53 mutant, prostein, survivin, telomerase, PCTA-1/Galectin 8, MelanA/MART1, Ras mutant (e.g., HRAS, KRAS, NRAS), hTERT, sarcoma translocation breakpoints, ML-IAP, ERG (TMPRSS2 ETS fusion gene), NA17, PAX3, androgen receptor, cyclin B1, MYCN, RhoC, TRP-2, CYP1B1, BORIS, SART3, PAX5, OY-TESL LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, IGLL1, CD2, CD3c, CD4, CD5, CD7, the extracellular portion of the APRIL protein, neoantigen, or any combinations thereof.

In some aspects, the AP-1 transcription factor is linked to the ligand binding protein by a linker. In certain aspects, the linker comprises a cleavable linker. In some aspects, the linker is a P2A linker, a T2A linker, an F2A linker, an E2A linker, a furin cleavage site, or any combination thereof. In certain aspects, the linker comprises an amino acid sequence having at least about 80%, at least about 85%, at least about 90%, at least about 95%, at least about 96%, at least about 97%, at least about 98%, or at least about 99% sequence identity to the amino acid sequence set forth in any one of SEQ ID NOs: 14-18. In some aspects, the linker comprises the amino acid sequence set forth in SEQ ID NO: 14.

In some aspects, a polynucleotide described herein further comprises a nucleic acid sequence encoding a truncated EGFR (EGFRt). In certain aspects, the EGFRt comprises an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 19. In certain aspects, the EGFRt comprises the amino acid sequence set forth in SEQ ID NO: 23 or 24.

In some aspects, the EGFRt is linked to the AP-1 transcription factor and/or the chimeric binding protein by a linker. In certain aspects, the linker comprises a cleavable linker. In some aspects, the linker is a P2A linker, a T2A linker, an F2A linker, an E2A linker, a furin cleavage site, or any combination thereof. In certain aspects, the linker comprises an amino acid sequence having at least about 80%, at least about 85%, at least about 90%, at least about 95%, at least about 96%, at least about 97%, at least about 98%, or at least about 99% sequence identity to the amino acid sequence set forth in any one of SEQ ID NOs: 14-18. In certain aspects, the linker comprises the amino acid sequence set forth in SEQ ID NO: 14.

Provided herein is a vector comprising any of the polynucleotides described herein and a regulatory element. In some aspects, the vector is a polycistronic expression vector. In certain aspects, the regulatory element comprises a promoter. In some aspects, the promoter comprises a d1587rev primer-binding site substituted (MND) promoter, EF1a promoter, ubiquitin promoter, or combinations thereof.

In some aspects, the vector comprises a viral vector, a mammalian vector, or a bacterial vector. In certain aspects, the vector is an adenoviral vector, a lentivirus, a Sendai virus vector, a baculoviral vector, an Epstein Barr viral vector, a papovaviral vector, a vaccinia viral vector, a herpes simplex viral vector, a hybrid vector, or an adeno associated virus (AAV) vector. In some aspects, the vector is a lentivirus.

Also provided herein is a composition comprising a polynucleotide or vector described herein. Present disclosure also provides a kit comprising the polynucleotide, vector, or composition described herein. Provided herein is a polypeptide comprising the AP-1 transcription factor encoded by the polynucleotide, vector, or composition described herein. Present disclosure further provides a set of polypeptides comprising a polypeptide (e.g., AP-1 transcription factor), ligand binding protein encoded by a polynucleotide of the present disclosure, and/or the EGFRt described herein.

Also provided herein is a cell comprising the polynucleotide, vector, composition, polypeptide, or set of polypeptides described herein. In some aspects, the cell comprises an immune cell. In certain aspects, the cell comprises a T cell, a B cell, a regulatory T cell (Treg), a natural killer (NK) cell, a natural killer T (NKT) cell, a stem cell, or an induced pluripotent stem cell.

Provided herein is a pharmaceutical composition comprising the polynucleotide, vector, polypeptide, set of polypeptides, or a cell described herein, and a pharmaceutically acceptable carrier.

In some aspects, a cell or pharmaceutical composition described herein is for treating a subject in need of a therapy. In certain aspects, a polynucleotide, vector, composition, polypeptide, set of polypeptides, cell, or pharmaceutical composition described herein is for reducing or preventing exhaustion of a cell useful for a therapy.

Provided herein is a use of the cell or pharmaceutical composition described herein for the manufacture of a medicament in treating or preventing a disease or condition in a subject in need thereof. In some aspects, the disease or condition is a cancer.

Provided herein is a use of the polynucleotide, vector, composition, polypeptide, set of polypeptides, cell, or pharmaceutical composition described herein for preventing or reducing exhaustion of a cell useful for a therapy.

In some aspects, a method of treating or preventing a disease or condition in a subject in need thereof provided in the present disclosure, comprises administering any of the cell or pharmaceutical composition disclosed herein to the subject. In certain aspects, the disease or condition is a cancer.

Also provided herein is a method of increasing a c-Jun polypeptide in a cell comprising modifying a cell to comprise any of the polynucleotides, vectors, compositions, polypeptides or set of polypeptides provided herein, wherein after the modification the expression of the c-Jun polypeptide in the cell is increased compared to a corresponding cell that has been modified with a wild type c-Jun polynucleotide.

In some aspects, the expression of the c-Jun polypeptide is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 25-fold, at least about 30-fold, at least about 35-fold, at least about 40-fold, at least about 45-fold, at least about 50-fold, at least about 75-fold, at least about 100-fold, at least about 200-fold, at least about 300-fold, at least about 400-fold, at least about 500-fold, at least about 750-fold, or at least about 1,000-fold or more, compared to the corresponding cell. In some aspects, the expression of the c-Jun polypeptide is increased by about 1-fold, about 2-fold, about 3-fold, about 4-fold, about 5-fold, about 6-fold, about 7-fold, about 8-fold, about 9-fold- or about 10-fold compared to the corresponding cell.

BRIEF DESCRIPTION OF THE DRAWINGS

In FIG. 2A, the transduction efficiency is shown as percentage of cells that are EGFRt$^+$cJun$^+$. In FIG. 2B, the transduction efficiency is shown as percentage of cells that are EGFRt$^+$R12$^+$. In FIG. 2C, the gene expression level per cell is shown as the geometric mean (gMFI) of c-Jun expression among EGFRt$^+$ cells. In FIG. 2D, the gene expression level per cell is shown as the geometric mean (gMFI) of anti-ROR1 (R12) scFv expression among EGFRt$^+$ cells. As shown, each of the anti-ROR1 constructs were used to transduce the cells at the following multiplicity of infection (MOI): 20 (1$^{st}$ bar for each construct), 10 (2$^{nd}$ bar for each construct), 5 (3$^{rd}$ bar for each construct), and 2 (last bar for each construct). The anti-ROR1 CAR constructs tested are illustrated in FIG. 1 and included: (i) Construct #1 (i.e., lacking c-Jun); (ii) Construct #11 (i.e., comprising the codon-optimized c-Jun sequence set forth in SEQ ID NO: 9); (iii) Construct #2 (i.e., lacking c-Jun and comprising truncated CD19); (iv) Construct #3 (i.e., comprising the codon-optimized c-Jun sequence set forth in SEQ ID NO: 1); and (v) Construct #12 (i.e., comprising the codon-optimized c-Jun sequence set forth in SEQ ID NO: 10).

In FIG. 3A, results for the following anti-ROR1 CAR constructs are shown: (i) Construct #3 (i.e., comprising the codon-optimized c-Jun sequence set forth in SEQ ID NO: 1) (circle); (ii) Construct #5 (i.e., comprising the codon-optimized c-Jun sequence set forth in SEQ ID NO: 3) (square); (iii) Construct #4 (i.e., comprising the codon-optimized c-Jun sequence set forth in SEQ ID NO: 2) (triangle); and (iv) Construct #2 (i.e., lacking c-Jun and comprising truncated CD19) (diamond).

DETAILED DESCRIPTION OF THE DISCLOSURE

Overview

Figure 1:
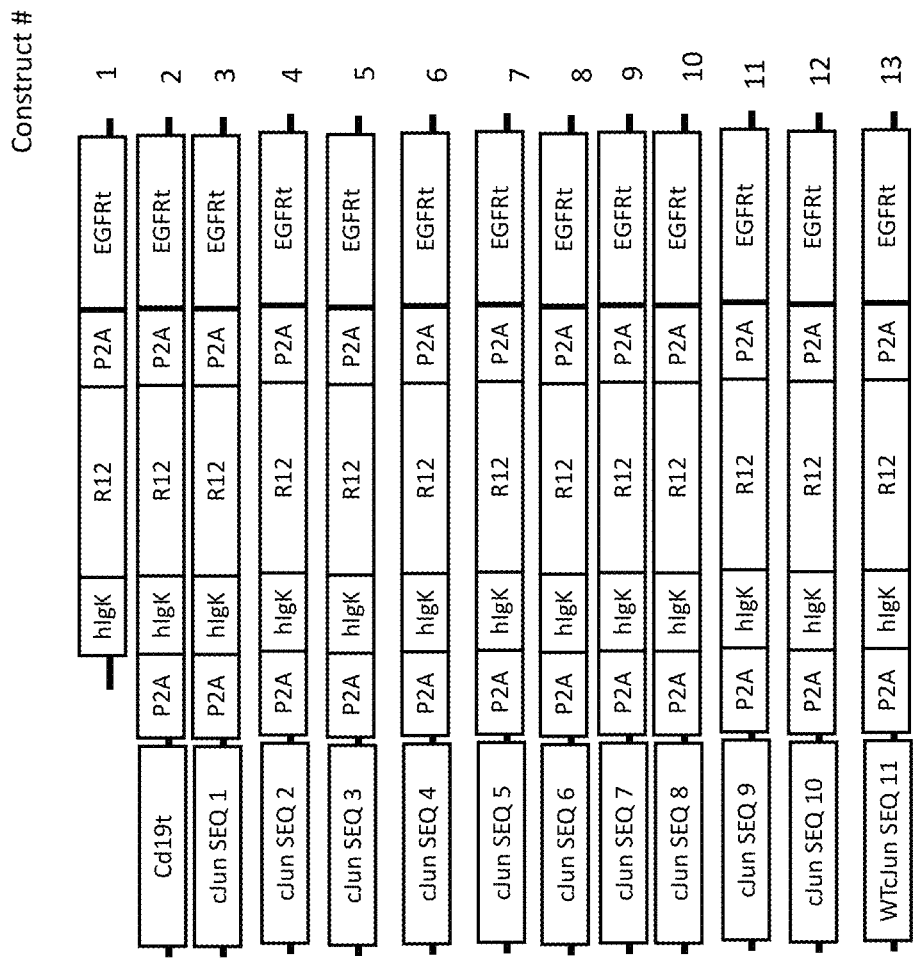
FIG. 1 shows a graphical representation of 13 different anti-ROR1 CAR constructs described herein. The constructs include nucleotide sequences encoding one or more of the following: (i) c-Jun protein ("cJun"); (ii) truncated CD19 ("CD19t"); (iii) P2A linker ("P2A"); (iv) human IgK signal peptide ("hIgK"); (v) anti-ROR1 scFv ("R12"); and (vi) truncated EGFR ("EGFRt"). Constructs #3-#12 include codon-optimized c-Jun sequences set forth in SEQ ID NOs: 1-10, respectively. Construct #13 include the wild-type (i.e., non-codon-optimized) c-Jun sequence (SEQ ID NO: 11).

The present disclosure is directed to a polynucleotide (e.g., isolated polynucleotide) comprising a nucleotide sequence encoding a Jun proto-oncogene, AP-1 transcription factor subunit ("c-Jun"; also referred to herein as "AP-1") protein. As described herein, the polynucleotides disclosed herein comprise one or more features, that render them distinct (e.g., structurally and/or functionally) from a reference polynucleotide that exists in nature. For instance, as further described elsewhere in the present disclosure, the nucleotide sequences have been codon-optimized (i.e., are synthetic). In some aspects, a polynucleotide of the present disclosure (e.g., comprising a codon-optimized AP-1 nucleotide sequence) further comprises one or more additional nucleotide sequences encoding one or more of the following: linker, signal peptide, antigen-binding domain, spacer, transmembrane domain, costimulatory domain, intracellular signaling domain, truncated EGFR, and combinations thereof.

Definitions

In order that the present disclosure can be more readily understood, certain terms are first defined. As used in this application, except as otherwise expressly provided herein, each of the following terms shall have the meaning set forth below. Additional definitions are set forth throughout the application.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein. It is further noted that the claims can be drafted to exclude any optional element. As such, this statement is intended to serve as antecedent basis for use of such exclusive terminology as "solely," "only" and the like in connection with the recitation of claim elements, or use of a negative limitation.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

As used herein, the term "approximately" or "about," as applied to one or more values of interest, refers to a value that is similar to a stated reference value and within a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). When the term "approximately" or "about" is applied herein to a particular value, the value without the term "approximately" or "about is also disclosed herein.

As described herein, any concentration range, percentage range, ratio range, or integer range is to be understood to include the value of any integer within the recited range and, when appropriate, fractions thereof (such as one tenth and one hundredth of an integer), unless otherwise indicated.

As used herein, the terms "ug" and "uM" are used interchangeably with "μg" and "μM," respectively.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

As used herein, the term "immune cell" refers to a cell of the immune system. In some aspects, the immune cell is selected from a T lymphocyte ("T cell"), B lymphocyte ("B cell"), natural killer (NK) cell, natural killer T (NKT) cell, macrophage, eosinophil, mast cell, dendritic cell or neutrophil. As used herein, the terms "T cell" and "T lymphocyte" are interchangeable and refer to any lymphocytes produced or processed by the thymus gland. Non-limiting classes of T cells include effector T cells and Th cells (such as $CD4^+$ or $CD8^+$ T cells). In some aspects, the immune cell is a Th1 cell. In some aspects, the immune cell is a Th2 cell. In some aspects, the immune cell is a Tc17 cell. In some aspects, the immune cell is a Th17 cell. In some aspects, the immune cell is a tumor-infiltrating cell (TIL). In some aspects, the immune cell is a $T_{reg}$ cell. As used herein, an "immune cell" also refers to a pluripotent cell, e.g., a stem cell (e.g., an embryonic stem cell or a hematopoietic stem cell) or an induced pluripotent stem cell, which is capable of differentiation into an immune cell.

In some aspects, the T cell is a memory T cell. As used herein, the term "memory" T cells refers to T cells that have previously encountered and responded to their cognate antigen (e.g., in vivo, in vitro, or ex vivo) or which have been stimulated with, e.g., an anti-CD3 antibody (e.g., in vitro or ex vivo). Immune cells having a "memory-like" phenotype upon secondary exposure, such memory T cells can reproduce to mount a faster and strong immune response than during the primary exposure. In some aspects, memory T cells comprise central memory T cells ($T_{CM}$ cells), effector memory T cells ($T_{EM}$ cells), tissue resident memory T cells ($T_{RM}$ cells), stem cell-like memory T cells ($T_{SCM}$ cells), or any combination thereof.

In some aspects, the T cell is a stem cell-like memory T cell. As used herein, the term "stem cell-like memory T cells," "T memory stem cells," or "$T_{SCM}$ cells" refer to memory T cells that express CD95, CD45RA, CCR7, and CD62L and are endowed with the stem cell-like ability to self-renew and the multipotent capacity to reconstitute the entire spectrum of memory and effector subsets.

In some aspects, the T cell is a central memory T cell. As used herein, the term "central memory T cells" or "$T_{CM}$ cells" refer to memory T cells that express CD45RO, CCR7, and CD62L. Central memory T cells are generally found within the lymph nodes and in peripheral circulation.

In some aspects, the T cell is an effector memory T cell. As used herein, the term "effector memory T cells" or "$T_{EM}$ cells" refer to memory T cells that express CD45RO but lack expression of CCR7 and CD62L. Because effector memory T cells lack lymph node-homing receptors (e.g., CCR7 and CD62L), these cells are typically found in peripheral circulation and in non-lymphoid tissues.

In some aspects, the T cell is a tissue resident memory T cell. As used herein, the term "tissue resident memory T cells" or "$T_{RM}$ cells" refer to memory T cells that do not circulate and remain resident in peripheral tissues, such as the skin, lung, and the gastrointestinal tract. In certain aspects, tissue resident memory T cells are also effector memory T cells.

In some aspects, the T cell is a naïve T cell. As used herein, the term "naïve T cells" or "$T_N$ cells" refers to T cells that express CD45RA, CCR7, and CD62L, but which do not express CD95. $T_N$ cells represent the most undifferentiated cell in the T cell lineage. The interaction between a $T_N$ cell and an antigen presenting cell (APC) induces differentiation of the $T_N$ cell towards an activated $T_{EFF}$ cell and an immune response. In some aspects, the T cell is an effector T ($T_{eff}$) cell.

As used herein, "cell engineering" refers to the targeted modification of a cell, e.g., an immune cell disclosed herein. In some aspects, the cell engineering comprises viral genetic engineering, non-viral genetic engineering, introduction of receptors to allow for tumor specific targeting (e.g., a chimeric binding protein) introduction of one or more endogenous genes that improve T cell function, introduction of one or more synthetic genes that improve immune cell, e.g., T cell, function (e.g., a codon-optimized AP-1 nucleotide sequence provided herein), or any combination thereof.

As used herein, the term "cytokine" refers to small, secreted proteins released by cells that have a specific effect on the interactions and communications between cells. Non-limiting examples of cytokines include interleukins (e.g., interleukin (IL)-1, IL-2, IL-4, IL-7, IL-9, IL-13, IL-15, IL-3, IL-5, IL-6, IL-11, IL-10, IL-20, IL-14, IL-16, IL-17, IL-21 and IL-23), interferons (IFN; e.g., IFNα, IFNβ, and IFNγ), tumor necrosis factor (TNF) family members, and transforming growth factor (TGF) family members. In certain aspects of the present disclosure, the interaction between TGFβ and a chimeric activation receptor disclosed herein in a host immune cell leads to increased expression of one or more cytokine. In some aspects, the cytokine is an interleukin. In some aspects, the cytokine is selected from IL-2, IL-7, IL-15, IL-21 and any combination thereof. In particular aspects, the cytokine is IL-2. IL-2 (UniProtKB-P60568) is produced by T cells in response to antigenic or mitogenic stimulation. IL-2 is known to stimulate T cell proliferation and other activities crucial to regulation of the immune response.

In some aspects, the cytokine is an interferon. In some aspects, the interferon is selected from IFNα, IFNβ, and IFNγ. In certain aspects, the interferon is IFNγ. IFNγ (UniProtKB-P01579) is produced by activated lymphocytes promoted immune cell function.

As used herein, the term "antigen" refers to any natural or synthetic immunogenic substance, such as a protein, peptide, or hapten. As used herein, the term "cognate antigen" refers to an antigen which an immune cell (e.g., T cell) recognizes and thereby, induces the activation of the immune cell (e.g., triggering intracellular signals that induce effector functions, such as cytokine production, and/or for proliferation of the cell). In certain aspects, the antigen comprises a tumor antigen. In some aspects, the antigen comprises a neoantigen.

A "cancer" refers to a broad group of various diseases characterized by the uncontrolled growth of abnormal cells in the body. Unregulated cell division and growth results in the formation of malignant tumors that invade neighboring tissues and can also metastasize to distant parts of the body through the lymphatic system or bloodstream. "Cancer" as used herein refers to primary, metastatic and recurrent cancers.

As used herein, the term "immune response" refers to a biological response within a vertebrate against foreign agents, which response protects the organism against these agents and diseases caused by them. An immune response is mediated by the action of a cell of the immune system (e.g., a T lymphocyte, B lymphocyte, natural killer (NK) cell, NKT cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell or a Th cell, such as a CD4$^+$ or CD8$^+$ T cell, or the inhibition of a Treg cell. As used herein, the terms "T cell" and "T lymphocytes" are interchangeable and refer to any lymphocytes produced or processed by the thymus gland. In some aspects, a T cell is a CD4+ T cell. In some aspects, a T cell is a CD8+ T cell. In some aspects, a T cell is a NKT cell.

As used herein, the term "anti-tumor immune response" refers to an immune response against a tumor antigen.

A "subject" includes any human or nonhuman animal. The term "nonhuman animal" includes, but is not limited to, vertebrates such as nonhuman primates, sheep, dogs, and rodents such as mice, rats and guinea pigs. In some aspects, the subject is a human. The terms "subject" and "patient" are used interchangeably herein. As used herein, the phrase "subject in need thereof" includes subjects, such as mammalian subjects, that would benefit, e.g., from administration of immune cells, e.g., T cells, as described herein to control tumor growth.

The term "effective amount" or "effective dosage" refers to an amount of an agent (e.g., an immune cell transduced with a polynucleotide comprising a nucleotide sequence encoding a chimeric binding protein and a codon-optimized c-Jun sequence) that provides the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. In reference to solid tumors, an effective amount comprises an amount sufficient to cause a tumor to shrink and/or to decrease the growth rate of the tumor (such as to suppress tumor growth) or to prevent or delay other unwanted cell proliferation. In some aspects, an effective amount is an amount sufficient to delay tumor development. In some aspects, an effective amount is an amount sufficient to prevent or delay tumor recurrence. An effective amount can be administered in one or more administrations. One of ordinary skill in the art will understand that a therapeutically effective amount etc. can be administered in a single dose, or can be achieved by administration of multiple doses (i.e., 1, 2, 3, 4, 5, 6, 7, 8, 9, 10 or more doses). The ability of a therapeutic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

The effective amount of the composition (e.g., immune cells as described herein) can, for example, (i) reduce the number of cancer cells; (ii) reduce tumor size; (iii) inhibit, delay, slow to some extent and can stop cancer cell infiltration into peripheral organs; (iv) inhibit (i.e., slow to some extent and can stop tumor metastasis); (v) inhibit tumor growth; (vi) prevent or delay occurrence and/or recurrence of tumor; and/or (vii) relieve to some extent one or more of the symptoms associated with the cancer.

The terms "effective" and "effectiveness" with regard to a treatment include both pharmacological effectiveness and physiological safety. Pharmacological effectiveness refers to the ability of a composition disclosed herein (e.g., immune cells described herein) to promote cancer regression in the patient. Physiological safety refers to the level of toxicity, or other adverse physiological effects at the cellular, organ, and/or organism level (adverse effects) resulting from administration of a composition disclosed herein (e.g., immune cells as described herein).

The terms "chimeric antigen receptor" and "CAR," as used herein, refer to a set of polypeptides, typically two in the simplest form, which when in an immune effector cell, provides the cell with specificity for a target cell, typically a cancer cell, and with intracellular signal generation. In some aspects, a CAR comprises at least an extracellular antigen-binding domain, a transmembrane domain and a cytoplasmic signaling domain (also referred to herein as "an intracellular signaling domain") comprising a functional signaling domain derived from a stimulatory molecule and/or costimulatory molecule as defined below. In some aspects, the set of polypeptides are in the same polypeptide chain, e.g., comprise a chimeric fusion protein. In some aspects, the set of polypeptides are not contiguous with each other, e.g., are in different polypeptide chains. In some aspects, the set of polypeptides include a dimerization switch that, upon the presence of a dimerization molecule, can couple the polypeptides to one another, e.g., can couple an antigen-binding domain to an intracellular signaling domain. In some aspects, the stimulatory molecule of the CAR is the zeta chain associated with the T cell receptor complex (e.g., CD3 zeta). In some aspects, the cytoplasmic signaling domain comprises a primary signaling domain (e.g., a primary signaling domain of CD3-zeta). In some aspects, the cytoplasmic signaling domain further comprises one or more functional signaling domains derived from at least one costimulatory molecule as defined below. In some aspects, the costimulatory molecule is chosen from the costimulatory molecules described herein, e.g., 4-1BB (i.e., CD137), CD27, and/or CD28.

In some aspects, the CAR comprises a chimeric fusion protein comprising an antigen-binding domain, a transmembrane domain, and an intracellular signaling domain comprising a functional signaling domain derived from a stimulatory molecule, wherein the antigen-binding domain and the transmembrane domain are linked by a CAR spacer. In some aspects, the CAR comprises a chimeric fusion protein comprising an antigen-binding domain linked to a transmembrane domain via a CAR spacer and an intracellular signaling domain comprising a functional signaling domain derived from a costimulatory molecule and a functional signaling domain derived from a stimulatory molecule. In some aspects, the CAR comprises a chimeric fusion protein comprising an antigen-binding domain linked to a transmembrane domain via a CAR spacer and an intracellular signaling domain comprising two functional signaling domains derived from one or more costimulatory molecule(s) and a functional signaling domain derived from a stimulatory molecule. In some aspects, the CAR comprises a chimeric fusion protein comprising an antigen-binding domain linked to a transmembrane domain via a CAR spacer and an intracellular signaling domain comprising at least two functional signaling domains derived from one or more costimulatory molecule(s) and a functional signaling domain derived from a stimulatory molecule. In some aspects, the CAR comprises an optional leader sequence at the amino-terminus (N-terminus) of the CAR. In some aspects, the CAR further comprises a leader sequence at the N-terminus of the antigen-binding domain, wherein the leader sequence is optionally cleaved from the antigen-binding domain (e.g., a scFv) during cellular processing and localization of the CAR to the cellular membrane.

Chimeric antigen receptors are distinguished from other antigen-binding agents by their ability to both bind MHC-independent antigen and transduce activation signals via their intracellular domain.

The antigen-specific extracellular domain of a chimeric antigen receptor recognizes and specifically binds an antigen, typically a surface-expressed antigen of a malignancy. An antigen-specific extracellular domain specifically binds an antigen when, for example, it binds the antigen with an affinity constant or affinity of interaction ($K_D$) between about 0.1 pM to about 10 for example, about 0.1 pM to about 1 µM or about 0.1 pM to about 100 nM. Methods for determining the affinity of interaction are known in the art. An antigen-specific extracellular domain suitable for use in a CAR of the present disclosure can be any antigen-binding polypeptide, a wide variety of which are known in the art. In some aspects, the antigen-binding domain is a single chain Fv (scFv). Other antibody-based recognition domains such as cAb VHH (camelid antibody variable domains) and humanized versions thereof, 1 gNAR VH (shark antibody variable domains) and humanized versions thereof, sdAb VH (single domain antibody variable domains), and "camelized" antibody variable domains are also suitable for use in a CAR of the present disclosure.

In some aspects, T cell receptor (TCR) based recognition domains, such as single chain TCR (scTv, i.e., single chain two-domain TCR containing Vα Vβ) are also suitable for use in the chimeric binding proteins of the present disclosure.

The terms "nucleic acids," "nucleic acid molecules, "nucleotides," "nucleotide(s) sequence," and "polynucleotide" can be used interchangeably and refer to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Single stranded nucleic acid sequences refer to single-stranded DNA (ssDNA) or single-stranded RNA (ssRNA). Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, supercoiled DNA and chromosomes. In discussing the structure of particular double-stranded DNA molecules, sequences can be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation. DNA includes, but is not limited to, cDNA, genomic DNA, plasmid DNA, synthetic DNA, and semi-synthetic DNA. A "nucleic acid composition" of the disclosure comprises one or more nucleic acids as described herein. As described herein, in some aspects, a polynucleotide of the present disclosure can comprise a single nucleotide sequence encoding a single protein (e.g., codon-optimized c-Jun nucleotide sequence) ("monocistronic"). In some aspects, a polynucleotide of the present disclosure is polycistronic (i.e., comprises two or more cistrons). In certain aspects, each of the cistrons of a polycistronic polynucleotide can encode for a protein disclosed herein (e.g., AP-1 transcription factor, chimeric binding protein, or EGFRt). In some aspects, each of the cistrons can be translated independently of one another.

As used herein, the term "polypeptide" encompasses both peptides and proteins, unless indicated otherwise.

As used herein, a "coding region," "coding sequence," or "translatable sequence" is a portion of polynucleotide which consists of codons translatable into amino acids. Although a "stop codon" (TAG, TGA, or TAA) is typically not translated into an amino acid, it can be considered to be part of a coding region, but any flanking sequences, for example promoters, ribosome binding sites, transcriptional terminators, introns, and the like, are not part of a coding region. The boundaries of a coding region are typically determined by a start codon at the 5' terminus, encoding the amino terminus of the resultant polypeptide, and a translation stop codon at the 3' terminus, encoding the carboxyl terminus of the resulting polypeptide.

The terms "complementary" and "complementarity" refer to two or more oligomers (i.e., each comprising a nucleobase sequence), or between an oligomer and a target gene, that are related with one another by Watson-Crick base-pairing rules. For example, the nucleobase sequence "T-G-A (5' to 3')," is complementary to the nucleobase sequence "A-C-T (3' to 5')." Complementarity can be "partial," in which less than all of the nucleobases of a given nucleobase sequence are matched to the other nucleobase sequence according to base pairing rules. For example, in some aspects, complementarity between a given nucleobase sequence and the other nucleobase sequence can be about 70%, about 75%, about 80%, about 85%, about 90%, or about 95%. Accordingly, in certain aspects, the term "complementary" refers to at least about 80%, at least about 85%, at least about 90%, at least about 91%, at least about 92%, at least about 93%, at least about 94%, at least about 95%, at least about 96%, at least about 97%, at least about 98%, or at least about 99% match or complementarity to a target nucleic acid sequence (e.g., c-Jun-encoding nucleic acid sequence). Or, there can be "complete" or "perfect" (100%) complementarity between a given nucleobase sequence and the other nucleobase sequence to continue the example. In some aspects, the degree of complementarity between nucleobase sequences has significant effects on the efficiency and strength of hybridization between the sequences.

The term "expression" as used herein refers to a process by which a polynucleotide produces a gene product, for example, an AP-1 transcription factor. It includes, without limitation, transcription of the polynucleotide into messenger RNA (mRNA) and the translation of an mRNA into a polypeptide. Expression produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation or splicing, or polypeptides with post translational modifications, e.g., methylation, glycosylation, the addition of lipids, association with other protein subunits, or proteolytic cleavage.

As used herein, the term "identity" refers to the overall monomer conservation between polymeric molecules, e.g., between polynucleotide molecules. The term "identical" without any additional qualifiers, e.g., polynucleotide A is identical to polynucleotide B, implies the polynucleotide sequences are 100% identical (100% sequence identity). Describing two sequences as, e.g., "70% identical," is equivalent to describing them as having, e.g., "70% sequence identity." A "reference nucleotide sequence," when used herein as a comparison to a nucleotide sequence of the disclosure, refers to a polynucleotide sequence essentially identical to the nucleotide sequence of the disclosure except that sequence is not optimized. For example, in some aspects, the reference nucleotide sequence comprises the wild-type JUN nucleic acid sequence set forth in SEQ ID NO: 11.

Calculation of the percent identity of two polypeptide or polynucleotide sequences, for example, can be performed by aligning the two sequences for optimal comparison purposes (e.g., gaps can be introduced in one or both of a first and a second polypeptide or polynucleotide sequences for optimal alignment and non-identical sequences can be disregarded for comparison purposes). In certain aspects, the length of a sequence aligned for comparison purposes is at least about 30%, at least about 40%, at least about 50%, at least about 60%, at least about 70%, at least about 80%, at least about 90%, at least about 95%, or about 100% of the length of the reference sequence. The amino acids at corresponding amino acid positions, or bases in the case of polynucleotides, are then compared.

When a position in the first sequence is occupied by the same amino acid or nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm.

Suitable software programs that can be used to align different sequences (e.g., polynucleotide sequences) are available from various sources. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at worldwideweb.ebi.ac.uk/Tools/psa.

Sequence alignments can be conducted using methods known in the art such as MAFFT, Clustal (ClustalW, Clustal X or Clustal Omega), MUSCLE, etc.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In certain aspects, the percentage identity (% ID) or of a first amino acid sequence (or nucleic acid sequence) to a second amino acid sequence (or nucleic acid sequence) is calculated as % ID=100×(Y/Z), where Y is the number of amino acid residues (or nucleobases) scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

One skilled in the art will appreciate that the generation of a sequence alignment for the calculation of a percent sequence identity is not limited to binary sequence-sequence comparisons exclusively driven by primary sequence data. It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at worldwidewebtcoffee.org, and alternatively available, e.g., from the EBI. It will also be appreciated that the final alignment used to calculate percent sequence identity can be curated either automatically or manually.

As used herein, the terms "isolated," "purified," "extracted," and grammatical variants thereof are used interchangeably and refer to the state of a preparation of desired composition of the present disclosure, e.g., codon optimized polynucleotides or engineered cells expressing proteins encoded by the codon optimized polynucleotides, that has undergone one or more processes of purification. In some aspects, isolating or purifying as used herein is the process of removing, partially removing (e.g., a fraction) of a composition of the present disclosure, e.g., a codon optimized polynucleotide of the present disclosure from a sample containing contaminants.

In some aspects, an isolated composition has no detectable undesired activity or, alternatively, the level or amount of the undesired activity is at or below an acceptable level or amount. In other aspects, an isolated composition has an amount and/or concentration of desired composition of the present disclosure, at or above an acceptable amount and/or concentration and/or activity. In other aspects, the isolated composition is enriched as compared to the starting material from which the composition is obtained. This enrichment can be by at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, at least about 99%, at least about 99.9%, at least about 99.99%, at least about 99.999%, at least about 99.9999%, or greater than 99.9999% as compared to the starting material.

In some aspects, isolated preparations are substantially free of residual biological products. In some aspects, the isolated preparations are 100% free, at least about 99% free, at least about 98% free, at least about 97% free, at least about 96% free, at least about 95% free, at least about 94% free, at least about 93% free, at least about 92% free, at least about 91% free, or at least about 90% free of any contaminating biological matter. Residual biological products can include abiotic materials (including chemicals) or unwanted nucleic acids, proteins, lipids, or metabolites.

The term "linked" as used herein refers to a first amino acid sequence or polynucleotide sequence covalently or non-covalently joined to a second amino acid sequence or polynucleotide sequence, respectively. The first amino acid or polynucleotide sequence can be directly joined or juxtaposed to the second amino acid or polynucleotide sequence or alternatively an intervening sequence can covalently join the first sequence to the second sequence. The term "linked" means not only a fusion of a first polynucleotide sequence to a second polynucleotide sequence at the 5'-end or the 3'-end, but also includes insertion of the whole first polynucleotide sequence (or the second polynucleotide sequence) into any two nucleotides in the second polynucleotide sequence (or the first polynucleotide sequence, respectively). The first polynucleotide sequence can be linked to a second polynucleotide sequence by a phosphodiester bond or a linker. The linker can be, e.g., a polynucleotide.

"Administering" refers to the physical introduction of a therapeutic agent (e.g., nucleic acid molecules described herein) to a subject, using any of the various methods and delivery systems known to those skilled in the art. Exemplary routes of administration include intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural, intrasterna, oral, rectal, topical, epidermal, mucosal, intranasal, vaginal, rectal, sublingual administration, and combinations thereof. Administering can also be performed, for example, once, a plurality of times, and/or over one or more extended periods.

"Treatment" or "therapy" of a subject refers to any type of intervention or process performed on, or the administration of an active agent to, a subject with the objective of reversing, alleviating, ameliorating, inhibiting, slowing down, or preventing the onset, progression, development, severity, or recurrence of a symptom, complication, condition, or biochemical indicia associated with a disease.

As used herein, the term "optimized," with regard to nucleotide sequences, refers to a polynucleotide sequence that encodes a polypeptide, wherein the polynucleotide sequence has been mutated to enhance a property of that polynucleotide sequence. In some aspects, the optimization is done to increase transcription levels, increase translation levels, increase steady-state mRNA levels, increase or decrease the binding of regulatory proteins such as general transcription factors, increase or decrease splicing, or increase the yield of the polypeptide produced by the polynucleotide sequence. Examples of changes that can be made to a polynucleotide sequence to optimize it include codon optimization, G/C content optimization, removal of repeat sequences, removal of AT rich elements, removal of cryptic splice sites, removal of cis-acting elements that repress transcription or translation, adding or removing poly-T or poly-A sequences, adding sequences around the transcription start site that enhance transcription, such as Kozak consensus sequences, removal of sequences that could form stem loop structures, removal of destabilizing sequences, and two or more combinations thereof. Additional disclosure relating to such optimizations are provided throughout the present disclosure.

As used herein, the term "promoter" refers to DNA sequence capable of controlling the expression of a coding sequence or functional RNA. In general, a coding sequence is located 3' to a promoter sequence. Promoters can be derived in their entirety from a native gene, or be composed of different elements derived from different promoters found in nature, or even comprise synthetic DNA segments. It is understood by those skilled in the art that different promoters can direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." It is further recognized that since in most cases the exact boundaries of regulatory sequences have not been completely defined, DNA fragments of different lengths can have identical promoter activity.

Various aspects of the disclosure are described in further detail in the following subsections.

c-Jun Expressing Nucleotide Sequences c-Jun (also referred to herein as "AP-1 transcription factor" or "AP-1") is an oncogenic transcription factor belonging to the activator protein-1 (AP-1) family. It interacts with various proteins (e.g., c-Fos) to form dimeric complexes that modulate a diverse range of cellular signaling pathways, including cell proliferation and tumor progression. Accordingly, increased c-Jun expression has been observed in certain cancers, and there has been much interest in developing c-Jun antagonists to treat such cancer. See, e.g., Brennan, A., et al., *J Exp Clin Cancer Res* 39(1): 184 (September 2020).

In humans, the c-Jun protein is encoded by the JUN gene, which is located on chromosome 1 (nucleotides 58,780,791 to 58,784,047 of GenBank Accession No. NC_000001.11, minus strand orientation). Synonyms of the JUN gene, and the encoded protein thereof, are known and include "Jun proto-oncogene, AP-1 transcription factor subunit," "v-Jun avian sarcoma virus 17 oncogene homolog," "transcription factor AP-1," "Jun oncogene," "AP-1," "Jun activation domain binding protein," "p39", and "enhancer-binding protein AP1." The wild-type human c-Jun protein sequence is 331 amino acids in length. The amino acid and nucleic acid sequences of the wild-type human c-Jun are provided in Tables 1 and 2, respectively.

TABLE 1

| c-Jun Protein Sequence | |
|---|---|
| Wild-type human c-Jun (UniProt: P05412-1) (SEQ ID NO: 13) | MTAKMETTFYDDALNASFLPSESGPYGYSNP KILKQSMTLNLADPVGSLKPHLRAKNSDLLT SPDVGLLKLASPELERLIIQSSNGHITTTPT PTQFLCPKNVTDEQEGFAEGFVRALAELHSQ NTLPSVTSAAQPVNGAGMVAPAVASVAGGSG SGGFSASLHSEPPVYANLSNFNPGALSSGGG APSYGAAGLAFPAQPQQQQQPPHHLPQQMPV QHPRLQALKEEPQTVPEMPGETPPLSPIDME SQERIKAERKRMRNRIAASKCRKRKLERIAR LEEKVKTLKAQNSELASTANMLREQVAQLKQ KVMNHVNSGCQLMLTQQLQTF |

TABLE 2

| c-Jun Nucleic Acid Sequence | |
|---|---|
| Wild-type JUN (GenBank Accession No. NM_002228.4) (SEQ ID NO: 12) *coding region is bolded and capitalized (SEQ ID NO: 11) | gctcagagttgcactgagtgtggctgaagcagcgaggcgggagtggaggtgcgcggagt caggcagacagacagacacagccagccagccaggtcggcagtatagtccgaactgcaaa tcttattttcttttcaccttctctctaactgcccagagctagcgcctgtggctcccggg ctggtgtttcgggagtgtccagagagcctggtctccagccgccccgggaggagagccc tgctgcccaggcgctgttgacagcggcggaaagcagcggtacccacgcgcccgccgggg gaagtcggcgagcggctgcagcagcaaagaacttccccggctgggaggaccggagacaa gtggcagagtcccggagccaacttttgcaagcctttcctgcgtcttaggcttctccacg gcggtaaagaccagaaggcggccggagagccacgcaagagaagaaggacgtgcgctcagc ttcgctcgcaccggttgttgaacttgggcgagcgcgagccgcggctgccgggcgccccc tccccctagcagcggaggaggggacaagtcgtcggagtccgggcggccaagacccgccg ccggccggccactgcagggtccgcactgatccgctccgcggggagagccgctgctctgg gaagtgagttcgcctgcggactccgaggaaccgctgcgcacgaagagcgctcagtgagt gaccgcgacttttcaaagccgggtagcgcgcgcgagtcgacaagtaagagtgcgggagg catcttaattaaccctgcgctccctggagcgagctggtgaggagggcgcagcggggacg acagccagcgggtgcgtgcgctcttagagaaactttccctgtcaaaggctccgggggc gcgggtgtccccgcttgccacagccctgttgcggccccgaaacttgtgcgcgcagccc aaactaacctcacgtgaagtgacggactgttctATGACTGCAAAGATGGAAACGACCTT CTATGACGATGCCCTCAACGCCTCGTTCCTCCCGTCCGAGAGCGGACCTTATGGCTACA GTAACCCCAAGATCCTGAAACAGAGCATGACCCTGAACCTGGCCGACCCAGTGGGGAGC CTGAAGCCGCACCTCCGCGCCAAGAACTCGGACCTCCTCACCTCGCCCGACGTGGGGCT GCTCAAGCTGGCGTCGCCCGAGCTGGAGCGCCTGATAATCCAGTCCAGCAACGGGCACA TCACCACCACGCCGACCCCCACCCAGTTCCTGTGCCCCAAGAACGTGACAGATGAGCAG GAGGGCTTCGCCGAGGGCTTCGTGCGCGCCCTGGCCGAACTGCACAGCCAGAACACGCT GCCCAGCGTCACGTCGGCGGCGCAGCCGGTCAACGGGGCAGGCATGGTGGCTCCCGCGG TAGCCTCGGTGGCAGGGGGCAGCGGCAGCGGCGGCTTCAGCGCCAGCCTGCACAGCGAG CCGCCGGTCTACGCAAACCTCAGCAACTTCAACCCAGGCGCGCTGAGCAGCGGCGGCGG GGCGCCCTCCTACGGCGCGGCCGGCCTGGCCTTTCCCGCGCAACCCCAGCAGCAGCAGC AGCCGCCGCACCACCTGCCCCAGCAGATGCCCGTGCAGCACCCGCGGCTGCAGGCCCTG AAGGAGGAGCCTCAGACAGTGCCCGAGATGCCCGGCGAGACACCGCCCCTGTCCCCCAT CGACATGGAGTCCCAGGAGCGGATCAAGGCGGAGAGGAAGCGCATGAGGAACCGCATCG CTGCCTCCAAGTGCCGAAAAAGGAAGCTGGAGAGAATCGCCCGGCTGGAGGAAAAAGTG AAAACCTTGAAAGCTCAGAACTCGGAGCTGGCGTCCACGGCCAACATGCTCAGGGAACA GGTGGCACAGCTTAAACAGAAAGTCATGAACCACGTTAACAGTGGGTGCCAACTCATGC TAACGCAGCAGTTGCAAACATTTtgaagagagaccgtcgggggctgaggggcaacgaag aaaaaaataacacagagagacagacttgagaacttgacaagttgcgacggagagaaaa aagaagtgtccgagaactaaagccaagggtatccaagttggactgggttgcgtcctgac ggcgcccccagtgtgcacgagtgggaaggacttggcgcgccctcccttggcgtggagcc agggagcggccgcctgcgggctgccccgctttgcggacgggctgtccccgcgcgaacgg aacgttggacttttcgttaacattgaccaagaactgcatggacctaacattcgatctca |

TABLE 2-continued c-Jun Nucleic Acid Sequence

```
ttcagtattaaagggggggaggggggagggggttacaaactgcaatagagactgtagattg
cttctgtagtactccttaagaacacaaagcggggggagggttggggagggggcggcagga
gggaggtttgtgagagcgaggctgagcctacagatgaactctttctggcctgccttcgt
taactgtgtatgtacatatatatattttttaatttgatgaaagctgattactgtcaata
aacagcttcatgcctttgtaagttatttcttgtttgtttgtttgggtatcctgcccagt
gttgtttgtaaataagagatttggagcactctgagtttaccatttgtaataaagtatat
aatttttttatgttttgtttctgaaaattccagaaaggatatttaagaaaatacaataa
actattggaaagtactcccctaacctcttttctgcatcatctgtagatactagctatct
aggtggagttgaaagagttaagaatgtcgattaaaatcactctcagtgcttcttactat
taagcagtaaaaactgttctctattagactttagaaataaatgtacctgatgtacctga
tgctatggtcaggttatactcctcctcccccagctatctatatggaattgcttaccaaa
ggatagtgcgatgtttcaggaggctggaggaagggggggttgcagtggagagggacagcc
cactgagaagtcaaacatttcaaagtttggattgtatcaagtggcatgtgctgtgacca
tttataatgttagtagaaattttacaataggtgcttattctcaaagcaggaattggtgg
cagattttacaaaagatgtatccttccaatttggaatcttctctttgacaattcctaga
taaaaagatggcctttgcttatgaatatttataacagcattcttgtcacaataaatgta
ttcaaataccaa
```

Codon Optimization

As described herein, a polynucleotide of the present disclosure comprises a nucleotide sequence encoding an AP-1 transcription factor, wherein the nucleotide sequence has been codon-optimized. Accordingly, in some aspects, the nucleotide sequence encoding a c-Jun protein described herein differs from that of the wild-type c-Jun nucleotide sequence (e.g., SEQ ID NO: 11).

In some aspects, a nucleotide sequence encoding an AP-1 transcription factor has at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to any one of the nucleic acid sequences set forth in SEQ ID NOs: 1 to 10. In certain aspects, a nucleotide sequence encoding an AP-1 transcription factor comprises the nucleic acid sequence set forth in any one of SEQ ID NOs: 1 to 10.

In some aspects, a nucleotide sequence encoding an AP-1 transcription factor has at least about 80%, at least about 85%, at least about 90%, at least about 95%, at least about 96%, at least about 97%, at least about 98%, or at least about 99% sequence identity to the nucleic acid sequence set forth in SEQ ID NO: 1. In certain aspects, a nucleotide sequence encoding an AP-1 transcription factor has at least 89%, at least 90%, at least 91%, at least 92%, at least 93%, at least 94%, at least 95%, at least 96%, at least 97%, at least 98%, or at least 99% sequence identity to the nucleic acid sequence set forth in SEQ ID NO: 1. In some aspects, the nucleotide sequence comprises the nucleic acid sequence set forth in SEQ ID NO: 1.

In some aspects, a nucleotide sequence encoding an AP-1 transcription factor has at least about 80%, at least about 85%, at least about 90%, at least about 95%, at least about 96%, at least about 97%, at least about 98%, or at least about 99% sequence identity to the nucleic acid sequence set forth in SEQ ID NO: 2. In certain aspects, a nucleotide sequence encoding an AP-1 transcription factor has at least 90%, at least 91%, at least 92%, at least 93%, at least 94%, at least 95%, at least 96%, at least 97%, at least 98%, or at least 99% sequence identity to the nucleic acid sequence set forth in SEQ ID NO: 2. In some aspects, the nucleotide sequence comprises the nucleic acid sequence set forth in SEQ ID NO: 2.

In some aspects, a nucleotide sequence encoding an AP-1 transcription factor has at least about 80%, at least about 85%, at least about 90%, at least about 95%, at least about 96%, at least about 97%, at least about 98%, or at least about 99% sequence identity to the nucleic acid sequence set forth in SEQ ID NO: 3. In certain aspects, a nucleotide sequence encoding an AP-1 transcription factor described herein has at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence set forth in SEQ ID NO: 3. In some aspects, the nucleotide sequence comprises the nucleic acid sequence set forth in SEQ ID NO: 3.

In some aspects, a nucleotide sequence encoding an AP-1 transcription factor has at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the nucleic acid sequence set forth in SEQ ID NO: 4. In certain aspects, a nucleotide sequence has at least 96%, at least 97%, at least 98%, or at least 99% to the nucleic acid sequence set forth in SEQ ID NO: 4. In some aspects, the nucleotide sequence comprises the nucleic acid sequence set forth in SEQ ID NO: 4.

In some aspects, a nucleotide sequence encoding an AP-1 transcription factor has at least about 70%, at least about 75%, at least about 80%, at least about 85%, at least about 90%, at least about 95%, at least about 96%, at least about 97%, at least about 98%, or at least about 99% sequence identity to the nucleic acid sequence set forth in SEQ ID NO: 5. In certain aspects, a nucleotide sequence encoding an AP-1 transcription factor has at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence set forth in SEQ ID NO: 5. In some aspects, the nucleotide sequence comprises the nucleic acid sequence set forth in SEQ ID NO: 5.

In some aspects, a nucleotide sequence encoding an AP-1 transcription factor has at least about 80%, at least 85%, at least about 90%, at least about 95%, at least about 96%, at least about 97%, at least about 98%, or at least about 99% sequence identity to the nucleic acid sequence set forth in SEQ ID NO: 6. In certain aspects, a nucleotide sequence encoding an AP-1 transcription factor has at least 88%, at least 89%, at least 90%, at least 91%, at least 92%, at least 93%, at least 94%, at least 95%, at least 96%, at least 97%, at least 98%, or at least 99% sequence identity to the nucleic acid sequence set forth in SEQ ID NO: 6. In some aspects, the nucleotide sequence comprises the nucleic acid sequence set forth in SEQ ID NO: 6.

In some aspects, a nucleotide sequence encoding an AP-1 transcription factor has at least about 80%, at least about 85%, at least about 90%, at least about 95%, at least about 96%, at least about 97%, at least about 98%, or at least about 99% sequence identity to the nucleic acid sequence set forth in SEQ ID NO: 7. In certain aspects, a nucleotide sequence encoding an AP-1 transcription factor has at least 88%, at least 89%, at least 90%, at least 91%, at least 92%, at least 93%, at least 94%, at least 95%, at least 96%, at least 97%, at least 98%, or at least 99% sequence identity to the nucleic acid sequence set forth in SEQ ID NO: 7. In some aspects, the nucleotide sequence comprises the nucleotide sequence set forth in SEQ ID NO: 7.

In some aspects, a nucleotide sequence encoding an AP-1 transcription factor has at least about 80%, at least about 85%, at least about 90%, at least about 95%, at least about 96%, at least about 97%, at least about 98%, or at least about 99% sequence identity to the nucleic acid sequence set forth in SEQ ID NO: 8. In certain aspects, a nucleotide sequence encoding an AP-1 transcription factor has at least 90%, at least 91%, at least 92%, at least 93%, at least 94%, at least 95%, at least 96%, at least 97%, at least 98%, or at least 99% sequence identity to the nucleic acid sequence set forth in SEQ ID NO: 8. In some aspects, the nucleotide sequence comprises the nucleotide sequence set forth in SEQ ID NO: 8.

In some aspects, a nucleotide sequence encoding an AP-1 transcription factor has at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the nucleic acid sequence set forth in SEQ ID NO: 9. In certain aspects, a nucleotide sequence encoding an AP-1 transcription factor has at least 88%, at least 89%, at least 90%, at least 91%, at least 92%, at least 93%, at least 94%, at least 95%, at least 96%, at least 97%, at least 98%, or at least 99% sequence identity to the nucleic acid sequence set forth in SEQ ID NO: 9. In some aspects, the nucleotide sequence comprises the nucleotide sequence set forth in SEQ ID NO: 9.

In some aspects, a nucleotide sequence encoding an AP-1 transcription factor has at least about 85%, at least about 90%, at least about 95%, at least about 96%, at least about 97%, at least about 98%, or at least about 99% sequence identity to the nucleic acid sequence set forth in SEQ ID NO: 10. In certain aspects, a nucleotide sequence encoding an AP-1 transcription factor has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence set forth in SEQ ID NO: 10. In some aspects, the nucleotide sequence comprises the nucleotide sequence set forth in SEQ ID NO: 10.

Exemplary codon-optimized AP-1 nucleotide sequences are provided in Table 3 (below).

TABLE 3

Codon-Optimized c-Jun Nucleotide Sequences

| | |
|---|---|
| Codon-optimized c-Jun nucleotide sequence #1 (SEQ ID NO: 1) | atgacagccaagatggaaaccacattctacgacgacgccctgaacgcctcattcctgc cttctgagagcggaccttacggctacagcaatcctaagatcctgaaacagagcatgac ccttaacctggctgatcctgttggaagcctgaaacctcacctgagagccaaaacagc gacctgctcaccagccctgatgtgggcctgctgaagctggcctctccagagctggaac ggctgatcatccagagcagcaacggccacatcacaaccacccctacccctacacaatt cctgtgccctaagaacgtgaccgacgagcaggagggcttcgccgaaggctttgtgcgg gccctggcagaactgcactctcagaacaccctgcctagcgtgacctccgccgcccagc ctgtcaacggcgccggaatggtggccctgccgtggcttctgtggccggcggcagcgg cagcggcggattcagcgcctctctgcactctgagcctcctgtctacgccaatctgtct aatttcaaccccggagccctgtccagcggcggcggagctcctagctacgcgctgctg gactggccttccccgcccagcccagcaacagcagcagcctccacaccacctgcccca gcagatgcccgtgcagcaccctagactgcaggcctgaaggaagaacccaaacagtg cctgagatgcctggcgagacacctccactgagcccatcgacatggaaagccaggagc ggatcaaggccgagagaaagagaatgcggaacagaatcgccgctagcaagtgcagaaa gcggaagctggaaagaatcgccagactggaagagaaggtgaagaccctgaaagccaa aatagcgagctggccagcaccgccaacatgctgcgggaacaggtggcccagctgaagc agaaggtgatgaaccacgtgaactctggttgtcagctgatgctgacccagcagctcca gaccttc |
| Codon-optimized c-Jun nucleotide sequence #2 (SEQ ID NO: 2) | atgacagccaagatggaaaccaccttctacgacgacgccctcaacgcctccttcctgc cttctgagagcggtccttacggctacagcaaccccaagatcctgaagcaaagcatgac cctgaacctggccgaccccgttggctccctgaaacctcacctgagagccaaaacagc gacctgctgaccagccctgatgtgggcctgctgaagctggcctctccagagctggaaa gactgattatccagagcagcaacggccacatcaccacaacacctaccctacacagtt cctgtgccctaagaacgtgactgatgagcaggagggctttgccgagggcttcgtgaga gccctggctgagctgcattctcagaacaccctgcctagcgtgacctctgccgcccagc ctgttaatggcgccggcatggtggccctgccgtggcctctgtggccggaggcagcgg cagcggcggattcagcgcctctctgcacagcgagcccccgtctacgccaacctgagc aatttcaaccctggcgccctgtccagcggcggcggcgcccttcatatggcgctgccg gcctggccttcccgctcagcccagcagcagcaacagcctccacaccacctgcccca gcagatgcccgtgcagcacccagactgcaggcctgaaggaagaacctcagaccgtg cccgagatgcctggcgagaccctcctctgagccctatcgacatggaaagccaggaga gaatcaaggccgagaggaagcggatgcggaacagaatcgccgccagcaagtgcagaaa aagaaagctgaacggatcgccagactggaggagaaggtgaagacactgaaagccaa aattctgaactggcctctaccgccaatatgctgcgcgagcaggtggctcaactgaagc agaaggtgatgaaccacgtgaacagcggatgtcagctgatgctgacacagcagctgca gactttt |

TABLE 3-continued

Codon-Optimized c-Jun Nucleotide Sequences

| | |
|---|---|
| Codon-optimized c-Jun nucleotide sequence #3 (SEQ ID NO: 3) | atgaccgccaagatggaaaccaccttctacgacgacgccctgaacgccagctttctgc cttctgagtctggccctacggctacagcaaccccaagatcctgaagcagagcatgac cctgaacctggccgatcctgtgggcagcctgaaacctcacctgagagccaagaacagc gacctgctgacaagccctgatgtgggcctgctgaaactggcctctcctgagctggaac ggctgatcatccagagcagcaacgccacataccaccacacctacaccaacacagtt tctgtgccccaagaacgtgaccgacgagcaagagggattgccgagggctttgttaga gccctggccgaactgcacagccagaataccctgcctagcgtgacatctgccgctcagc ctgttaatggcgccggaatggttgctcctgccgtggcttctgttgctggcggatctgg atctggcggtttagcgcctctctgcactctgagcctccagtgtacgccaacctgagc aacttcaaccctggcgctcttagctctggtggcggagcaccttcttatggcgctgccg gattggcctttcctgctcagcctcagcagcagcaacagcctcctcatcatctgcccca gcagatgcctgtgcagcacccagactgcaggccctgaaagaggaacccagacagtc cctgagatgcccggcgaaacacctcctctgagccccatcgacatggaaagccaagagc ggatcaaggccgagcggaagcggatgagaaatagaatcgccgcctccaagtgccggaa gaggaagctggaaagaatcgcccggctggaagagaaagtgaaaaccctgaaggcccag aactccgagctggcctctaccgccaacatgctgagagaacaggtggcccagctgaaac agaaagtcatgaaccacgtgaacagcggctgccagctgatgctgacacagcagctgca gaccttc |
| Codon-optimized c-Jun nucleotide sequence #4 (SEQ ID NO: 4) | atgactgccaaaatggagactacattctatgacgacgccctcaatgccagttttttgc cgagtgaatccggccctacggctattcaaacccaagatcctcaagcaatcaatgac cctcaatcttgctgacccagttggctccctgaaacccatctcagagctaaaaatagt gacctccttacttcccctgatgttggactcctcaaacttgcttctcccgaactcgaac gcttgatcattcaatcttccaacggccacatcacaacaacacccacacccacccagtt tctttgcccaaaaaatgtcaccgatgaacaggaaggtttcgcggaaggattcgtccgc gcgctggccgaactgcactcccagaatacacttccttcagttacgtcagccgcccagc cagtgaatggtgcgggaatggttgctcctgcggtcgcttctgtcgcaggggggctccgg ttctggcggatttagcgcctctctgcattccgagccacctgtatatgctaatctttct aattttaaccccggagccttgtctagcggcggtggtgcccccagctacggtgctgcag gactcgcttcccagctcaacctcagcagcagcaacaaccccccatcaccttcccca acagatgccagtacaacatccaaggctccaggccctcaaagaggaaccacagacggtg cccgaaatgcctggcgaaactccaccactttcccctattgatatggaatcccaagagc gcatcaaggccgaaagaaagcgaatgcggaatagaatagcagcttcaaaatgtagaaa acggaaattggaacgaatcgcacggttggaagaaaaagtgaagaccttgaaagcccag aacagtgagctcgcctctaccgctaacatgctgcgcgagcaagtcgcacaacttaagc agaaggtgatgaaccatgtgaatagcggatgtcaacttatgctgactcaacagttgca aacctttt |
| Codon-optimized c-Jun nucleotide sequence #5 (SEQ ID NO: 5) | atgaccgcgaaaatggagacaacattttacgatgatgcactgaacgcctcttttctgc caagtgaatccggcccctacggatactcaaacccaagattctgaaacagtctatgac tctcaacctggccgacccagttggcagtctgaagcctcatttgcgagccaagaatagt gatctgctgacctcccagacgtgggactgctgaaactcgcctcacctgaacttgagc gcttgattatacagtcatccaatgggcacatcacaacaacacctactcctacccagtt tctgtgccccaaaaacgtcaccgatgagcaggagggattcgcggaaggctttgtgcgc gcctggctgaattgcatagtcagaacactcttcccagcgtaaccagcgccgcccaac cagtgaatggagccggtatggtggctcccgcggttgctagtgttgcggggggtcagg ctctggtgggttcagtgcttctcttcactctgaacccctgtgtatgccaatctgtct aactttaaccctggggccctctcctctggtgggggtgccccagctacggagcggccg gcctggccttttcctgcccagcctcagcagcagcagcaaccccctcatcatcttccgca gcagatgccagtacagcatccacgcctgcaggctcttaaggaggagcccagacggtg cccgaaatgcccggggaaactccacccttgtccccattgacatggagtcccaggagc ggatcaaggctgaaagaaagaggatgcggaatcgcatcgcagcctctaaatgccgcaa gcggaaacttgagaggatcgcgcggttggaggaaaaagtaaaaaccttgaaggcacag aactctgagctggcgagtactgccaacatgctcagagaacaagtcgcacagctgaagc agaaagtgatgaaccatgtgaacagcggttgtcagctgatgctgactcagcagctgca gaccttc |
| Codon-optimized c-Jun nucleotide sequence #6 (SEQ ID NO: 6) | atgaccgccaagatggagaccacattctacgatgacgctctgaacgcttcctttctgc cttccgagtccggccctacggctactccaatcccaagattctgaagcagagcatgac actgaatctggctgatcccgtgggatctctgaagcctcatctgagagccaagaattcc gatctgctgacaagccccgacgtgggactgctcaaactggccagccccgaactggaga ggctcattatccagagctccaacggccacatcaccacaacacctaccctacccagtt tctctgtcccaagaacgtgacagacgagcaagagggatttgccgaaggcttcgtgaga gccctcgccgaactgcatagccagaataccctgccttccgtgaccagcgctgctcaac ccgtgaacggcgctggcatggtcgctcccgccgtcgccagcgtggctggaggaagcgg atccggaggcttcagcgcttccctccacagcgaacctccgtgtacgctaatctgagc aacttcaaccccggcgctctgagcagcggaggaggagctcctagctatggagctgccg gactggcttttcctgcccagcccagcagcagcagcagcccccatcatctgcctca gcagatgcccgtgcagcatcccagactccaagctctgaaggaggagcctcagaccgtc cccgagatgcccggcgaaacccctcctgtccccatcgacatggaaagccaagagaga ggatcaaggccgagaggaagaggatgaggaataaatcgccgccagcaagtgtagaaa gaggaagctggagaggatcgccagactggaggagaaagtgaagaccctcaaggctcag aattccgagctggccagcacagccaacatgctgagagagcaagtggcccagctcaagc agaaggtgatgaaccacgtcaacagcggatgccagctgatgctcacccagcagctgca gaccttc |

TABLE 3-continued

Codon-Optimized c-Jun Nucleotide Sequences

| | |
|---|---|
| Codon-optimized c-Jun nucleotide sequence #7 (SEQ ID NO: 7) | atgaccgctaaaatggaaaccactttctatgacgatgccctgaacgcctccttcctc cgtccgagtccggaccctacggatactcaaatcctaagatcctcaaacagtcgatgac cctcaacctggccgaccccgtgggatccctgaagccgcacttgcgcgccaagaactcc gacctcctgacgagcccagacgtgggcctgctgaagctcgcatcacccgaacttgagc ggttgatcattcagtcctccaacggacatataccaccactcccaccccaactcagtt tctgtgtccgaagaacgtgaccgatgagcaagagggattcgccgagggattcgtgcgg gccctggccgagctgcatagccagaacacccttccatccgtgacctcggcggctcagc ctgtgaacggcgcgggaatggtcgcgcccgccgtggcctcggtggccggggcagcgg cagcgggggattttccgcgtcgctgcactccgagccgccggtgtacgccaacctgtca aacttcaaccctggggccctgagctccggcggtggagcaccttcgtacggcgccgctg gcctggccgttccccgcgcaaccacagcagcaacagcagcccctcaccacctccccca acaaatgcctgtgcagcacccgaggctgcaggccctcaaggaagaacccagactgtg ccggaaatgccggggagactccgccgctgtcccctatcgacatggaatcacaggaac gcattaaggcagagcggaagcgcatgcggaaccggattgccgcctccaagtgccgcaa gagaaagctcgaaagaatcgccagattggaagaaaaggtcaagactctgaaggcccag aactctgagctggcatccaccgctaatatgctgagggaacaagtggcccagctgaaac agaaggtcatgaaccacgtcaacagcggttgccagctgatgctgacccagcaactcca gacattc |
| Codon-optimized c-Jun nucleotide sequence #8 (SEQ ID NO: 8) | atgaccgccaagatggagaccaccttctacgacgacgccctgaacgccagcttcctgc ccagcgagagcggaccctacggctactctaaccccaagatcctgaaacagagcatgac actgaatctggccgaccccgtgggcagcctgaagcctccacctctagagccaagaacagc gacctgctgaccagccccgacgtgggcctgctgaagctcgcctcgccagagttagaga gactgatcatccagtccagcaacggccacatcacaaccacccccaaccctacccagtt cctgtgccccaagaacgtgaccgacgagcaggagggcttcgccgagggctttgtgaga gccctggccgagttgcactctcagaacaccctgccctccgtgaccagcgccgctcaac ctgtgaacggcgcaggaatggttgctcctgccgtggccagcgttgcaggcggatctgg aagtggaggcttctccgcctcccttcacagcgagcctcccgtgtacgccaacctgagc aacttcaaccccggcgccctgagcagtggaggaggcgctcccagctatggagcagctg gattagccttccccgcccagccacagcagcagcaacagcctcccaccacctgcctca gcaaatgcctgtgcagcacctcggctgcaggcccttaaggaggagcccagaccgtt cctgagatgcctggcgagaccctccctgagccctatcgacatggagtcccaggagc ggatcaaggccgagcggaagcggatgcggaaccggatcgctgcttccaagtgccggaa gagaaagctggagagaatcgcccggctggaggagaaggtgaagaccctgaaggcccag aactccgagctggcctccaccgccaacatgctgcgggagcaggttgcacagctgaagc agaaggtcatgaaccacgtgaacagcggctgccagctgatgctgacccagcagctgca gaccttc |
| Codon-optimized c-Jun nucleotide sequence #9 (SEQ ID NO: 9) | atgacagcgaagatggagacaaccttctatgacgatgctcttaacgcctccttcctgc cttccgaaagcgggccctacgggtactctaatcctaagatacttaagcaatcgatgac tctcaacctcgctgaccccggttggctcactgaaaccacacctgagagctaagaatagt gacctgctcactagtcccgatgtcgggcttctgaagctggcctctcccgagctggaga ggcttatcatccaatcatcaaatggccacatcaccactacccaacaccaactcaatt cctttgccctaaaaacgtgaccgacgaacaggaaggcttcgccgagggttttgtccgg gccttggccgagctgcattctcaaaatacactgccaagcgtcacttctgcggcgcagc cggttaacggagcagggatggtggctcccgccgttgctagcgtggccggcggttccgg ctccggcggtttctctgcctccttgcattctgagccaccagtctacgcgaacctgtcc aactttaatccgggggcgctgagtagcggaggcggcgcccctagctatggggcagctg gactggccttccccggcacaaccccaacaacaacagcaaccgccacaccatcttcctca acaaatgccagtgcaacatccacgcttacaagccctcaaggaggaacccagaccgtg cctgagatgcccggcgaaacccccgccattgagccctattgacatggaaagtcaagaga gaattaaggcagagcgcaagagaatgaggaaccggatcgcagcatctaagtgccgcaa acggaaattggagcggatcgctcgcttggaggagaaggtcaagactctcaaggcccag aactccgagcttgcgagcacagctaatatgctgcgcgagcaggtggcccagttaaaac aaaaggtcatgaaccatgtgaacagcggctgtcagctgatgcttacgcaacagctgca aacctttggctccggtgcaacgaacttcagcctgctgaagcaggccggagatgttgag gaaaatccaggtccc |
| Codon-optimized c-Jun nucleotide sequence #10 (SEQ ID NO: 10) | atgacggccaaaatggagactacgttctacgatgacgcactcaacgcgtccttcctgc cctctgagagtggacctatggctactccaatccaaagatcctgaagcagtctatgac cctcaacctggcgaccccgtgggctcccttaagccgcacttgcgcgccaagaactcc gacctgctgacctcccctgatgtgggcctcctcaagctcgctagccctgaattggaga ggctgatcatccagagctcaaatggccacatcaccaccacacctaccccaacccagtt cctgtgcccaaaaacgtgaccgacgagcaggagggcttcgcggagggctttcgtcaga gctctggccgagctgcactcacagaacacgctcccttccgtgacctccgctgcccagc cggtcaatggcgctggaatggtggctccggctgtggcctctgttgccggcggctccgg ctccggaggcttttcagcttctctgcattctgagccccagtgtacgctaacctgagc aacttcaaccccggggcgctcagctccggtggcggtgccccgagctacggcgcggctg ggctggcgttccccgctcagcctcagcagcaacagcaacctcccaccacctgccaca gcagatgcctgtgcagcacccacgcctgcaggcttgaaggaggaacctcagactgtg ccagagatgcccggcgagaccccacccctgtcccgattgacatggagagccaggagc gcatcaaggcagagcgcaagcgtatgcgcaaccgcatcgcggcctccaagtgccgaaa gcgcaagctggagcggattgctcgcctggaggagaaggtgaagaccctgaaggcccag aattccgagctggcctcgaccgccaacatgctacgagaacaggtcgcgcagctgaaac agaaggtcatgaaccatgtcaacagcgggtgccagctgatgttgacccagcagcttca gaccttc |

The AP-1 nucleotide sequence disclosed herein can be codon-optimized using any methods known in the art. For instance, in certain aspects, the codons of an AP-1 nucleotide sequence disclosed herein has been optimized to modify (e.g., increase or decrease) one or more of the following parameters compared to the wild-type nucleotide sequence (e.g., SEQ ID NO: 11): (i) codon adaptation index (i.e., codon usage bias); (ii) guanine-cytosine (GC) nucleotide content; (iii) mRNA secondary structure and unstable motifs; (iv) repeat sequences (e.g., direct repeats, inverted repeats, dyad repeats); (v) restriction enzyme recognition sites; or (vi) combinations thereof.

Not to be bound by any one theory, in some aspects, such codon optimization can increase the expression of the protein encoded by the nucleotide sequence (e.g., c-Jun). Accordingly, in some aspects, a codon-optimized AP-1 nucleotide sequence of the present disclosure is capable of increasing the expression of the encoded AP-1 transcription factor when transfected, transduced or otherwise introduced into a human cell, e.g., a human T cell, compared to a corresponding expression in a cell transfected with the wild-type nucleotide sequence (e.g., SEQ ID NO: 11). In some aspects, the expression of the AP-1 transcription factor is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 25-fold, at least about 30-fold, at least about 35-fold, at least about 40-fold, at least about 45-fold, at least about 50-fold, at least about 75-fold, at least about 100-fold, at least about 200-fold, at least about 300-fold, at least about 400-fold, at least about 500-fold, at least about 750-fold, or at least about 1,000-fold or more, compared to the corresponding expression in the cell transfected, transduced, or otherwise genetically modified to express with the wild-type nucleotide sequence (e.g., SEQ ID NO: 11) (i.e., "reference cell"). In some aspects, the expression of the c-Jun polypeptide is increased by about 1-fold, about 2-fold, about 3-fold, about 4-fold, about 5-fold, about 6-fold, about 7-fold, about 8-fold, about 9-fold- or about 10-fold compared to the reference cell.

In some aspects, the increased expression of the AP-1 transcription factor can improve and/or enhance one or more properties of the transfected cells (e.g., immune cells, e.g., T cells, such as CD4+ and/or CD8+ T cells). Non-limiting examples of such properties include: resistance to exhaustion (e.g., as indicated by reduced expression of exhaustion markers, such as PD-1, CD39, TIM-3, and/or LAG-3; increased survival; and/or increased cytokine production), increased persistence/survival, increased expansion/proliferation, improved effector function (e.g., cytokine production upon antigen stimulation, lysis of cells expressing the target antigen, or both), or combinations thereof.

Assays useful for measuring exhaustion, cell phenotype, persistence, cytotoxicity and/or killing, proliferation, cytokine production/release, and gene expression profiles are known in the art and include, for example flow cytometry, intracellular cytokine staining (ICS), INCUCYTE® immune cell killing analysis, Meso Scale Discovery (MSD) or similar assay, persistent antigen stimulation assays, bulk and single cell RNAseq (see e.g., *Fron Genet.* 2020; 11:220; 2019 Bioinformatics 35:i436-445; 2019 *Annual Review of Biomed. Data Sci.* 2:139-173), cytotoxicity/killing assays, ELISA, western blot and other standard molecular and cell biology methods such as described herein or as described, for example, in Current Protocols in Molecular Biology or Current Protocols in Immunology (John Wiley & Sons, Inc., 1999-2021) or elsewhere.

In some aspects, the increased expression of the AP-1 transcription factor increases the resistance of the cell to exhaustion. In some aspects, the resistance to exhaustion is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 25-fold, at least about 30-fold, at least about 35-fold, at least about 40-fold, at least about 45-fold, at least about 50-fold, at least about 75-fold, at least about 100-fold, at least about 200-fold, at least about 300-fold, at least about 400-fold, at least about 500-fold, at least about 750-fold, or at least about 1,000-fold or more, compared to a reference cell (e.g., corresponding cell that was not modified to have increased AP-1 expression).

In some aspects, the over-expression of the AP-1 transcription factor can decrease exhaustion in an exhausted cell. In certain aspects, the increased expression of the AP-1 transcription factor can decrease exhaustion by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%, compared to a reference cell (e.g., corresponding exhausted cell that was not modified to have increased AP-1 expression).

In some aspects, the increased expression of the AP-1 transcription factor can increase the persistence/survival of the cell, e.g., when administered to a subject in vivo. In certain aspects, the persistence/survival of the cell is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 25-fold, at least about 30-fold, at least about 35-fold, at least about 40-fold, at least about 45-fold, at least about 50-fold, at least about 75-fold, at least about 100-fold, at least about 200-fold, at least about 300-fold, at least about 400-fold, at least about 500-fold, at least about 750-fold, or at least about 1,000-fold or more, compared to a reference cell (e.g., corresponding cell that was not modified to have increased AP-1 expression).

In some aspects, the increased expression of the AP-1 transcription factor can increase the expansion/proliferation of the cell, e.g., upon antigen stimulation. In certain aspects, the expansion/proliferation of the cell is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 25-fold, at least about 30-fold, at least about 35-fold, at least about 40-fold, at least about 45-fold, at least about 50-fold, at least about 75-fold, at least about 100-fold, at least about 200-fold, at least about 300-fold, at least about 400-fold, at least about 500-fold, at least about 750-fold, or at least about 1,000-fold or more, compared to a reference cell (e.g., corresponding cell that was not modified to have increased AP-1 expression).

In some aspects, the increased expression of the AP-1 transcription factor can increase the effector function of the cell, e.g., increased cytokine production, granzyme release, and/or cytotoxicity. In certain aspects, the effector function of the cell is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 25-fold, at least about 30-fold, at least about 35-fold, at least about 40-fold, at least about 45-fold, at least about 50-fold, at least about 75-fold, at least about 100-fold, at least about 200-fold, at least about 300-fold, at least about 400-fold, at least about 500-fold, at least about 750-fold, or at least about 1,000-fold or more, compared to a reference cell (e.g., corresponding cell that was not modified to have increased AP-1 expression).

Overexpression of c-Jun in T cells helps sustain the active state of the cells by, e.g., alleviating or preventing T cell dysfunction (e.g., T cell exhaustion). The codon optimized c-Jun described herein can be used to engineer immune cells, such as T cells, which then exhibit sustained, potent cytotoxicity against desired target cells (e.g., the target of the endogenous TCR or the target of a chimeric binding protein as described herein). As compared to T cells that do not overexpress c-Jun, engineered T cells overexpressing the codon optimized c-Jun disclosed herein display fewer signs of T cell exhaustion.

Codon Usage Bias

Despite the ever-increasing knowledge of expression systems and recombinant DNA technology, significant obstacles exist in expressing certain genes (e.g., foreign or synthetic) in a selected cell. For example, expression of a synthetic gene, even when coupled with a strong promoter, often occurs with much lower efficiency or kinetics than would be expected. The same is frequently true of exogenous genes that are foreign to the cell. In some aspects, this lower than expected expression efficiency is due to the protein coding regions of the gene having a codon usage pattern that does not resemble codon usage patterns in the cell that the protein is being expressed.

Accordingly, in some aspects, a codon-optimized AP-1 nucleotide sequence disclosed herein has a human codon adaptation index that is increased relative to the wild-type nucleotide sequence (e.g., SEQ ID NO: 11). As used herein, the term "codon adaptation index" refers to a measure of codon usage bias. A codon adaptation index (CAI) measures the deviation of a given protein coding gene sequence with respect to a reference set of genes (Sharp PM and Li WH, *Nucleic Acids Res.* 15(3):1281-95 (1987)). CAI is calculated by determining the geometric mean of the weight associated to each codon over the length of the gene sequence (measured in codons):

$$CAI = \exp(1/L \Sigma_{i=1}^{L} \ln(w_i(l))), \quad (I)$$

For each amino acid, the weight of each of its codons, in CAI, is computed as the ratio between the observed frequency of the codon (fi) and the frequency of the synonymous codon (fj) for that amino acid:

$$w_i = f_i / \max(f_i) ij \in [\text{synonymous condons for amino acid}] \quad (II)$$

In some aspects, a codon-optimized AP-1 nucleotide sequence disclosed herein has a CAI of at least about 0.75 (75%), at least about 0.76 (76%), at least about 0.77 (77%), at least about 0.78 (78%), at least about 0.79 (79%), at least about 0.80 (80%), at least about 0.81 (81%), at least about 0.82 (82%), at least about 0.83 (83%), at least about 0.84 (84%), at least about 0.85 (85%), at least about 0.86 (86%), at least about 0.87 (87%), at least about 0.88 (88%), at least about 0.89 (89%), at least about 0.90 (90%), at least about 0.91 (91%), at least about 0.92 (92%), at least about 0.93 (93%), at least about 0.94 (94%), at least about 0.95 (95%), at least about 0.96 (96%), at least about 0.97 (97%), at least about 0.98 (98%), or at least about 0.99 (99%).

G/C Content Optimization

Human genes are highly heterogeneous in their G/C content, with some genes having a G/C content as low as 20%, and other genes having a G/C content as high as 95%. In general, G/C rich genes are more highly expressed. In fact, it has been demonstrated that increasing the G/C content of a gene can lead to increased expression of the gene, due mostly to an increase in transcription and higher steady state mRNA levels. See Kudla et al., *PLoS Biol* 4(6): e180 (2006). As used herein, the terms "G/C content" (or guanine-cytosine content) or "percentage of G/C nucleotides" refers to the percentage of nitrogenous bases in a DNA molecule that are either guanine or cytosine. G/C content can be calculated using the following formula:

$$G+C/A+T+G+C \times 100 \quad (III)$$

In some aspects, a codon-optimized AP-1 nucleotide sequence disclosed herein contains a higher percentage of G/C nucleotides compared to the percentage of G/C nucleotides in the wild-type nucleotide sequence (e.g., SEQ ID NO: 11). In some aspects, the codon-optimized AP-1 nucleotide sequence described herein has a G/C content that is at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, or at least about 65%. In certain aspects, a codon-optimized AP-1 nucleotide sequence disclosed herein has a G/C content that is at least about 0.60 (60%) (e.g., SEQ ID NO: 1). In some aspects, a codon-optimized AP-1 nucleotide sequence disclosed herein has a G/C content that is at least about 0.61 (61%) (e.g., SEQ ID NO: 2). In some aspects, a codon-optimized AP-1 nucleotide sequence has a G/C content that is at least about 0.59 (59%) (e.g., SEQ ID NO: 3). In some aspects, a codon-optimized AP-1 nucleotide sequence has a G/C content that is at least about 0.52 (52%) (e.g., SEQ ID NO: 4). In some aspects, a codon-optimized AP-1 nucleotide sequence of the present disclosure has a G/C content that is at least about 0.56 (56%) (e.g., SEQ ID NO: 5). In some aspects, a codon-optimized AP-1 nucleotide sequence described herein has a G/C content that is at least about 0.59 (59%) (e.g., SEQ ID NO: 6). In some aspects, a codon-optimized AP-1 nucleotide sequence has a G/C content that is at least about 0.61 (61%) (e.g., SEQ ID NO: 7). In some aspects, a codon-optimized AP-1 nucleotide sequence has a G/C content that is at least about 0.63 (63%)

(e.g., SEQ ID NO: 8). In some aspects, a codon-optimized AP-1 nucleotide sequence has a G/C content that is at least about 0.56 (56%) (e.g., SEQ ID NO: 9). In some aspects, a codon-optimized AP-1 nucleotide sequence has a G/C content that is at least about 0.62 (62%) (e.g., SEQ ID NO: 10).

Additional Translatable Sequences

In some aspects, a polynucleotide described herein (e.g., an expression construct comprising a nucleotide sequence encoding an AP-1 transcription factor) can further comprise one or more nucleotide sequences encoding additional proteins of interest. Accordingly, in some aspects, polynucleotides of the present disclosure can be used to express an AP-1 transcription factor in combination with any suitable proteins of interest. Non-limiting examples of such additional translatable sequences are described below.

Ligand Binding Proteins

In some aspects, a polynucleotide provided herein (e.g., an expression construct comprising a codon-optimized AP-1 nucleotide sequence) further comprises a nucleotide sequence encoding a ligand binding protein. As used herein, the term "ligand binding protein" refers to any protein that is able to bind a molecule of interest (i.e., ligand) (e.g., an antigen expressed on a tumor cell or a peptide/WIC complex). In certain aspects, a ligand binding protein is a chimeric binding protein. As used herein, the term "chimeric binding protein" refers to proteins that are capable of binding to one or more ligands (e.g., antigens (e.g., comprising an antigen-binding moiety)) and are created through the joining of two or more polynucleotide sequences which originally code for separate proteins. Unless indicated otherwise, the terms can be used interchangeably in the present disclosure.

Non-limiting examples of ligand binding proteins (e.g., chimeric binding proteins) include a chimeric antigen receptor (CAR), T cell receptor (TCR), chimeric antibody-T cell receptor (caTCR), chimeric signaling receptor (CSR), T cell receptor mimic (TCR mimic), and combinations thereof.

In some aspects, the chimeric binding protein comprises a CAR.

In some aspects, the CAR (e.g., which can be expressed in combination with an AP-1 transcription factor) is designed as a standard CAR. In a "standard CAR", the different components (e.g., the extracellular targeting domain, transmembrane domain, and intracellular signaling/activation domain) are linearly constructed as a single fusion protein. In some aspects, the CAR is designed as a first generation CAR. "First generation" CARs are composed of an extracellular binding domain, a hinge region, a transmembrane domain, and one or more intracellular signaling domains. All first generation CARs contain the CD3 chain domain as the intracellular signaling domain. In some aspects, the CAR is designed as a second generation CAR. "Second generation" CARs additionally contain a costimulatory domain (e.g., CD28 or 4-1BB). In some aspects, the CAR is designed as a third generation CAR. "Third generation" CARs are similar to the second generation CARs except that they contain multiple costimulatory domains (e.g., CD28-4-1BB or CD28-OX40). In some aspects, the CAR is designed as a fourth generation CAR. "Fourth generation" CARs (also known as TRUCKs or armored CARs) additionally contain additional factors that can further improve function. For example, in some aspects, the fourth generation CARs additionally contain cytokines which can be released upon CAR signaling in the targeted tumor tissue. In certain aspects, the fourth generation CARs comprise one or more additional elements such as homing and suicide genes, which can help further regulate the activity of the CAR. In some aspects, the CAR is designed as a split CAR. In a "split CAR" system, one or more components of the CAR (e.g., extracellular targeting domain, transmembrane domain, and intracellular signaling/activation domain) are split into two or more parts such that it is dependent on multiple inputs that promote assembly of the intact functional receptor. In some aspects, the CAR is designed as a switchable CAR. With a "switchable CAR," the CAR can be switched (e.g., transiently) on (on-switch CAR) or off (off-switch CAR) in the presence of a stimulus. Additional examples of CARs that can be used with the present disclosure are described, e.g., in US 2020/0172879 A1 and US 2019/0183932 A1, each of which is incorporated herein by reference in its entirety.

In some aspects, the constructs herein encode an engineered T cell receptor (TCR) (also referred to in the art as "transgenic" TCRs). TCR is a molecule found on the surface of T cells which is responsible for recognizing fragments of antigen as peptides bound to major histocompatibility complex (MHC) molecules. The TCR is a heterodimer composed of two different protein chains. In some aspects, the TCR consists of an alpha (α) chain and a beta (β) chain (encoded by TRA and TRB, respectively). In some aspects, the TCR consists of gamma and delta (γ/δ) chains (encoded by TRG and TRD, respectively). When the TCR engages with an antigenic peptide presented by an MHC molecule (peptide/MHC), the T lymphocyte is activated through signal transduction. In some aspects, the TCR is an engineered (transgenic) TCR. As used herein, the term "engineered TCR" or "engineered T cell receptor" refers to a T cell receptor (TCR) that is isolated or engineered to specifically bind with a desired affinity to a major histocompatibility complex (MHC)/peptide target antigen and that is introduced into a population of immune cells, e.g., T cells, NK cells, and/or TILs.

In some aspects, the chimeric binding protein comprises a chimeric antibody-T cell receptor (caTCR). As used herein, a "chimeric antibody-T cell receptor" or "caTCR" comprises (i) an antibody moiety that specifically binds to an antigen of interest and (ii) a T cell receptor module capable of recruiting at least one TCR-associated signaling molecule. In some aspects, the antibody moiety and the T cell receptor module are fused together. In some aspects, the chimeric binding protein comprises a chimeric signaling receptor (CSR). "Chimeric signaling receptor" or "CSR" comprises a ligand-binding domain that specifically binds to a target ligand and a co-stimulatory signaling domain capable of providing a stimulatory signal to an immune cell that expresses the CSR. Non-limiting examples of caTCR and CSR are further described in U.S. Pat. No. 10,822,413 B2, which is incorporated herein by reference in its entirety.

In some aspects, the chimeric binding protein comprises a T cell receptor mimic (TCR mimic). As used herein, the term "T cell receptor mimic" or "TCR mimic" refers to an antibody (or a fragment thereof) that has been engineered to recognize tumor antigens, where the tumor antigens are displayed in the context of HLA molecules. As will be apparent to those skilled in the art, these antibodies can mimic the specificity of TCR. Non-limiting examples of TCR mimics are provided, e.g., in US 2009/0226474 A1 and US 2019/0092876 A1, each of which is incorporated herein by reference in its entirety.

In some aspects, the chimeric binding protein can be associated with a gene editing tool (e.g., CRISPR-Cas system), where the activation of the chimeric binding protein can induce the activation of the gene-editing tool, such that the expression and/or activity of one or more genes are modulated in the cell. For example, in some aspects, a cell described herein (e.g., T cells) is modified to comprise a chimeric binding protein (e.g., CAR) which is linked to a protease and a single guide RNA targeting a regulatory region (e.g., promoter) of a gene of interest. In some aspects, the cell is modified to further comprise a linker for activation of T cells (LAT), complexed to a gene-editing tool, e.g., via a linker. Activation of the chimeric binding protein (e.g., via antigen stimulation) allows the release of the gene editing tool for nuclear localization and modulation of gene expression. Additional aspects of such chimeric binding proteins are provided elsewhere in the present disclosure. See also Pietrobon et al., *Int J Mol Sci* 22(19): 10828 (October 2021), which is incorporated herein by reference in its entirety.

As described herein, a chimeric binding protein useful for the present disclosure comprises an antigen-binding domain, a transmembrane domain, a costimulatory domain, an intracellular signaling domain, or combinations thereof. In certain aspects, the antigen-binding domain recognizes and specifically binds an antigen. Non-limiting examples of antigens include: AFP (alpha-fetoprotein), αvβ6 or another integrin, BCMA, Braf, B7-H3, B7-H6, CA9 (carbonic anhydrase 9), CCL-1 (C—C motif chemokine ligand 1), CD5, CD19, CD20, CD21, CD22, CD23, CD24, CD30, CD33, CD38, CD40, CD44, CD44v6, CD44v7/8, CD45, CD47, CD56, CD66e, CD70, CD74, CD79a, CD79b, CD98, CD123, CD138, CD171, CD352, CEA (carcinoembryonic antigen), Claudin 18.2, Claudin 6, c-MET, DLL3 (delta-like protein 3), DLL4, ENPP3 (ectonucleotide pyrophosphatase/phosphodiesterase family member 3), EpCAM, EPG-2 (epithelial glycoprotein 2), EPG-40, ephrinB2, EPHa2 (ephrine receptor A2), ERBB dimers, estrogen receptor, ETBR (endothelin B receptor), FAP-α (fibroblast activation protein α), fetal AchR (fetal acetylcholine receptor), FBP (a folate binding protein), FCRL5, FR-α (folate receptor alpha), GCC (guanyl cyclase C), GD2, GD3, GPC2 (glypican-2), GPC3, gp100 (glycoprotein 100), GPNMB (glycoprotein NMB), GPRC5D (G Protein Coupled Receptor 5D), HER2, HER3, HER4, hepatitis B surface antigen, HLA-A1 (human leukocyte antigen A1), HLA-A2 (human leukocyte antigen A2), HMW-MAA (human high molecular weight-melanoma-associated antigen), IGF1R (insulin-like growth factor 1 receptor), Ig kappa, Ig lambda, IL-22Ra (IL-22 receptor alpha), IL-13Ra2 (IL-13 receptor alpha 2), KDR (kinase insert domain receptor), LI cell adhesion molecule (LI-CAM), Liv-1, LRRC8A (leucine rich repeat containing 8 Family member A), Lewis Y, melanoma-associated antigen (MAGE)-A1, MAGE-A3, MAGE-A6, MART-1 (melan A), murine cytomegalovirus (MCMV), MCSP (melanoma-associated chondroitin sulfate proteoglycan), mesothelin, mucin 1 (MUC1), MUC16, MHC/peptide complexes (e.g., HLA-A complexed with peptides derived from AFP, KRAS, HPV (e.g., HPV E6 or E7), NY-ESO, MAGE-A, and WT1), NCAM (neural cell adhesion molecule), Nectin-4, NKG2D (natural killer group 2 member D) ligands, NY-ESO, oncofetal antigen, PD-1, PD-L1, PRAME (preferentially expressed antigen of melanoma), progesterone receptor, PSA (prostate specific antigen), PSCA (prostate stem cell antigen), PSMA (prostate specific membrane antigen), ROR1, ROR2, SIRPα (signal-regulatory protein alpha), SLIT, SLITRK6 (NTRK-like protein 6), STEAP1 (six transmembrane epithelial antigen of the prostate 1), survivin, TAG72 (tumor-associated glycoprotein 72), TPBG (trophoblast glycoprotein), Trop-2, VEGFR1 (vascular endothelial growth factor receptor 1), VEGFR2, and antigens from HIV, HBV, HCV, HPV, and other pathogens, or combinations thereof. In some aspects, the antigen-binding domain of a chimeric binding protein described herein specifically binds to ROR1. In some aspects, the antigen-binding domain of a chimeric binding protein specifically binds to GPC2. In some aspects, the antigen-binding domain of a chimeric binding protein specifically binds to a tumor antigen, wherein the tumor antigen is derived from alpha fetoprotein (AFP), CD19, BCMA, CLL-1, CS1, CD38, CD19, TSHR, CD123, CD22, CD30, CD171, CD33, EGFRvIII, GD2, GD3, Tn Ag, PSMA, ROR1, ROR2, GPC1, GPC2, FLT3, FAP, TAG72, CD44v6, CEA, EPCAM, B7H3, KIT, IL-13Ra2, mesothelin, IL-11Ra, PSCA, PRSS21, VEGFR2, LewisY, CD24, PDGFR-beta, SSEA-4, CD20, folate receptor alpha, ERBB2 (Her2/neu), MUC1, MUC16, EGFR, NCAM, prostase, PAP, ELF2M, Ephrin B2, IGF-I receptor, CAIX, LMP2, gp100, bcr-abl, tyrosinase, EphA2, fucosyl GM1, sLe, GM3, TGS5, HMW-MAA, o-acetyl-GD2, folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6,E7, MAGE A1, ETV6-AML, sperm protein 17, XAGE1, Tie 2, MAD-CT-1, MAD-CT-2, Fos-related antigen 1, p53, p53 mutant, prostein, surviving, telomerase, PCTA-1/Galectin 8, MelanA/MART1, Ras mutant (e.g., HRAS, KRAS, NRAS), hTERT, sarcoma translocation breakpoints, ML-IAP, ERG (TMPRSS2 ETS fusion gene), NA17, PAX3, androgen receptor, cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, IGLL1, CD2, CD3c, CD4, CD5, CD7, the extracellular portion of the APRIL protein, neoantigen, or any combinations thereof.

As further described elsewhere in the present disclosure, the antigen-binding domain of a chimeric binding protein can be any polypeptide capable of binding one or more antigens. In some aspects, the antigen-binding domain comprises, or is derived from, an Ig NAR, a Fab fragment, a Fab' fragment, a F(ab)'2 fragment, a F(ab)'3 fragment, an Fv, a single chain variable fragment (scFv), a bis-scFv, a (scFv)2, a minibody, a diabody, a triabody, a tetrabody, an intrabody, a disulfide stabilized Fv protein (dsFv), a unibody, a nanobody, and an antigen binding region derived from an antibody that may specifically bind to any of a protein of interest, a ligand, a receptor, a receptor fragment, a peptide aptamer, or combinations thereof. In some aspects, the antigen-binding domain is a single chain Fv (scFv).

In some aspects, a chimeric binding protein described herein comprises an intracellular signaling domain that transduces the effector function signal upon binding of an antigen to the extracellular domain and directs the cell expressing the chimeric binding protein (e.g., T cell) to perform a specialized function. Non-limiting examples of intracellular signaling domain include an intracellular signaling domain region derived from CD3 zeta, FcR gamma, common FcR gamma (FCER1G), Fc gamma RIIa, FcR beta (Fc Epsilon Rib), CD3 gamma, CD3 delta, CD3 epsilon, CD22, CD79a, CD79b, CD278 ("ICOS"), FcεRI, CD66d, CD32, DAP10, DAP12, or any combination thereof. In certain aspects, the intracellular signaling domain comprises a CD3 zeta intracellular signaling domain. In some aspects, the chimeric binding protein comprises the entire intracellular domain of a protein disclosed herein. In some aspects, the intracellular domain is truncated. Truncated portion of an intracellular domain can be used in place of the intact chain as long as it still transduces the effector function signal. The term intracellular domain is thus meant to include any truncated portion of the intracellular domain sufficient to transduce the effector function signal.

In some aspects, a chimeric binding protein that can be encoded in a polynucleotide described herein (e.g., comprising a codon-optimized AP-1 nucleotide sequence) further comprises a transmembrane domain. In certain aspects, the antigen-binding domain is linked to the intracellular domain of a chimeric binding protein by a transmembrane domain. In some aspects, the antigen-binding domain is connected to the transmembrane domain of a chimeric binding protein (e.g., CAR) by a linker. In certain aspects, inclusion of a linker between the antigen-binding domain and the transmembrane domain can affect flexibility of the antigen-binding domain and thereby, improve chimeric binding protein function.

Any transmembrane domain known in the art can be used in the chimeric binding proteins described herein (e.g., CARs). In some aspects, the transmembrane domain is artificial (e.g., an engineered transmembrane domain). In some aspects, the transmembrane domain is derived from a naturally occurring polypeptide. In some aspects, the transmembrane domain comprises a transmembrane domain from a naturally occurring polypeptide. Non-limiting examples of transmembrane domain include a transmembrane domain region of KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKG2D, NKG2C, CD19, or any combination thereof. In certain aspects, the transmembrane domain comprises a CD28 transmembrane domain.

As described herein, in some aspects, a chimeric binding protein (e.g., CAR) comprises one or more costimulatory domains (e.g., second and third generation CARs). Not to be bound by any one theory, these costimulatory domains can further improve the expansion, activation, memory, persistence, and/or effector function of a cell engineered to express the chimeric binding protein (e.g., in combination with the AP-1 transcription factor). In some aspects, the transmembrane domain is fused to the costimulatory domain, optionally a costimulatory domain is fused to a second costimulatory domain, and the costimulatory domain is fused to a signaling domain, not limited to CD3. Non-limiting examples of costimulatory domain include interleukin-2 receptor (IL-2R), interleukin-12 receptor (IL-12R), IL-7, IL-21, IL-23, IL-15, CD2, CD3, CD4, CD7, CD8, CD27, CD28, CD30, CD40, 4-1BB/CD137, ICOS, lymphocyte function-associated antigen-1 (LFA-1), LIGHT, NKG2C, OX40, DAP10, or any combination thereof. In certain aspects, the costimulatory domain comprises a 4-1BB/CD137 costimulatory domain.

Linkers

In some aspects, a polynucleotide described herein (e.g., comprising a codon-optimized AP-1 nucleotide sequence) further comprises a nucleotide sequence encoding a linker. The linker can be between any of the different components of a polynucleotide provided herein. For instance, in certain aspects, a polynucleotide comprises a first nucleotide sequence encoding an AP-1 transcription factor, a second nucleotide sequence encoding a linker, and a third nucleotide sequence encoding a chimeric binding protein (e.g., CAR), wherein the second nucleotide sequence is between the first and third nucleotide sequences, such that the AP-1 transcription factor is linked to the chimeric binding protein by the linker. In some aspects, a polynucleotide of the present disclosure can comprise multiple nucleotide sequences encoding a linker (e.g., at least two separate nucleotide sequences). In certain aspects, the multiple linkers are the same. In some aspects, the multiple linkers are different.

In certain aspects, the linker is a peptide linker. In some aspect, the linker comprises at least about 1 amino acid, at least about 2 amino acids, at least about 3 amino acids, at least about 4 amino acids, at least about 5 amino acids, at least about 6 amino acids, at least about 7 amino acids, at least about 8 amino acids, at least about 9 amino acids, at least about 10 amino acids, at least about 11 amino acids, at least about 12 amino acids, at least about 13 amino acids, at least about 14 amino acids, at least about 15 amino acids, at least about 16 amino acids, at least about 17 amino acids, at least about 18 amino acids, at least about 19 amino acids, at least about 20 amino acids, at least about 25 amino acids, or at least about 30 amino acids. In some aspects, the linker is rich in glycine (e.g., for flexibility). In some aspects, the linker comprises serine and/or threonine (e.g., for solubility). In some aspects, the linker is a Gly/Ser linker.

In some aspects, the linker is a non-cleavable linker, such that the linker and the different components of a polynucleotide provided herein (e.g., AP-1 transcription factor and chimeric binding protein) are expressed as a single polypeptide. In certain aspects, the linker is a cleavable linker. As used herein, the term "cleavable linker" refers to a linker that comprises a cleavage site, such that when expressed can be selectively cleaved to produce two or more products. In some aspects, the linker is selected from a P2A linker, a T2A linker, an F2A linker, an E2A linker, a furin cleavage site, or any combination thereof (see Table 4 below). In some aspects, the linker further comprises a GSG linker sequence. In some aspects, a linker useful for the present disclosure comprises an Internal Ribosome Entry Site (IRES), such that separate polypeptides encoded by the first and second genes are produced during translation. Additional description of linkers that can be used with the present disclosure are provided, e.g., in WO 2020/223625 A1 and US 2019/0276801 A1, each of which is incorporated herein by reference in its entirety.

TABLE 4

| | Linker Sequences |
|---|---|
| P2A | ATNFSLLKQAGDVEENPGP (SEQ ID NO: 14) |
| T2A | EGRGSLLTCGDVEENPGP (SEQ ID NO: 15) |
| F2A | VKQTLNFDLLKLAGDVESNPGP (SEQ ID NO: 16) |
| E2A | QCTNYALLKLAGDVESNPGP (SEQ ID NO: 17) |
| Furin Cleavage Site | RAKR (SEQ ID NO: 18) |

In some aspects, the linker comprises a P2A linker. In some aspects, the linker comprises an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 14. In some aspects, the linker comprises the amino acid sequence set forth in SEQ ID NO: 14.

In some aspects, the linker comprises a T2A linker. In some aspects, the linker comprises an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 15. In some aspects, the linker comprises the amino acid sequence set forth in SEQ ID NO: 15.

In some aspects, the linker comprises an F2A linker. In some aspects, the linker comprises an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 16. In some aspects, the linker comprises the amino acid sequence set forth in SEQ ID NO: 16.

In some aspects, the linker comprises an E2A linker. In some aspects, the linker comprises an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 17. In some aspects, the linker comprises the amino acid sequence set forth in SEQ ID NO: 17.

In some aspects, the linker comprises an amino acid sequence comprising a furin cleavage site. In some aspects, the linker comprises an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 18. In some aspects, the linker comprises the amino acid sequence set forth in SEQ ID NO: 18.

Truncated EGFR

In some aspects, a polynucleotide of the present disclosure (e.g., comprising a codon-optimized AP-1 nucleotide sequence) comprises an additional nucleotide sequence encoding a truncated epidermal growth factor receptor (EGFRt), such that the EGFRt comprises only a partial sequence of the full-length EGFR protein (e.g., SEQ ID NO: 19). In some aspects, the EGFRt comprises EGFR extracellular Domains III and IV and an EGFR transmembrane domain, but lacks EGFR extracellular Domains I and II and EGFR intracellular sequence.

EGFR is a 180 kDa monomeric glycoprotein comprising a large extracellular region, a single spanning transmembrane domain, an intracellular juxtamembrane region, a tyrosine kinase domain, and a C-terminal regulatory region. The extracellular region comprises four domains: Domains I and III are homologous ligand binding domains, and domains II and IV are cysteine rich domains (Ferguson, *Annu Rev Biophys*. (2008) 37:353-3). Unless otherwise indicated, EGFR as used herein refers to human EGFR. Due to alternative splicing, there are at least four known isoforms of human EGFR. Sequences for the different EGFR isoforms are provided in Table 5 (below).

TABLE 5

| Human EGFR sequences | |
|---|---|
| Isoform 1 (canonical sequence) (also known as "p170") (UniProt: P00533-1) | MRPSGTAGAALLALLAALCPASRALEEKKVCQGTSNKLTQLGTFEDHFLSLQRMFMNCEV VLGNLEITYVQRNYDLSFLKTIQEVAGYVLIALNTVERIPLENLQIIRGNMYYENSYALA VLSNYDANKTGLKELPMRNLQEILHGAVRFSNNPALCNVESIQWRDIVSSDFLSNMSMDF QNHLGSCQKCDPSCPNGSCWGAGEENCQKLTKIICAQQCSGRCRGKSPSDCCHNQCAAGC TGPRESDCLVCRKFRDEATCKDTCPPLMLYNPTTYQMDVNPEGKYSFGATCVKKCPRNYV VTDHGSCVRACGADSYEMEEDGVRKCKKCEGPCRKVCNGIGIGEFKDSLSINATNIKHFK NCTSISGDLHILPVAFRGDSFTHTPPLDPQELDILKTVKEITGFLLIQAWPENRTDLHAF ENLEIIRGRTKQHGQFSLAVVSLNITSLGLRSLKEISDGDVIISGNKNLCYANTINWKKL FGTSGQKTKIISNRGENSCKATGQVCHALCSPEGCWGPEPRDCVSCRNVSRGRECVDKCN LLEGEPREFVENSECIQCHPECLPQAMNITCTGRGPDNCIQCAHYIDGPHCVKTCPAGVM GENNTLVWKYADAGHVCHLCHPNCTYGCTGPGLEGCPTNGPKIPSIATGMVGALLLLLVV ALGIGLFMRRRHIVRKRTLRRLLQERELVEPLTPSGEAPNQALLRILKETEFKKIKVLGS GAFGTVYKGLWIPEGEKVKIPVAIKELREATSPKANKEILDEAYVMASVDNPHVCRLLGI CLTSTVQLITQLMPFGCLLDYVREHKDNIGSQYLLNWCVQIAKGMNYLEDRRLVHRDLAA RNVLVKTPQHVKITDFGLAKLLGAEEKEYHAEGGKVPIKWMALESILHRIYTHQSDVWSY GVTVWELMTFGSKPYDGIPASEISSILEKGERLPQPPICTIDVYMIMVKCWMIDADSRPK FRELIIEFSKMARDPQRYLVIQGDERMHLPSPTDSNFYRALMDEEDMDDVVDADEYLIPQ QGFFSSPSTSRTPLLSSLSATSNNSTVACIDRNGLQSCPIKEDSFLQRYSSDPTGALTED SIDDTFLPVPEYINQSVPKRPAGSVQNPVYHNQPLNPAPSRDPHYQDPHSTAVGNPEYLN TVQPTCVNSTFDSPAHWAQKGSHQISLDNPDYQQDFFPKEAKPNGIFKGSTAENAEYLRV APQSSEFIGA (SEQ ID NO: 19) |
| Isoform 2 (also known as "p60") (UniProt: P00533-2) | MRPSGTAGAALLALLAALCPASRALEEKKVCQGTSNKLTQLGTFEDHFLSLQRMFMNCEV VLGNLEITYVQRNYDLSFLKTIQEVAGYVLIALNTVERIPLENLQIIRGNMYYENSYALA VLSNYDANKTGLKELPMRNLQEILHGAVRFSNNPALCNVESIQWRDIVSSDFLSNMSMDF QNHLGSCQKCDPSCPNGSCWGAGEENCQKLTKIICAQQCSGRCRGKSPSDCCHNQCAAGC TGPRESDCLVCRKFRDEATCKDTCPPLMLYNPTTYQMDVNPEGKYSFGATCVKKCPRNYV VTDHGSCVRACGADSYEMEEDGVRKCKKCEGPCRKVCNGIGIGEFKDSLSINATNIKHFK NCTSISGDLHILPVAFRGDSFTHTPPLDPQELDILKTVKEITGLS (SEQ ID NO: 20) |
| Isoform 3 (also known as "p110") (UniProt: P00533-3) | MRPSGTAGAALLALLAALCPASRALEEKKVCQGTSNKLTQLGTFEDHFLSLQRMFMNCEV VLGNLEITYVQRNYDLSFLKTIQEVAGYVLIALNTVERIPLENLQIIRGNMYYENSYALA VLSNYDANKTGLKELPMRNLQEILHGAVRFSNNPALCNVESIQWRDIVSSDFLSNMSMDF QNHLGSCQKCDPSCPNGSCWGAGEENCQKLTKIICAQQCSGRCRGKSPSDCCHNQCAAGC TGPRESDCLVCRKFRDEATCKDTCPPLMLYNPTTYQMDVNPEGKYSFGATCVKKCPRNYV VTDHGSCVRACGADSYEMEEDGVRKCKKCEGPCRKVCNGIGIGEFKDSLSINATNIKHFK NCTSISGDLHILPVAFRGDSFTHTPPLDPQELDILKTVKEITGFLLIQAWPENRTDLHAF ENLEIIRGRTKQHGQFSLAVVSLNITSLGLRSLKEISDGDVIISGNKNLCYANTINWKKL |

TABLE 5-continued

Human EGFR sequences

| | |
|---|---|
| | FGTSGQKTKIISNRGENSCKATGQVCHALCSPEGCWGPEPRDCVSCRNVSRGRECVDKCN<br>LLEGEPREFVENSECIQCHPECLPQAMNITCTGRGPDNCIQCAHYIDGPHCVKTCPAGVM<br>GENNTLVWKYADAGHVCHLCHPNCTYGPGNESLKAMLFCLFKLSSCNQSNDGSVSHQSGS<br>PAAQESCLGWIPSLLPSEFQLGWGGCSHLHAWPSASVIITASSCH (SEQ ID NO: 21) |
| Isoform 4<br>(UniProt:<br>P00533-4) | MRPSGTAGAALLALLAALCPASRALEEKKVCQGTSNKLTQLGTFEDHFLSLQRMFNNCEV<br>VLGNLEITYVQRNYDLSFLKTIQEVAGYVLIALNTVERIPLENLQIIRGNMYYENSYALA<br>VLSNYDANKTGLKELPMRNLQEILHGAVRFSNNPALCNVESIQWRDIVSSDFLSNMSMDF<br>QNHLGSCQKCDPSCPNGSCWGAGEENCQKLTKIICAQQCSGRCRGKSPSDCCHNQCAAGC<br>TGPRESDCLVCRKFRDEATCKDTCPPLMLYMPTTYQMDVNPEGKYSFGATCVKKCPRNYV<br>VTDHGSCVRACGADSYEMEEDGVRKCKKCEGPCRKVCNGIGIGEFKDSLSINATNIKHFK<br>NCTSISGDLHILPVAFRGDSFTHTPPLDPQELDILKTVKEITGFLLIQAWPENRTDLHAF<br>ENLEIIRGRTKQHGQFSLAVVSLNITSLGLRSLKEISDGDVIISGNKNLCYANTINWKKL<br>FGTSGQKTKIISNRGENSCKATGQVCHALCSPEGCWGPEPRDCVSCRNVSRGRECVDKCN<br>LLEGEPREFVENSECIQCHPECLPQAMNITCTGRGPDNCIQCAHYIDGPHCVKTCPAGVM<br>GENNTLVWKYADAGHVCHLCHPNCTYGS (SEQ ID NO: 22) |

In the above canonical sequence for EGFR (i.e., isoform 1), the various EGFR domains are delineated as follows. The signal peptide spans amino acids 1-24. The extracellular sequence spans amino acids 25-645, wherein Domain I, Domain II, Domain III, and Domain IV span amino acids 25-188, 189-333, 334-504, and 505-645, respectively. The transmembrane domain spans amino acids 646-668. The intracellular domain spans amino acids 669-1,210, where the juxtamembrane domain spans amino acids 669-703 and the tyrosine kinase domain spans amino acids 704-1,210.

In some aspects, the EGFRt useful for the present disclosure comprises an amino acid sequence having at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 19.

In some aspects, the EGFRt that can be used with the present disclosure comprises an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 23. In certain aspects, the EGFRt comprises the amino acid sequence set forth in SEQ ID NO: 23 (see Table 6). In some aspects, the EGFRt that can be used with the present disclosure comprises an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 24. In certain aspects, the EGFRt comprises the amino acid sequence set forth in SEQ ID NO: 24 (see Table 6).

TABLE 6

Truncated EGFR sequences

| | |
|---|---|
| EGFRt | RKVCNGIGIGEFKDSLSINATNIKHFKNCTSISGDLHILPVAFRGDSFTHTPPLD<br>PQELDILKTVKEITGFLLIQAWPENRTDLHAFENLEIIRGRTKQHGQFSLAVVSL<br>NITSLGLRSLKEISDGDVIISGNKNLCYANTINWKKLFGTSGQKTKIISNRGENS<br>CKATGQVCHALCSPEGCWGPEPRDCVSCRNVSRGRECVDKCNLLEGEPREFVENS<br>ECIQCHPECLPQAMNITCTGRGPDNCIQCAHYIDGPHCVKTCPAGVMGENNTLVW<br>KYADAGHVCHLCHPNCTYGCTGPGLEGCPTNGPKIPSIATGMVGALLLLLVVALG<br>IGLFM (SEQ ID NO: 23) |
| EGFRt + first 3<br>amino acids of the<br>intracellular domain<br>of human EGFR | RKVCNGIGIGEFKDSLSINATNIKHEKNCTSISGDLHILPVAFRGDSFTHTPPLD<br>PQELDILKTVKEITGELLIQAWPENRTDLHAFENLEIIRGRTKQHGQFSLAVVSL<br>NITSLGLRSLKEISDGDVIISGNKNLCYANTINWKKLEGTSGQKTKIISNRGENS<br>CKATGQVCHALCSPEGCWGPEPRDCVSCRNVSRGRECVDKCNLLEGEPREFVENS<br>ECIQCHPECLPQAMNITCTGRGPDNCIQCAHYIDGPHCVKTCPAGVMGENNTLVW<br>KYADAGHVCHLCHPNCTYGCTGPGLEGCPTNGPKIPSIATGMVGALLLLLVVALG<br>IGLFMRRR (SEQ ID NO: 24) |

In some aspects, the EGFRt described herein additionally comprises a juxtamembrane domain. As used herein, the term "juxtamembrane domain" refers to an intracellular portion of a cell surface protein (e.g., EGFR) immediately C-terminal to the transmembrane domain. Not to be bound by any one theory, in some aspects, the addition of the juxtamembrane domain can increase the expression of the protein encoded by the polynucleotides of the present disclosure.

In some aspects, the juxtamembrane domain can be from about 1 to about 20 (e.g., 2-20, 3-20, 4-20, 5-20, 2-18, 3-18, 4-18, or 5-18) amino acids long. In certain aspects, the juxtamembrane domain can be longer than 20 amino acids. In some aspects, the first 1 or more (e.g., first 2, 3, 4, 5, 6, 7, 8, 9, 10, 11, 12, 13, 14, 15, 16, 17, 18, 19, or 20) amino acids of the juxtamembrane domain is a net-neutral or net-positively charged sequence (e.g., the number of arginine and lysine residues is greater than or equal to the number of aspartic acid and glutamic acid residues). In certain aspects, those first amino acids contain more than about 30% (e.g., more than 40, 50, 60, 70, 80, or 90%) hydrophilic amino acids. Non-limiting examples of juxtamembrane domains that are useful for the present disclosure are provided in Table 7 (below).

TABLE 7

Juxtamembrane domain sequences

| Net charge | Sequence |
|---|---|
| +1 | K |
| +2 | KR |
| +3 | KRK |
| +2 | KSR |
| +1 | KSGSGS (SEQ ID NO: 25) |
| +2 | SKR |
| +1 | KRSD (SEQ ID NO: 26) |
| +2 | KRSDK (SEQ ID NO: 27) |
| 0 | SGGGG (SEQ ID NO: 28) |
| 0 | SGAGG (SEQ ID NO: 29) |
| +2 | KRADK (SEQ ID NO: 30) |
| +3 | RRRSGGGGSGGGGS (SEQ ID NO: 31) |
| 0 | SGGGGSGGGGS (SEQ ID NO: 32) |
| 0 | (GGGGS)n, n > 1 (SEQ ID NO: 33) |

In some aspects, the juxtamembrane domain that can be used with the present disclosure can be derived from the juxtamembrane region of a natural cell surface protein, such as a juxtamembrane region (e.g., the entire or partial sequence of the first 20 juxtamembrane amino acids) of a human receptor tyrosine kinase that interacts with phosphatidylcholine (PC), phosphatidylserine (PS), or phosphatidylinositol-4,5-bisphosphate (PIP2) (see, e.g., Hedger et al., Sci Rep. (2015) 5: 9198). Non-limiting examples of receptor tyrosine kinases are ERBB1 (EGFR), ERBB2 (HER2), ERBB3 (HER3), ERBB4 (HER4), INSR, IGF1R, INSRR, PGFRA, PGFRB, KIT, CSF1R, FLT3, VGFR1, VGFR2, VGFR3, FGFR1, FGFR2, FGFR3, FGFR4, PTK7, NTRK1, NTRK2, NTRK3, ROR1, ROR2, MUSK, MET, RON, UFO, TYRO3, MERTK, TIE1, TIE2, EPHA1, EPHA2, EPHA3, EPHA4, EPHA5, EPHA6, EPHA7, EPHA8, EPHAA, EPHB1, EPHB2, EPHB3, EPHB4, EPHB6, RET, RYK, DDR1, DDR2, ROS1, LMTK1, LMTK2, LMTK3, LTK, ALK, and STYK1. In certain aspects, the juxtamembrane domain can comprise one or more mutations (e.g., substitutions or deletions) that remove residues known to be phosphorylated so as to circumvent any unintended signal transducing ability of the protein encoded by the polynucleotides of the present disclosure.

In some aspects, the juxtamembrane domain is derived from a juxtamembrane region of EGFR. Non-limiting examples of EGFR-derived juxtamembrane domains comprise one of the sequences provided in Table 8 (below). In certain aspects, the juxtamembrane domain comprises the amino acid sequence RRR. In certain aspects, an EGFRt comprising such a juxtamembrane domain comprises the sequence set forth in SEQ ID NO: 22.

TABLE 8

EGFR-derived juxtamembrane domain sequences

| Net charge | Sequence |
|---|---|
| +6 | RRRHIVRKR (SEQ ID NO: 34) |
| +5 | RRRHIVRK (SEQ ID NO: 35) |
| +4 | RRRHIVR (SEQ ID NO: 36) |
| +3 | RRRHIV (SEQ ID NO: 37) |
| +3 | RRRHI (SEQ ID NO: 38) |
| +3 | RRRH (SEQ ID NO: 39) |
| +3 | RRR |
| +2 | RR |
| +1 | R |

As is apparent from the present disclosure, the inclusion of a nucleotide sequence encoding EGFRt provides the polynucleotides of the present disclosure (e.g., comprising a codon-optimized c-Jun nucleotide sequence and a nucleotide sequence encoding a chimeric binding protein) certain advantages. For instance, in some aspects, the EGFRt can function as a kill switch. When the engineered cells (e.g., CAR T cells transduced with a polynucleotide described herein) are no longer needed in the body, a pharmaceutical grade anti-EGFR antibody such as cetuximab, panitumumab, nimotuzumab, or necitumumab can be administered to a subject who had received the engineered cells, thereby removing the engineered cells, e.g., through antibody-dependent cellular cytotoxicity (ADCC), complement-dependent cytotoxicity (CDC), and/or antibody-dependent cellular phagocytosis (ADCP).

In some aspects, a polynucleotide of the present disclosure comprises a first nucleotide sequence encoding an AP-1 transcription factor, a second nucleotide sequence encoding a chimeric binding protein (e.g., CAR), and a third nucleotide sequence encoding a EGFRt. In certain aspects, the polynucleotide additionally comprises a fourth nucleotide sequence encoding a first linker, wherein the fourth nucleotide sequence is between the first and second nucleotide sequences, such that the AP-1 transcription factor is linked to the chimeric binding protein by the first linker. In certain aspects, the polynucleotide further comprises a fifth nucleotide sequence encoding a second linker, wherein the fifth nucleotide sequence is between the second and third nucleotide sequences, such that the chimeric binding protein is linked to the EGFRt by the second linker. In some aspects, the first linker and the second linker are the same. In certain aspects, the first and second linkers are different. Any of the linkers described herein (e.g., P2A linker) can be used as the second linker.

Spacers

In some aspects, a polynucleotide of the present disclosure (e.g., comprising a codon-optimized AP-1 nucleotide sequence) comprises a nucleotide sequence encoding a spacer. As used herein, the term "spacer" refers to a polypeptide sequence which is capable of covalently linking together two spaced moieties (e.g., P2A linker and a chimeric binding protein).

In certain aspects, the spacer is derived from an immunoglobulin (e.g., derived from hinge regions or loop regions). In some aspects, the spacer comprises IgA1, IgA2, IgG1, IgG2, IgG3, IgG4, IgD, IgE, or IgM hinge regions, fragments thereof (alone or capped by additional sequences, e.g., CH1 or CH2 regions sequences), or combinations of fragments from IgA1, IgA2, IgG1, IgG2, IgG3, IgG4, IgD, IgE, or IgM hinge regions (referred to herein as a "hinge region derived spacer"). In some aspects, the spacer comprises IgA1, IgA2, IgG1, IgG2, IgG3, IgG4, IgD, IgE, or IgM constant domain loop regions, fragments thereof (alone or capped by additional sequences, e.g., from adjacent β-strands), or combinations of fragments from IgA1, IgA2, IgG1, IgG2, IgG3, IgG4, IgD, IgE, or IgM loop regions (referred to herein as a "loop region derived spacer"). In certain aspects, the spacer comprises hinge region derived spacer, loop region derived spacer, or both (e.g., two or more concatenated hinge region derived spacers and loop region derived spacers).

Accordingly, in some aspects, a polynucleotide of the present disclosure encodes a polypeptide comprising (i) an AP-1 transcription factor, (ii) a first linker (e.g., P2A linker), (iii) signal peptide (e.g., hIgκ), (iv) antigen-binding domain (e.g., scFv), (v) a second linker (e.g., GGGSG; SEQ ID NO: 40), (vi) a spacer (e.g., IgG2 hinge derived spacer), (vii) a transmembrane domain (e.g., CD28), (viii) a costimulatory domain (e.g., 4-1BB), (ix) an intracellular signaling domain (e.g., CD3ζ), (x) a third linker (e.g., P2A linker), and (xi) a EGFRt.

In some aspects, a spacer useful for the present disclosure comprises a subsequence of an immunoglobulin heavy chain selected the group consisting of human IgA1 (Uniprot: P01876, IGHA1_HUMAN, immunoglobulin heavy constant alpha 1; SEQ ID NO: 41), human IgA2 (Uniprot P01877, IGHA2_HUMAN, immunoglobulin heavy constant alpha 2; SEQ ID NO: 42), murine IgG2A (Uniprot P01665, GCAM_MOUSE, immunoglobulin gamma 2A chain C region; SEQ ID NO: 43), human IgG1 (Uniprot P01857, IGHG1_HUMAN, immunoglobulin heavy constant gamma 1; SEQ ID NO: 44), human IgG2 (Uniprot P01859, IGHG2_HUMAN, immunoglobulin heavy constant gamma 2; SEQ ID NO: 45), human IgG3 (Uniprot P01860, IGHG3_HUMAN, immunoglobulin heavy constant gamma 3; SEQ ID NO: 46), human IgG4 (Uniprot P01861, IGHG4, immunoglobulin heavy constant gamma 4; SEQ ID NO: 47), human IgD (Uniprot P01880, IGHD_HUMAN, immunoglobulin heavy constant delta; SEQ ID NO: 48), human IgE (Uniprot P01854, IGHE_HUMAN, immunoglobulin heavy constant chain epsilon; SEQ ID NO: 49), or IgM (Uniprot P01871, IGHM_HUMAN, immunoglobulin heavy constant mu; SEQ ID NO: 50), wherein the subsequence comprises the CH1-CH2 hinge region or a portion thereof. In some aspects, the subsequence further comprises an adjacent portion of a CH1 and/or CH2 constant domain.

In some aspects, a spacer comprises a subsequence of an immunoglobulin heavy chain selected the group consisting of human IgA1 (Uniprot: P01876, IGHA1_HUMAN, immunoglobulin heavy constant alpha 1; SEQ ID NO: 41), human IgA2 (Uniprot P01877, IGHA2_HUMAN, immunoglobulin heavy constant alpha 2; SEQ ID NO: 42), murine IgG2A (Uniprot P01665, GCAM_MOUSE, immunoglobulin gamma 2A chain C region; SEQ ID NO: 43), human IgG1 (Uniprot P01857, IGHG1_HUMAN, immunoglobulin heavy constant gamma 1; SEQ ID NO: 44), human IgG2 (Uniprot P01859, IGHG2_HUMAN, immunoglobulin heavy constant gamma 2; SEQ ID NO: 45), human IgG3 (Uniprot P01860, IGHG3_HUMAN, immunoglobulin heavy constant gamma 3; SEQ ID NO: 46), human IgG4 (Uniprot P01861, IGHG4, immunoglobulin heavy constant gamma 4; SEQ ID NO: 47), human IgD (Uniprot P01880, IGHD_HUMAN, immunoglobulin heavy constant delta; SEQ ID NO: 48), human IgE (Uniprot P01854, IGHE_HUMAN, immunoglobulin heavy constant chain epsilon; SEQ ID NO: 49), or IgM (Uniprot P01871, IGHM_HUMAN, immunoglobulin heavy constant mu; SEQ ID NO: 50), wherein the subsequence comprises a loop region from a constant domain or a portion thereof. In some aspects, the subsequence further comprises an adjacent portion of a β-strand.

In some aspects, a spacer useful for the present disclosure is derived from an IgG, e.g., IgG1, IgG2, IgG3, or IgG4. In certain aspects, the spacer is derived from an IgG2 hinge. In some aspects, the IgG2 hinge derived spacer comprises at least five, six, or seven consecutive amino acids of SEQ ID NO: 51 (KPCPPCKCP). In some aspects, the spacer comprises an amino acid sequence that is at least about 70%, at least about 75%, at least about 80%, at least about 85%, at least about 90%, at least about 95%, at least about 96%, at least about 97%, at least about 98%, at least about 99%, or about 100% identical to the sequence set forth in SEQ ID NO: 51 (KPCPPCKCP). In certain aspects, the spacer comprises, consists, or consists essentially of the sequence set forth in SEQ ID NO: 51 (KPCPPCKCP). In further aspects, the spacer comprises the sequence set forth in SEQ ID NO: 51 (KPCPPCKCP) except for one, 2, 3, 4, 5, 6, 7, 8, 9, or 10 amino acid substitutions. In some aspects, the amino acid substitutions are conservative amino acid substitutions. In some aspects, the amino acid substitution comprises at least one non-conservative amino acid substitution.

In some aspects, a spacer of the present disclosure comprises of the sequence set forth in SEQ ID NO: 51, wherein the spacer sequence further comprises an optional flexible linker (e.g., the linker of GGGSG (SEQ ID NO: 40)). Thus, in some aspects, a spacer of the present disclosure comprises a spacer sequence (e.g., SEQ ID NO: 51) and an optional C-terminal or N-terminal flexible linker. In some aspects, any optional flexible linkers (e.g., gly/ser rich linker) disclosed herein can be appended to the C-terminus and/or the N-terminus of a spacer.

Signal Peptide

As described herein, in some aspects, a polynucleotide of the present disclosure (e.g., comprising a codon-optimized AP-1 nucleotide sequence) also comprises a nucleotide sequence encoding a signal peptide. The signal peptide can facilitate the cell surface expression of the encoded protein and then can be subsequently cleaved from the mature protein.

Any suitable signal peptide known in the art can be used with the present disclosure. Non-limiting examples of signal peptides are provided in Table 9 (below). In certain aspects, the signal peptide is derived from human Ig kappa. In some aspects, the signal peptide comprises an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 54 (MVLQTQVFISLLLWISGAYG). In certain aspects, the signal peptide comprises the amino acid sequence set forth in SEQ ID NO: 54 (MVLQTQVFISLLL-WISGAYG). In some aspects, the signal peptide is derived from GM-CSF. In certain aspects, such a signal peptide comprises an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 53 (MLLLVTSLLL-CELPHPAFLLIP). In some aspects, the signal peptide comprises the amino acid sequence set forth in SEQ ID NO: 53 (MLLLVTSLLLCELPHPAFLLIP).

TABLE 9

Signal Peptide Sequences

| Source | Sequence |
|---|---|
| EGFR | MRPSGTAGAALLALLAALCPASRA (SEQ ID NO: 52) |
| GM-CSF | MLLLVTSLLLCELPHPAFLLIP (SEQ ID NO: 53) |
| human Ig kappa | MVLQTQVFISLLLWISGAYG (SEQ ID NO: 54) |
| human CD33 | MPLLLLLPLLWAGALA (SEQ ID NO: 55) |

In some aspects, a polynucleotide described herein comprises a single signal peptide (e.g., SEQ ID NO: 53 or 54). In some aspects, the polynucleotide comprises multiple signal peptides (e.g., at least two, three, four, or more). Accordingly, in some aspects, a polynucleotide of the present disclosure encodes a polypeptide comprising (i) an AP-1 transcription factor, (ii) a first linker (e.g., P2A linker), (iii) a first signal peptide (e.g., hIgκ), (iv) antigen-binding domain (e.g., scFv), (v) a second linker (e.g., GGGSG; SEQ ID NO: 40), (vi) a spacer (e.g., IgG2 hinge derived spacer), (vii) a transmembrane domain (e.g., CD28), (viii) a costimulatory domain (e.g., 4-1BB), (ix) an intracellular signaling domain (e.g., CD3), (x) a third linker (e.g., P2A linker), (xi) a second signal peptide (e.g., GM-CSF), and (xii) a EGFRt.

Vectors

In some aspects, provided herein are vectors (e.g., expression vectors) comprising a polynucleotide described herein (e.g., comprising a nucleotide sequence encoding an AP-1 transcription factor, e.g., codon-optimized nucleotide sequence). In some aspects, a vector described herein comprises multiple (e.g., 2, 3, or 4 or more) polynucleotides, wherein the multiple polynucleotides each encode a protein described herein (e.g., AP-1 transcription factor, ligand binding protein (e.g., chimeric binding protein, e.g., CAR), or EGFRt). Accordingly, in certain aspects, a vector comprises a polycistronic vector (e.g., bicistronic vector or tricistronic vector). In certain aspects, the polynucleotides described herein are comprised on the same vector (e.g., on a multicistronic expression vector). In certain aspects, the polynucleotides encoding the proteins described herein (e.g., AP-1 transcription factor, ligand binding protein (e.g., chimeric binding protein, e.g., CAR), or EGFRt) are provided on one or more separate vectors.

As described herein, such vectors are useful for recombinant expression in host cells and cells targeted for therapeutic intervention. The term "vector," as used herein, is intended to refer to a nucleic acid molecule capable of transporting another nucleic acid to which it has been linked; or an entity comprising such a nucleic acid molecule capable of transporting another nucleic acid. In some aspects, the vector is a "plasmid," which refers to a circular double stranded DNA loop into which additional DNA segments can be ligated. In some aspects, the vector is a viral vector, wherein additional DNA segments can be ligated into the viral genome. Certain vectors, or polynucleotides that are part of vectors, are capable of autonomous replication in a host cell into which they are introduced (e.g., bacterial vectors having a bacterial origin of replication, and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present disclosure, "plasmid" and "vector" can sometimes be used interchangeably, depending on the context, as the plasmid is the most commonly used form of vector. However, also disclosed herein are other forms of expression vectors, such as viral vectors (e.g., lentiviruses, replication defective retroviruses, poxviruses, herpesviruses, baculoviruses, adenoviruses, and adeno-associated viruses), which serve equivalent functions.

In some aspects, a vector comprises a polynucleotide described herein (e.g., comprising a codon-optimized AP-1 nucleotide sequence) and a regulatory element. For instance, in certain aspects, a vector comprises a polynucleotide described herein (e.g., comprising a codon-optimized AP-1 nucleotide sequence), operatively linked to a promoter. In some aspects, the vector can comprise multiple promoters (e.g., at least two, at least three, at least four, at least five or more). For instance, in some aspects, the nucleotide sequence encoding the AP-1 transcription factor (e.g., codon-optimized AP-1 nucleotide sequence) can be under the control of a first promoter, and the nucleotide sequence encoding one or more of the additional components of the polynucleotide (e.g., chimeric binding protein) can be under the control of a second promoter. In certain aspects, each of the multiple promoters are the same. In some aspects, one or more of the multiple promoters are different.

Any suitable promoter known in the art can be used with the present disclosure. In some aspects, the promoters useful for the present disclosure comprises a mammalian or viral promoter, such as a constitutive or inducible promoter. In some aspects, the promoters for the present disclosure comprises at least one constitutive promoter and at least one inducible promoter, e.g., tissue specific promoter.

Constitutive mammalian promoters include, but are not limited to, the promoters for the following genes: hypoxanthine phosphoribosyl transferase (HPRT), adenosine deaminase, pyruvate kinase, beta-actin promoter, and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus, and other retroviruses, and the thymidine kinase promoter of herpes simplex virus. As described herein, in some aspects, promoters that can be used with the present disclosure are inducible promoters. Inducible promoters are expressed in the presence of an inducing agent. For example, the metallothionein promoter is induced to promote transcription and translation in the presence of certain metal ions. When multiple inducible promoters are present, they can be induced by the same inducer molecule or a different inducer.

In some aspects, the promoter comprises a myeloproliferative sarcoma virus enhancer, negative control region deleted, d1587rev primer-binding site substituted (MND) promoter, EF1a promoter, or both.

In some aspects, a vector comprising any of the polynucleotides of the present disclosure (e.g., comprising a codon-optimized AP-1 nucleotide sequence) further comprises one or more additional regulatory elements. Non-limiting examples of regulatory elements include a translation enhancer element (TEE), a translation initiation sequence, a microRNA binding site or seed thereof, a 3' tailing region of linked nucleosides, an AU rich element (ARE), a post transcription control modulator, a 5' UTR, a 3' UTR, a localization sequence (e.g., membrane-localization sequences, nuclear localization sequences, nuclear exclusion sequences, or proteasomal targeting sequences), post-translational modification sequences (e.g., ubiquitination, phosphorylation, or dephosphorylation), or combinations thereof.

In some aspects, the vector can additionally comprise a transposable element. Accordingly, in certain aspects, the vector comprises a polynucleotide described herein (e.g., comprising a codon-optimized AP-1 nucleotide sequence), which is flanked by at least two transposon-specific inverted terminal repeats (ITRs). In some aspects, the transposon-specific ITRs are recognized by a DNA transposon. In some aspects, the transposon-specific ITRs are recognized by a retrotransposon. Any transposon system known in the art can be used to introduce the nucleic acid molecules into the genome of a host cell, e.g., an immune cell. In some aspects, the transposon is selected from hAT-like Tol2, Sleeping Beauty (SB), Frog Prince, piggyBac (PB), and any combination thereof. In some aspects, the transposon comprises Sleeping Beauty. In some aspects, the transposon comprises piggyBac. See, e.g., Zhao et al., *Transl. Lung Cancer Res.* 5(1):120-25 (2016), which is incorporated by reference herein in its entirety.

In some aspects, the vector is a transfer vector. The term "transfer vector" refers to a composition of matter which comprises an isolated nucleic acid (e.g., a polynucleotide of the present disclosure) and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

In some aspects, the vector is an expression vector. The term "expression vector" refers to a vector comprising a recombinant polynucleotide (e.g., a polypeptide of the present disclosure) comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

In some aspects, the vector is a viral vector, a mammalian vector, or bacterial vector. In some aspects, the vector is selected from the group consisting of an adenoviral vector, a lentivirus, a Sendai virus vector, a baculoviral vector, an Epstein Barr viral vector, a papovaviral vector, a vaccinia viral vector, a herpes simplex viral vector, a hybrid vector, and an adeno associated virus (AAV) vector.

In some aspects, the adenoviral vector is a third generation adenoviral vector. ADEASY™ is by far the most popular method for creating adenoviral vector constructs. The system consists of two types of plasmids: shuttle (or transfer) vectors and adenoviral vectors. The transgene of interest is cloned into the shuttle vector, verified, and linearized with the restriction enzyme PmeI. This construct is then transformed into ADEASIER-1 cells, which are BJ5183 *E. coli* cells containing PADEASY™. PADEASY™ is a ~33 Kb adenoviral plasmid containing the adenoviral genes necessary for virus production. The shuttle vector and the adenoviral plasmid have matching left and right homology arms which facilitate homologous recombination of the transgene into the adenoviral plasmid. One can also co-transform standard BJ5183 with supercoiled PADEASY™ and the shuttle vector, but this method results in a higher background of non-recombinant adenoviral plasmids. Recombinant adenoviral plasmids are then verified for size and proper restriction digest patterns to determine that the transgene has been inserted into the adenoviral plasmid, and that other patterns of recombination have not occurred. Once verified, the recombinant plasmid is linearized with PacI to create a linear dsDNA construct flanked by ITRs. 293 or 911 cells are transfected with the linearized construct, and virus can be harvested about 7-10 days later. In addition to this method, other methods for creating adenoviral vector constructs known in the art at the time the present application was filed can be used to practice the methods disclosed herein.

In some aspects, the viral vector is a retroviral vector, e.g., a lentiviral vector (e.g., a third or fourth generation lentiviral vector). The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. The term "lentiviral vector" refers to a vector derived from at least a portion of a lentivirus genome, including especially a self-inactivating lentiviral vector as provided in Milone et al., *Mol. Ther* 17(8): 1453-1464 (2009). Other examples of lentivirus vectors that may be used in the clinic, include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

Lentiviral vectors are usually created in a transient transfection system in which a cell line is transfected with three separate plasmid expression systems. These include the transfer vector plasmid (portions of the HIV provirus), the packaging plasmid or construct, and a plasmid with the heterologous envelop gene (env) of a different virus. The three plasmid components of the vector are put into a packaging cell which is then inserted into the HIV shell. The virus portions of the vector contain insert sequences so that the virus cannot replicate inside the cell system. Current third generation lentiviral vectors encode only three of the nine HIV-1 proteins (Gag, Pol, Rev), which are expressed from separate plasmids to avoid recombination-mediated generation of a replication-competent virus. In fourth generation lentiviral vectors, the retroviral genome has been further reduced (see, e.g., TAKARA® LENTI-X™ fourth-generation packaging systems).

In some aspects, non-viral methods can be used to deliver a polynucleotide of the present disclosure (e.g., comprising a codon-optimized AP-1 nucleotide sequence and a nucleotide sequence encoding a chimeric binding protein) into a cell or tissue of a subject. In some aspects, the non-viral method includes the use of a transposon. In some aspects, use of a non-viral method of delivery permits reprogramming of cells, e.g., T or NK cells, and direct infusion of the cells into the subject. In some aspects, a polynucleotide of the present disclosure (e.g., comprising a codon-optimized AP-1 nucleotide sequence and a nucleotide sequence encoding a chimeric binding protein) can be inserted into the genome of a target cell (e.g., a T cell) or a host cell (e.g., a cell for recombinant expression of the encoded proteins) by using CRISPR/Cas systems and genome edition alternatives such as zinc-finger nucleases (ZFNs), transcription activator-like effector nucleases (TALENs), and meganucleases (MNs).

In some aspects, the vector disclosed herein (e.g., lentiviral vector) comprises a polynucleotide comprising one or more nucleotide sequences, which encode (i) an AP-1 transcription factor (e.g., codon-optimized AP-1 nucleotide sequence) and (ii) an antigen-binding domain (e.g., anti-ROR1 scFv). In some aspects, the vector comprises a polynucleotide comprising one or more nucleotide sequences, which encode (i) an AP-1 transcription factor (e.g., codon-optimized AP-1 nucleotide sequence), (ii) an antigen-binding domain (e.g., anti-ROR1 scFv), and (iii) EGFRt. In some aspects, the vector comprises a polynucleotide comprising one or more nucleotide sequences, which encode (i) an AP-1 transcription factor (e.g., codon-optimized AP-1 nucleotide sequence), (ii) an antigen-binding domain (e.g., anti-ROR1 scFv), (iii) a transmembrane domain (e.g., CD28), (iv) a costimulatory domain (4-1BB), (v) an intracellular signaling domain (CD3), and (vi) a EGFRt. In certain aspects, the one or more nucleotide sequences additionally encode a linker, spacer, signal peptide, or combinations thereof. For instance, in some aspects, a vector described herein comprises a polynucleotide, which comprises (from 5' to 3') (i) a first nucleotide sequence encoding an AP-1 transcription factor (e.g., codon-optimized AP-1 nucleotide sequence), (ii) a second nucleotide sequence encoding a first linker (e.g., P2A linker), (iii) a third nucleotide sequence encoding a first signal peptide (e.g., hIgκ), (iv) a fourth nucleotide sequence encoding an antigen-binding domain (e.g., anti-ROR1 scFv), (v) a fifth nucleotide sequence encoding a second linker (e.g., GGGSG; SEQ ID NO: 40), (vi) a sixth nucleotide sequence encoding a spacer (e.g., IgG2 hinge derived spacer), (vii) a seventh nucleotide sequence encoding a transmembrane domain (e.g., CD28), (viii) an eighth nucleotide sequence encoding a costimulatory domain (e.g., 4-1BB), (ix) a ninth nucleotide sequence encoding an intracellular signaling domain (e.g., CD3ζ), (x) a tenth nucleotide sequence encoding a third linker (e.g., P2A linker), (xi) an eleventh nucleotide sequence encoding a second signal peptide (e.g., GM-CSF), and (xii) a twelfth nucleotide sequence encoding a EGFRt.

In some aspects, the polynucleotides disclosed herein (e.g., comprising a codon-optimized AP-1 nucleotide sequence) are DNA (e.g., a DNA molecule or a combination thereof), RNA (e.g., a RNA molecule or a combination thereof), or any combination thereof. In some aspects, the polynucleotides disclosed herein comprise nucleic acid sequences comprising single stranded or double stranded RNA or DNA (e.g., ssDNA or dsDNA) in genomic or cDNA form, or DNA-RNA hybrids, each of which can include chemically or biochemically modified, non-natural, or derivatized nucleotide bases. As described herein, such nucleic acid sequences can comprise additional sequences useful for promoting expression and/or purification of the encoded polypeptide, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleotide sequences will encode the different polypeptides described herein (e.g., AP-1 transcription factor or chimeric binding protein).

Cells

In some aspects, provided herein are cells (e.g., immune cells, e.g., T cells) that have been modified (e.g., genetically) to comprise any of the polynucleotides, vectors, compositions, polypeptides, or set of polypeptides described herein. Accordingly, in some aspects, a modified cell described herein overexpresses an AP-1 transcription factor. As described elsewhere in the present disclosure, the overexpression of the AP-1 transcription factor can improve and/or enhance one or more properties of the cells (e.g., resistance to exhaustion, persistence/survival, expansion/proliferation, effector function (e.g., cytokine production upon antigen stimulation, lysis of cells expressing the target antigen, or both), or combinations thereof). In some aspects, the modified cells further express one or more proteins encoded by the additional translational sequences described herein (e.g., chimeric binding proteins, linkers, EGFRt, spacers, signal peptides, or combinations thereof).

In some aspects, a modified cell disclosed herein has been transfected with a polynucleotide or vector described herein. The term "transfected" (or equivalent terms "transformed" and "transduced") refers to a process by which exogenous nucleic acid, e.g., a polynucleotide or vector described herein, is transferred or introduced into the genome of the host cell, e.g., a T cell. A "transfected" cell is one which has been transfected, transformed or transduced with exogenous nucleic acid, e.g., a polynucleotide or vector described herein. The cell includes the primary subject cell and its progeny.

In some aspects, a cell described herein has been modified with a transcriptional activator, which is capable of inducing and/or increasing the endogenous expression of a protein of interest (e.g., c-Jun) in the cell. As used herein, the term "transcriptional activator" refers to a protein that increases the transcription of a gene or set of genes (e.g., by binding to enhancers or promoter-proximal elements of a nucleic acid sequence and thereby, inducing its transcription). Non-limiting examples of such transcriptional activators that can be used with the present disclosure include: Transcription Activator-like Effector (TALE)-based transcriptional activator, zinc finger protein (ZFP)-based transcriptional activator, Clustered Regularly Interspaced Short Palindromic Repeats (CRISPR)/CRISPR-associated protein (Cas) system-based transcriptional activator, or a combination thereof. See, e.g., Kabadi et al., *Methods* 69(2): 188-197 (September 2014), which is incorporated herein by reference in its entirety.

In some aspects, a cell described herein has been modified with a CRISPR/Cas-system-based transcriptional activator, such as CRISPR activation (CRISPRa). See, e.g., Nissim et al., *Molecular Cell* 54: 1-13 (May 2014), which is incorporated herein by reference in its entirety. CRISPRa is a type of CRISPR tool that comprises the use of modified Cas proteins that lacks endonuclease activity but retains the ability to bind to its guide RNA and the target DNA nucleic acid sequence. Non-limiting examples of such modified Cas proteins which can be used with the present disclosure are known in the art. See, e.g., Pandelakis et al., Cell Systems 10(1): 1-14 (January 2020), which is incorporated herein by reference in its entirety. In some aspects, the modified Cas protein comprises a modified Cas9 protein (also referred to in the art as "dCas9"). In some aspects, the modified Cas protein comprises a modified Cas12a protein. In some aspects, a modified Cas protein that is useful for the present disclosure is bound to a guide polynucleotide (e.g., small guide RNA) ("modified Cas-guide complex"), wherein the guide polynucleotide comprises a recognition sequence that is complementary to a region of a nucleic acid sequence encoding a protein of interest (e.g., c-Jun). In some aspects, one or more transcriptional activators are attached to the modified Cas-guide complex (e.g., the N- and/or C-terminus of the modified Cas protein), such that when the modified Cas-guide complex is introduced into a cell, the one or more transcription activators can bind to a regulatory element of a nucleic acid sequence, and thereby induce and/or increase the expression of the encoded protein (e.g., c-Jun). In some aspects, one or more transcriptional repressors (e.g., Kruppel-associated box domain (KRAB)) can be attached to the modified Cas-guide complex (e.g., the N- and/or C-terminus of the modified Cas protein), such that when introduced into a cell, the one or more transcriptional repressors can repress or reduce the transcription of a gene, e.g., such as those that can interfere with the expression of c-Jun (e.g., Bach2). See, e.g., US20200030379A1 and Yang et al., *J Transl Med* 19:459 (2021), each of which is incorporated herein by reference in its entirety. In some aspects, a modified Cas protein useful for the present disclosure can be attached to both one or more transcriptional activators and one or more transcriptional repressors.

Not to be bound by any one theory, in some aspects, the use of such modified Cas proteins can allow for the conditional transcription and expression of a gene of interest. For example, in some aspects, a cell (e.g., T cells) is modified to comprise a chimeric antigen receptor (CAR) (e.g., anti-ROR1 CAR), which is linked to a protease (e.g., tobacco etch virus (TEV)) and a single guide RNA (sgRNA) targeting the promoter region of c-Jun. In some aspects, the cell is modified to further comprise a linker for activation of T cells (LAT), complexed to the modified Cas protein attached to a transcriptional activator (e.g., dCas9-VP64-p65-Rta transcriptional activator (VPR)) via a linker (e.g., TEV-cleavable linker). Upon activation of the CAR, the modified Cas protein is released for nuclear localization and conditionally and reversibly induces the expression of c-Jun. Yang et al., *J Immunother Cancer* 9(Suppl2): A164 (2021), which is herein incorporated by reference in its entirety.

As will be apparent to those skilled in the art, in some aspects, a cell described herein has been modified using a combination of multiple approaches. For instance, in some aspects, a cell has been modified to comprise a codon-optimized c-Jun nucleotide sequence described herein, e.g., alone or in combination with one or more nucleotide sequences encoding other proteins of interest (e.g., ligand-binding protein). In some aspects, such a cell is further modified with an exogenous transcriptional activator (e.g., CRISPRa) that is capable of increasing the expression of endogenous c-Jun protein. Not to be bound by any one theory, in some aspects, such a combination approach could allow for the immune cells to have even greater level of c-Jun protein expression (e.g., both encoded by the exogenous nucleotide sequence and expressed endogenously by the immune cells).

Unless indicated otherwise, the one or more exogenous nucleotide sequences and/or transcriptional activators can be introduced into a cell using any suitable methods known in the art. Non-limiting examples of suitable methods for delivering one or more exogenous nucleotide sequences to a cell include: transfection (also known as transformation and transduction), electroporation, non-viral delivery, viral transduction, lipid nanoparticle delivery, and combinations thereof.

In some aspects, the cell is an immune cell. In some aspects, the immune cell is isolated from a human subject. In some aspects, the immune cell is a T cell. In some aspects, the T cell is a Th1 cell, Th2 cell, Th17 cell, Tc17 cell, or combinations thereof. In some aspects, the immune cell is an NK cell. In some aspects, the immune cell is a tumor infiltrating lymphocyte (TIL). In some aspects, the immune cell is a regulatory T cell (Treg). In some aspects, the immune cell is a natural killer T (NKT) cell. In some aspects, the immune cell is a B cell.

In some aspects, the cell is an immune effector cell. As used herein, term "immune effector cell" refers to a cell that is involved in an immune response, e.g., in the promotion of an immune effector response. "Immune effector function" or "immune effector response," refer to function or response, e.g., of an immune effector cell, that enhances or promotes an immune attack of a target cell. E.g., an immune effector function or response refers a property of a T or NK cell that promotes killing or the inhibition of growth or proliferation, of a target cell. In the case of a T cell, primary stimulation and co-stimulation are examples of immune effector function or response.

The term "effector function" refers to a specialized function of a cell. Effector function of a T cell, for example, may be cytolytic activity or helper activity including the secretion of cytokines. The intracellular signaling domain of a chimeric binding protein (e.g., CAR) can generate a signal that promotes an immune effector function of the chimeric binding protein containing cell, e.g., a CAR T cell. Examples of immune effector function, e.g., in a CAR T cell, include cytolytic activity and helper activity, including the secretion of cytokines. In some aspects, the intracellular signal domain is the portion of the chimeric binding protein (e.g., CAR) which transduces the effector function signal and directs the cell to perform a specialized function. While the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

In some aspects, the immune cell is differentiated from a pluripotent or multipotent progenitor cell. As such, as used herein, an "immune cell" further includes a pluripotent or multipotent cell that can give rise to a mature immune cell. In some aspects, the cell (e.g., the immune cell) is an induced pluripotent stem cell (IPSC). In some aspects, the cell (e.g., the immune cell) is an embryonic stem cell. In some aspects, the cell is a hematopoietic stem cell.

In some aspects, the T cell is a $CD4^+$ T cell. In some aspects, the T cell is a $CD8^+$ T cell. In some aspects, the T cell is a naïve T ($T_N$) cell. In some aspects, the T cell is $CD95^-/CD45RA^+/CD62L^+/CCR7^+$. In some aspects, the T cell is $CD95^+/CD45RA^+/CD62L^+/CCR7^+$. In some aspects, the T cell is $CD45RO^+/CCR7^+/CD62L^+$. In some aspects, the T cell is $CD45RO^+/CCR7^-/CD62L^-$.

As is apparent from the present disclosure, in some aspects, the cell (e.g., immune cell) with increased AP-1 expression further expresses a chimeric binding protein. In some aspects, the chimeric binding protein is a chimeric antigen receptor (CAR). Accordingly, in some aspects, a cell described herein (e.g., immune cell) has been engineered to express the AP-1 transcription factor and the CAR from a single polynucleotide (e.g., those described herein). In some aspects, a cell described herein (e.g., immune cell) has been engineered to express the AP-1 transcription factor from a first polynucleotide and the CAR from a second polynucleotide. Any CAR known in the art can be used in the cells of the present disclosure, such as those described in section 5.5.1. In certain aspects, the CAR specifically binds ROR1. In some aspects, the CAR specifically binds GPC2. In some aspects, a CAR-expressing cell is a CAR T cell, e.g., a mono CAR T cell, a genome-edited CAR T cell, a dual CAR T cell, or a tandem CAR T cell. Examples of such CAR T cells are provided in International Application No. PCT/US2019/044195 (corresponding to US20210299223A1), which is incorporated herein by reference in its entirety.

In some aspects, the chimeric binding protein comprises a TCR (e.g., engineered TCR). In some aspects, a cell described herein (e.g., immune cell) has been engineered to express the AP-1 transcription factor and the TCR from a single polynucleotide (e.g., those described herein). In some aspects, a cell described herein (e.g., immune cell) has been engineered to express the AP-1 transcription factor from a first polynucleotide and the TCR from a second polynucleotide. Any TCR known in the art can be used in the cells of the present disclosure, such as those described in Section 5.4.1.

In some aspects, the chimeric binding protein comprises a chimeric antibody-T cell receptor (CaTCR). In some aspects, a cell described herein (e.g., immune cell) has been engineered to express the AP-1 transcription factor and the caTCR from a single polynucleotide (e.g., those described herein). In some aspects, a cell described herein (e.g., immune cell) has been engineered to express the AP-1 transcription factor from a first polynucleotide and the caTCR from a second polynucleotide. Any caTCR known in the art can be used in the cells of the present disclosure, such as those described in Section 5.4.1.

In some aspects, the chimeric binding protein comprises a chimeric signaling receptor (CSR). In some aspects, a cell described herein (e.g., immune cell) has been engineered to express the AP-1 transcription factor and the CSR from a single polynucleotide (e.g., those described herein). In some aspects, a cell described herein (e.g., immune cell) has been engineered to express the AP-1 transcription factor from a first polynucleotide and the CSR from a second polynucleotide. Any CSR known in the art can be used in the cells of the present disclosure, such as those described in Section 5.4.1.

In some aspects, the chimeric binding protein comprises a TCR mimic. In some aspects, a cell described herein (e.g., immune cell) has been engineered to express the AP-1 transcription factor and the TCR mimic from a single polynucleotide (e.g., those described herein). In some aspects, a cell described herein (e.g., immune cell) has been engineered to express the AP-1 transcription factor from a first polynucleotide and the TCR mimic from a second polynucleotide. Any TCR mimic known in the art can be used in the cells of the present disclosure, such as those described in Section 5.4.1.

In some aspects, a cell described herein (e.g., expressing AP-1 transcription factor and a chimeric binding protein) can be modified to additionally express one or more proteins encoded by the additional translational sequences described herein (see, e.g., Section 5.4).

Certain aspects of the present disclosure are directed to methods of making a chimeric binding protein disclosed herein by transfecting a cell, e.g., an immune cell, with a polynucleotide (e.g., polycistronic polynucleotide comprising a codon-optimized AP-1 nucleotide sequence and a nucleotide sequence encoding a chimeric binding protein) disclosed herein and culturing the cell under suitable conditions.

Compositions

In some aspects, the present disclosure further comprises a composition comprising any of the polynucleotides, vectors, cells, polypeptides, or set of polypeptides described herein. In certain aspects, the composition comprises a T cell which has been engineered to express a protein encoded by a polynucleotide described herein, such as a chimeric binding protein (e.g., CAR) and an AP-1 transcription factor (e.g., CAR T cell, e.g., anti-ROR1 CAR T cell). In some aspects, the composition is a pharmaceutical composition. Accordingly, disclosed herein are pharmaceutical compositions comprising (i) a cell (e.g., immune cell) that has been modified to express an AP-1 transcription factor, e.g., wherein the expression of the AP-1 transcription factor is increased compared to the expression in a corresponding cell that was not transduced with a polynucleotide comprising a codon-optimized AP-1 nucleotide sequence, and (ii) a pharmaceutically acceptable carrier. In some aspects, provided herein are pharmaceutical compositions comprising (i) a cell (e.g., immune cell) that has been modified to express an AP-1 transcription factor and a chimeric binding protein (e.g., CAR), e.g., wherein the expression of the AP-1 transcription factor is increased compared to the expression in a corresponding cell that was not transduced with a polynucleotide comprising a codon-optimized AP-1 nucleotide sequence, and (ii) a pharmaceutically acceptable carrier. As described herein, such pharmaceutical compositions can be used to prevent and/or treat a disease or disorder (e.g., cancer). In some aspects, the cell present in a pharmaceutical composition disclosed herein is a T cell or an NK cell.

As used herein, the term "pharmaceutical composition" refers to one or more of the compounds described herein, such as, e.g., an engineered T cell comprising a chimeric binding protein (e.g., CAR) and overexpressing an AP-1 transcription factor, mixed or intermingled with, or suspended in one or more other chemical components, such as pharmaceutically-acceptable carriers and excipients. Not to be bound by any one theory, in some aspects, a purpose of a pharmaceutical composition is to facilitate administration of preparations of, e.g., cell expressing an AP-1 transcription factor and a chimeric binding protein (e.g., CAR) of the present disclosure to a subject.

The terms "excipient" and "carrier" are used interchangeably and refer to an inert substance added to a pharmaceutical composition to further facilitate administration of a compound, e.g., any of the polynucleotides, vectors, cells, polypeptides, or set of polypeptides described herein.

The terms "pharmaceutically-acceptable carrier," "pharmaceutically-acceptable excipient," and grammatical variations thereof, encompass any of the agents approved by a regulatory agency of the U.S. Federal government or listed in the U.S. Pharmacopeia for use in animals, including humans, as well as any carrier or diluent that does not cause the production of undesirable physiological effects to a degree that prohibits administration of the composition to a subject and does not abrogate the biological activity and properties of the administered compound. Included are excipients and carriers that are useful in preparing a pharmaceutical composition and are generally safe, non-toxic, and desirable.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS® or polyethylene glycol (PEG).

A pharmaceutical composition can be formulated for any route of administration to a subject. Specific examples of routes of administration include intramuscularly, subcutaneously, ophthalmic, intravenously, intraperitoneally, intradermally, intraorbitally, intracerebrally, intracranially, intraspinally, intraventricularly, intrathecally, intracisternally, intracapsularly, or intratumorally. Parenteral administration, characterized by either subcutaneous, intramuscular or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, or glycerol. In addition, if desired, the pharmaceutical compositions to be administered can also contain minor amounts of non-toxic auxiliary substances s, pH buffering agents, stabilizers, and other such agents, such as for example, sodium acetate, sorbitan monolaurate, triethanolamine oleate, and cyclodextrins.

If administered intravenously, suitable carriers include physiological saline or phosphate buffered saline (PBS), and solutions containing thickening and solubilizing agents, such as glucose, polyethylene glycol, and polypropylene glycol and mixtures thereof.

The compositions (e.g., engineered T cell comprising a chimeric binding protein and overexpressing an AP-1 transcription factor) to be used for in vivo administration can be sterile. This can be accomplished by filtration through, e.g., sterile filtration membranes.

Kits

Also disclosed herein are kits comprising any of the polynucleotides, vectors, compositions, cells (e.g., CAR T cells overexpressing an AP-1 transcription factor), polypeptides, or set of polypeptides described herein. In some aspects, the kit is for use in immunotherapy against a disease or disorder (e.g., cancer) and/or treating or reducing the rick for the disease or disorder (e.g., cancer). In certain aspects, the kit includes one or more containers comprising any of the polynucleotides, vectors, compositions, polypeptides, or set of polypeptides described herein.

In some aspects, the kit comprises instructions for use in accordance with any of the methods described herein. For example, the included instructions can comprise a description of administration of the pharmaceutical composition described herein to treat, delay the onset, or alleviate a target disease. In some aspects, the instructions comprise a description of administering the composition described herein to a subject at risk of the target disease/disorder (e.g., cancer).

In some aspects, the instructions comprise dosage information, dosing schedule, and route of administration. In some aspects, the containers are unit doses, bulk packages (e.g., multi-dose packages) or sub-unit doses. In some aspects, the instructions are written instructions on a label or package insert (e.g., a paper sheet included in the kit). In some aspects, the instructions are machine-readable instructions (e.g., instructions carried on a magnetic or optical storage disk).

In some aspects, the label or package insert indicates that the composition disclosed herein is used for treating, delaying the onset, and/or alleviating a disease or disorder associated with cancer, such as those described herein. Instructions can be provided for practicing any of the methods described herein.

In some aspects, the kits described herein are in suitable packaging. In some aspects, suitable packing comprises vials, bottles, jars, flexible packaging (e.g., seal Mylar or plastic bags), or combinations thereof. In some aspects, the packaging comprises packages for use in combination with a specific device such as an inhaler, nasal administration device (e.g., an atomizer), or an infusion device such as a minipump. In some aspects, the kit comprises a sterile access port (for example the container can be an intravenous solution bag or a vial having a stopper pierceable by a hypodermic injection needle). In some aspects, the container can also have a sterile access port (for example the container can be an intravenous solution bag or a vial having a stopper pierceable by a hypodermic injection needle). In some aspects, at least one active agent is a composition as described herein (e.g., an engineered T cell comprising a chimeric binding protein and overexpressing an AP-1 transcription factor).

In some aspects, the kits further comprise additional components such as buffers and interpretive information. In some aspects, the kit comprises a container and a label or package insert(s) on or associated with the container. In some aspects, the disclosure provides articles of manufacture comprising the contents of the kits described herein.

Therapeutic Uses

Certain aspects of the present disclosure are directed to methods of administering any of the polynucleotides, vectors, compositions, cells polypeptides, or set of polypeptides described herein (e.g., an AP-1 transcription factor and a chimeric binding protein). Certain aspects of the present disclosure are directed to methods of treating a disease or disorder in a subject in need thereof, comprising administering to the subject any of the polynucleotides, vectors, compositions, cells polypeptides, or set of polypeptides described herein (e.g., an AP-1 transcription factor and a chimeric binding protein). For instance, in certain aspects, disclosed herein is a method of treating a disease or disorder in a subject in need thereof, comprising administering to the subject a cell that has been engineered to express a chimeric binding protein (e.g., CAR) and overexpress an AP-1 transcription factor. In some aspects, the disease or condition comprises a tumor, i.e., a cancer. In some aspects, the method comprises stimulating a T cell-mediated immune response to a target cell population or tissue in a subject, comprising administering an effective amount of any of the polynucleotides, vectors, compositions, cells polypeptides, or set of polypeptides described herein (e.g., an engineered cell comprising a chimeric binding protein and overexpressing an AP-1 transcription factor). In some aspects, the target cell population comprises a tumor. In some aspects, the tumor is a solid tumor.

In some aspects, administering any of the polynucleotides, vectors, compositions, cells, polypeptides, or set of polypeptides described herein (e.g., an engineered cell comprising a chimeric binding protein and overexpressing an AP-1 transcription factor) reduces a tumor volume in the subject compared to a reference tumor volume. In some aspects, the reference tumor volume is the tumor volume in the subject prior to the administration. In further aspects, the reference tumor volume is the tumor volume in a corresponding subject that did not receive the administration. In some aspects, the tumor volume in the subject is reduced by at least about 5%, at least about 10%, at least about 15%, at least about 30%, at least about 40%, at least about 50%, at least about 60%, at least about 70%, at least about 80%, at least about 90%, or at least about 100% after the administration compared to the reference tumor volume.

In some aspects, treating a tumor comprises reducing a tumor weight in the subject. In certain aspects, administering any of the polynucleotides, vectors, compositions, cells, polypeptides, or set of polypeptides described herein (e.g., an engineered cell comprising a chimeric binding protein and overexpressing an AP-1 transcription factor) can reduce the tumor weight in a subject when administered to the subject. In some aspects, the tumor weight is reduced by at least about 5%, at least about 10%, at least about 15%, at least about 30%, at least about 40%, at least about 50%, at least about 60%, at least about 70%, at least about 80%, at least about 90%, or at least about 100% after the administration compared to a reference tumor weight. In some aspects, the reference tumor weight is the tumor weight in the subject prior to the administration. In further aspects, the reference tumor weight is the tumor weight in a corresponding subject that did not receive the administration.

In some aspects, administering any of the polynucleotides, vectors, compositions, cells, polypeptides, or set of polypeptides described herein (e.g., an engineered cell comprising a chimeric binding protein and overexpressing an AP-1 transcription factor) to a subject, e.g., suffering from a tumor, can increase the number and/or percentage of TILs (e.g., $CD4^+$ or $CD8^+$) in a tumor and/or a tumor microenvironment (TME) of the subject. In certain aspects, the number and/or percentage of TILs in a tumor and/or TME is increased by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, or at least about 300% or more compared to a reference (e.g., corresponding value in a subject that did not receive the administration or the same subject prior to the administration).

In some aspects, administering any of the polynucleotides, vectors, compositions, cells, polypeptides, or set of polypeptides described herein (e.g., an engineered cell comprising a chimeric binding protein and overexpressing an AP-1 transcription factor) to a subject, e.g., suffering from a tumor, can increase the duration of an immune response in a subject relative to the duration of an immune response in a corresponding subject that did not receive the administration (e.g., treated with a corresponding cell but lacking AP-1 transcription factor expression). In certain aspects, the duration of the immune response is increased by at least about 5%, at least about 10%, at least about 20%, at least about 30%, at least about 40%, at least about 50%, at least about 75%, at least about 100%, at least about 150%, at least about 200%, at least about 300%, at least about 400%, at least about 500%, or at least about 1000% or more compared to a reference (e.g., corresponding subject that did not receive the administration). In certain aspects, the duration of the immune response is increased by at least about 2-fold, at least about 3-fold, at least about 4-fold, at least about 5-fold, at least about 6-fold, at least about 7-fold, at least about 8-fold, at least about 9-fold, or at least about 10-fold or more compared to a reference (e.g., corresponding subject that did not receive the administration).

As described herein, any of the polynucleotides, vectors, compositions, cells, polypeptides, or set of polypeptides described herein (e.g., an engineered cell comprising a chimeric binding protein and overexpressing an AP-1 transcription factor) can be used to treat variety of cancers. Non-limiting examples of cancers that can be treated include adrenal cortical cancer, advanced cancer, anal cancer, aplastic anemia, bile duct cancer, bladder cancer, bone cancer, bone metastasis, brain tumors, brain cancer, breast cancer, childhood cancer, cancer of unknown primary origin, Castleman disease, cervical cancer, colon/rectal cancer, endometrial cancer, esophagus cancer, Ewing family of tumors, eye cancer, gallbladder cancer, gastrointestinal carcinoid tumors, gastrointestinal stromal tumors, gestational trophoblastic disease, Hodgkin disease, Kaposi sarcoma, renal cell carcinoma, laryngeal and hypopharyngeal cancer, acute lymphocytic leukemia, acute myeloid leukemia, chronic lymphocytic leukemia, chronic myeloid leukemia, chronic myelomonocytic leukemia, liver cancer, non-small cell lung cancer, small cell lung cancer, lung carcinoid tumor, lymphoma of the skin, malignant mesothelioma, multiple myeloma, myelodysplastic syndrome, nasal cavity and paranasal sinus cancer, nasopharyngeal cancer, neuroblastoma, non-Hodgkin lymphoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma in adult soft tissue, basal and squamous cell skin cancer, melanoma, small intestine cancer, stomach cancer, testicular cancer, throat cancer, thymus cancer, thyroid cancer, uterine sarcoma, vaginal cancer, vulvar cancer, Waldenstrom macroglobulinemia, Wilms tumor, secondary cancers caused by cancer treatment, and combinations thereof. In some aspects, the cancer is associated with a solid tumor.

In some aspects, any of the polynucleotides, vectors, compositions, cells, polypeptides, or set of polypeptides described herein (e.g., an engineered cell comprising a chimeric binding protein and overexpressing an AP-1 transcription factor) is used in combination with other therapeutic agents (e.g., anti-cancer agents and/or immunomodulating agents). Accordingly, in certain aspects, a method of treating a disease or disorder (e.g., tumor) disclosed herein comprises administering any of the polynucleotides, vectors, compositions, cells, polypeptides, or set of polypeptides described herein (e.g., an engineered cell comprising a chimeric binding protein and overexpressing an AP-1 transcription factor) in combination with one or more additional therapeutic agents. Such agents can include, for example, chemotherapeutic drug, targeted anti-cancer therapy, oncolytic drug, cytotoxic agent, immune-based therapy, cytokine, surgery, radiotherapy, activator of a costimulatory molecule, immune checkpoint inhibitor, a vaccine, a cellular immunotherapy, or any combination thereof.

In some aspects, any of the polynucleotides, vectors, compositions, cells, polypeptides, or set of polypeptides described herein (e.g., an engineered cell comprising a chimeric binding protein and overexpressing an AP-1 transcription factor) is administered to the subject prior to or after the administration of the additional therapeutic agent. In other aspects, any of the polynucleotides, vectors, compositions, cells, polypeptides, or set of polypeptides described herein (e.g., an engineered cell comprising a chimeric binding protein and overexpressing an AP-1 transcription factor) is administered to the subject concurrently with the additional therapeutic agent. In certain aspects, any of the polynucleotides, vectors, compositions, cells, polypeptides, or set of polypeptides described herein (e.g., an engineered cell comprising a chimeric binding protein and overexpressing an AP-1 transcription factor) and the additional therapeutic agent can be administered concurrently as a single composition in a pharmaceutically acceptable carrier. In other aspects, any of the polynucleotides, vectors, compositions, cells, polypeptides, or set of polypeptides described herein (e.g., an engineered cell comprising a chimeric binding protein and overexpressing an AP-1 transcription factor) and the additional therapeutic agent are administered concurrently as separate compositions.

In some aspects, any of the polynucleotides, vectors, compositions, cells, polypeptides, or set of polypeptides described herein (e.g., an engineered cell comprising a chimeric binding protein and overexpressing an AP-1 transcription factor) is used in combination with a standard of care treatment (e.g., surgery, radiation, and chemotherapy). Methods described herein can also be used as a maintenance therapy, e.g., a therapy that is intended to prevent the occurrence or recurrence of tumors.

In some aspects, any of the polynucleotides, vectors, compositions, cells, polypeptides, or set of polypeptides described herein (e.g., an engineered cell comprising a chimeric binding protein and overexpressing an AP-1 transcription factor) is used in combination with one or more anti-cancer agents, such that multiple elements of the immune pathway can be targeted. Non-limiting examples of such combinations include: a therapy that enhances tumor antigen presentation (e.g., dendritic cell vaccine, GM-CSF secreting cellular vaccines, CpG oligonucleotides, imiquimod); a therapy that inhibits negative immune regulation e.g., by inhibiting CTLA-4 and/or PD1/PD-L1/PD-L2 pathway and/or depleting or blocking Tregs or other immune suppressing cells (e.g., myeloid-derived suppressor cells); a therapy that stimulates positive immune regulation, e.g., with agonists that stimulate the CD-137, OX-40, and/or CD40 or GITR pathway and/or stimulate T cell effector function; a therapy that increases systemically the frequency of anti-tumor T cells; a therapy that depletes or inhibits Tregs, such as Tregs in the tumor, e.g., using an antagonist of CD25 (e.g., daclizumab) or by ex vivo anti-CD25 bead depletion; a therapy that impacts the function of suppressor myeloid cells in the tumor; a therapy that enhances immunogenicity of tumor cells (e.g., anthracyclines); adoptive T cell or NK cell transfer including genetically engineered cells, e.g., cells engineered to express a chimeric antigen receptor (CAR-T therapy); a therapy that inhibits a metabolic enzyme such as indoleamine dioxigenase (IDO), dioxigenase, arginase, or nitric oxide synthetase; a therapy that reverses/prevents T cell anergy or exhaustion; a therapy that triggers an innate immune activation and/or inflammation at a tumor site; administration of immune stimulatory cytokines; blocking of immuno repressive cytokines; or any combination thereof.

In some aspects, an anti-cancer agent comprises an immune checkpoint inhibitor (i.e., blocks signaling through the particular immune checkpoint pathway). Non-limiting examples of immune checkpoint inhibitors that can be used in the present methods comprise a CTLA-4 antagonist (e.g., anti-CTLA-4 antibody), PD-1 antagonist (e.g., anti-PD-1 antibody, anti-PD-L1 antibody), TIM-3 antagonist (e.g., anti-TIM-3 antibody), or combinations thereof. Non-limiting examples of such immune checkpoint inhibitors include the following: anti-PD1 antibody (e.g., nivolumab (OPDIVO®), pembrolizumab (KEYTRUDA®; MK-3475), pidilizumab (CT-011), PDR001, MEDI0680 (AMP-514), TSR-042, REGN2810, JS001, AMP-224 (GSK-2661380), PF-06801591, BGB-A317, BI 754091, SHR-1210, and combinations thereof); anti-PD-L1 antibody (e.g., atezolizumab (TECENTRIQ®; RG7446; MPDL3280A; RO5541267), durvalumab (MEDI4736, IMFINZI®), BMS-936559, avelumab)(BAVENCIO®), LY3300054, CX-072 (Proclaim-CX-072), FAZ053, KN035, MDX-1105, and combinations thereof); and anti-CTLA-4 antibody (e.g., ipilimumab)(YERVOY®), tremelimumab (ticilimumab; CP-675,206), AGEN-1884, ATOR-1015, and combinations thereof).

In some aspects, an anti-cancer agent comprises an immune checkpoint activator (i.e., promotes signaling through the particular immune checkpoint pathway). In certain aspects, immune checkpoint activator comprises OX40 agonist (e.g., anti-OX40 antibody), LAG-3 agonist (e.g. anti-LAG-3 antibody), 4-1BB (CD137) agonist (e.g., anti-CD137 antibody), GITR agonist (e.g., anti-GITR antibody), TIM3 agonist (e.g., anti-TIM3 antibody), or combinations thereof.

The practice of the present disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986);); Crooks, Antisense drug Technology: Principles, strategies and applications, 2$^{nd}$ Ed. CRC Press (2007) and in Ausubel et al. (1989) Current Protocols in Molecular Biology (John Wiley and Sons, Baltimore, Md.).

All of the references cited above, as well as all references cited herein and the amino acid or nucleotide sequences (e.g., GenBank numbers and/or Uniprot numbers), are incorporated herein by reference in their entireties.

The following examples are offered by way of illustration and not by way of limitation.

EXAMPLES

Example 1—Generation of Constructs with Codon-Optimized c-Jun Sequences

To increase transgene expression, R12-EGFRt constructs (i.e., comprising anti-ROR1 scFv+truncated EGFR) comprising codon-optimized c-Jun sequences were generated using different optimization approaches. The codon-optimized c-Jun sequences are provided in SEQ ID Nos:1-10. As control, a bicistronic R12-EGFRt construct lacking a c-Jun sequence was used (construct #1 in FIG. 1). As an additional control, a tricistonic R12-EGFRt construct comprising truncated CD19 (CD19t) instead of c-Jun was also used (construct #2 in FIG. 1). In SEQ ID NO: 1, codon optimization was tailored to mimic codon usage bias in human cells (construct #3 in FIG. 1) and in SEQ ID NO: 2 codon optimization usage was tailored to mimic codon usage bias in human T cells (construct #4 in FIG. 1).

To assess whether the codon-optimized c-Jun can improve the expression of c-Jun in an anti-ROR1 construct, a set of the anti-ROR1 constructs shown in FIG. 1 were used to transduce T cells at different multiplicities of infection (MOI 2, 5, 10, and 20). Then, the expression levels of c-Jun and R12 CAR and EGFRt of the different constructs was determined using flow cytometry.

Figure 2A:
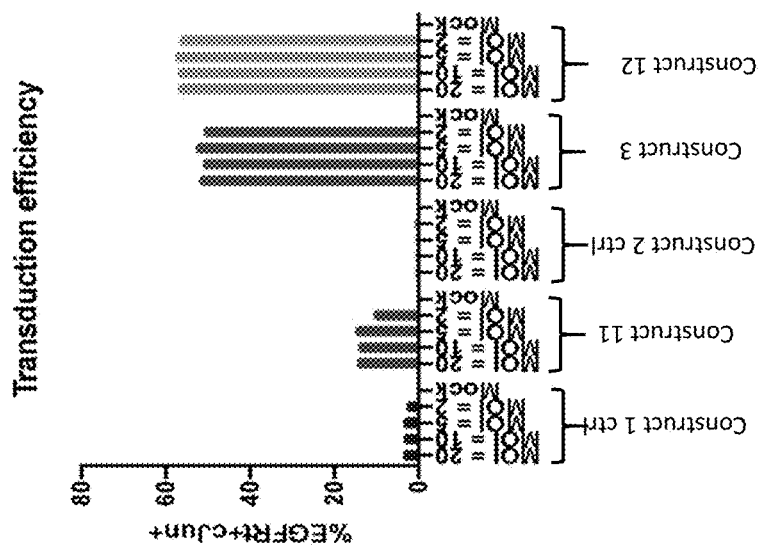
FIGS. 2A, 2B, 2C, and 2D show the transduction efficiency and transgene expression levels of the various anti-ROR1 constructs.
Figure 2B:
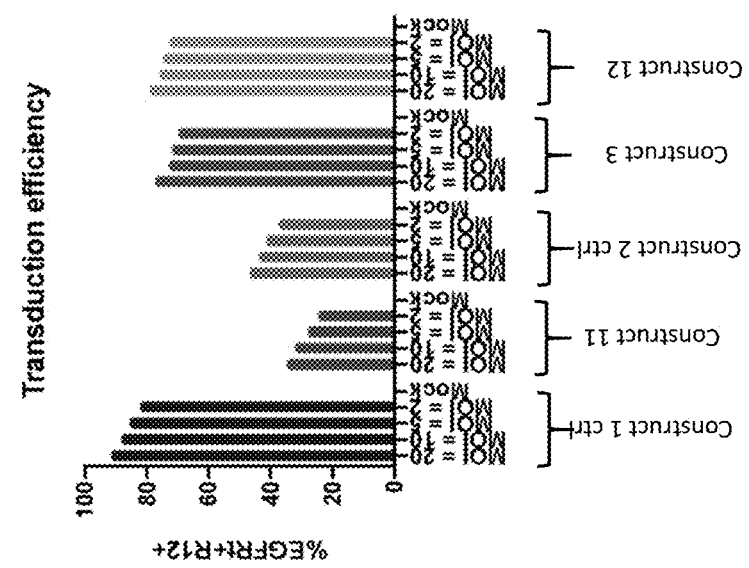

As shown in FIG. 2A, the anti-ROR1 Constructs 3 and 12 containing the c-Jun codon optimized sequences provided in SEQ ID NOs: 1 and 10, respectively, demonstrated the highest percentage of EGFRt$^+$c-Jun$^+$ cells compared to control anti-ROR1 constructs (i.e., R12-EGFRt and CD19t-R12-EGFRt). As expected, cells transduced with anti-ROR1 constructs lacking c-Jun (i.e., R12-EGFRt and CD19t-R12-EGFRt) had negligible percentage of cells expressing both EGFRt and c-Jun. When the transduced cells were analyzed for the expression of both EGFRt and anti-ROR1 scFv (R12), there was much higher percentage of EGFRt+R12+ cells when the cells were transduced with the constructs 3 and 12 codon-optimized c-Jun anti-ROR1 constructs as compared to the anti-ROR1 construct comprising the construct 11 containing the codon optimized c-Jun sequence of SEQ ID NO: 9 (FIG. 2B) and the control CD19t-R12-EGFRt construct.

Figure 2C:
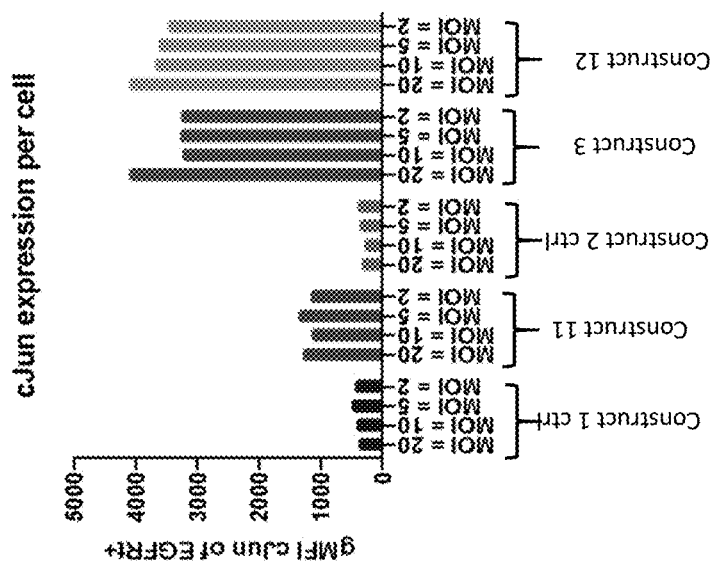
Figure 2D:
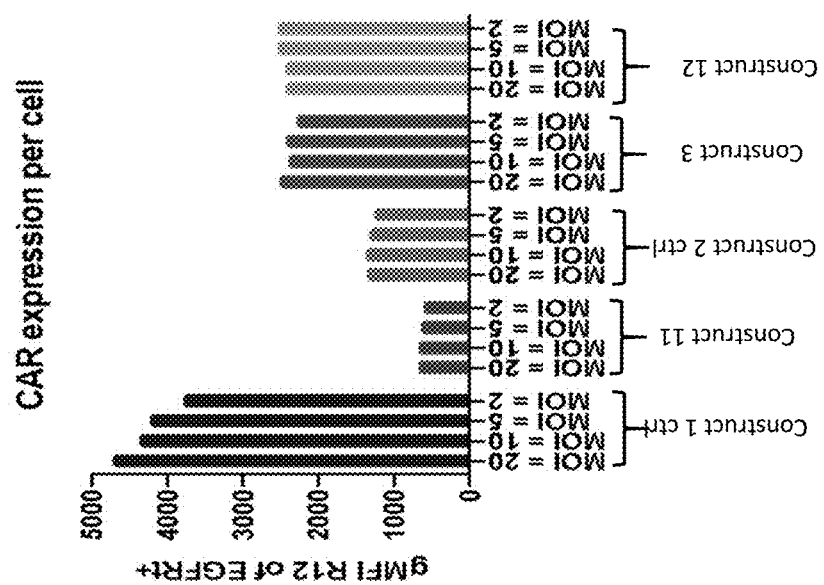

On a single cell level, c-Jun expression was also substantially higher in cells transduced with Construct 3 and Construct 12 codon-optimized c-Jun-anti-ROR1 constructs as compared to the anti-ROR1 construct comprising the Construct 11 codon optimized c-Jun sequence of SEQ ID NO: 9 (FIG. 2C). Further, anti-ROR1 CAR expression was also higher on a single cell level in cells transduced with Construct 3 and Construct 12 codon-optimized c-Jun-anti-ROR1 constructs as compared to the anti-ROR1 construct comprising the Construct 11 codon optimized c-Jun sequence of SEQ ID NO: 9 (FIG. 2D) and the control CD19t-R12-EGFRt construct.

These results demonstrated that inclusion of the codon optimized c-Jun sequence of SEQ ID NOs: 1 and 10 contained in the Constructs 3 and 12 anti ROR1-EGFRt constructs could substantially increase c-Jun transgene expression in target cells. The overall transduction efficiency was similar to that of the R12-EGFRt construct (i.e., lacking c-Jun) and the codon-optimized c-Jun-anti-ROR1 CAR constructs were not associated with high vector copy number (data not shown).

In another experiment, additional codon-optimized c-Jun sequences described above were used to transduce T cells at various multiplicities of infection and the expression levels of the transgenes of the different constructs was determined using flow cytometry. For each of the constructs, MOIs lending similar levels of transduction, measured by co-expression of anti-ROR1 CAR and EGFRt, were selected for comparison of transgene expression by T cells.

Figure 3A:
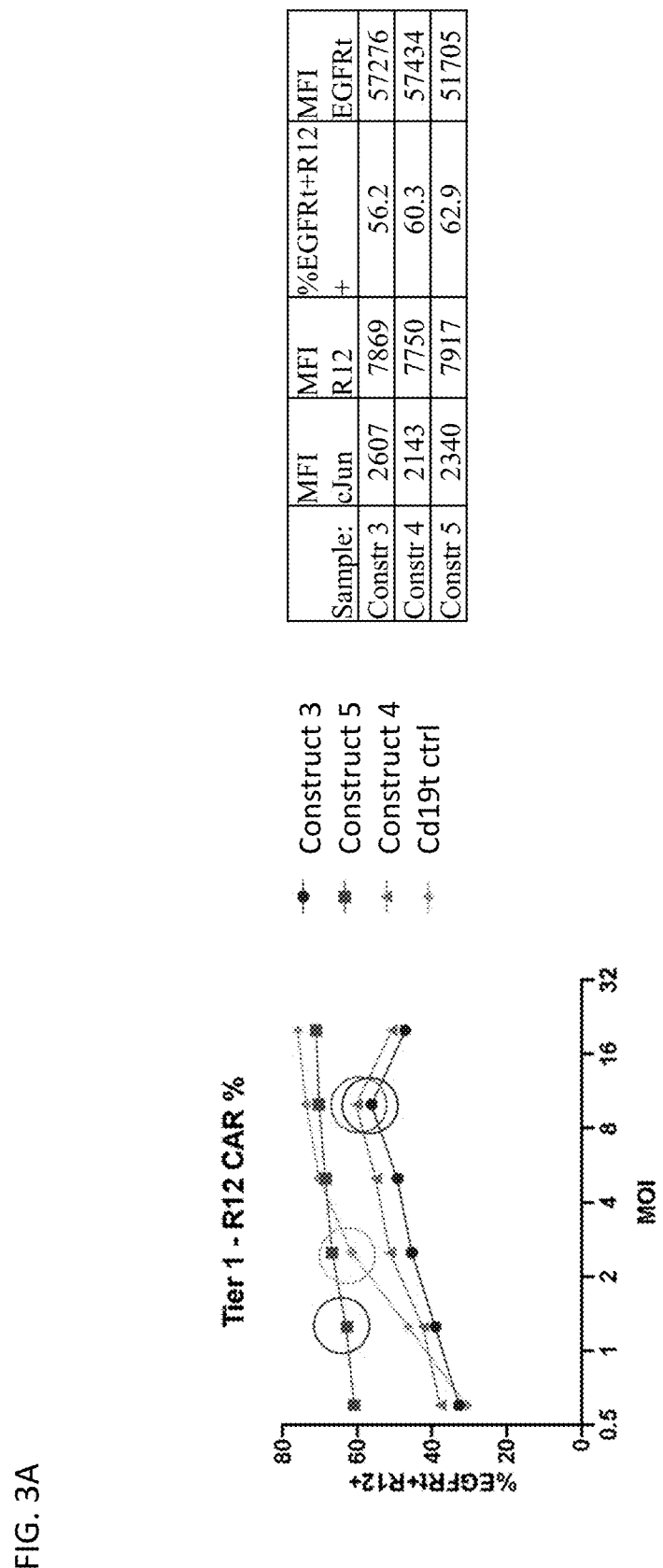
FIG. 3A shows the transduction efficiency and 3B shows the transgene expression level of the anti-ROR1 CAR constructs comprising different codon-optimized c-Jun sequences. The transduction efficiency is shown as the percentage of cells that are EGFRt$^+$R12CAR$^+$ (y-axis) at different MOIs (x-axis).
Figure 3B:
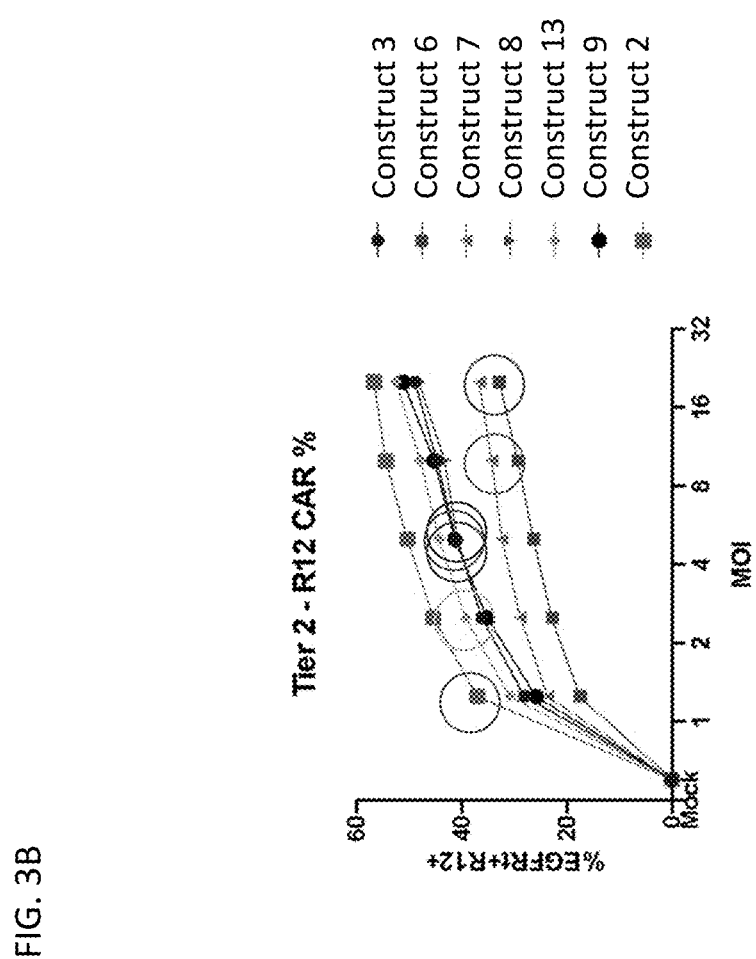
In FIG. 3B, results for the following anti-ROR1 CAR constructs are shown: (i) Construct #3 (i.e., comprising the codon-optimized c-Jun sequence set forth in SEQ ID NO: 1) (small circle); (ii) Construct #6 (i.e., comprising the codon-optimized c-Jun sequence set forth in SEQ ID NO: 4) (small square); (iii) Construct #7 (i.e., comprising the codon-optimized c-Jun sequence set forth in SEQ ID NO: 5) (triangle); (iv) Construct #8 (i.e., comprising the codon-optimized c-Jun sequence set forth in SEQ ID NO: 6) (inverted triangle); (v) Construct #13 (i.e., comprising the wild-type c-Jun sequence) (diamond); (vi) Construct #9 (i.e., comprising the codon-optimized c-Jun sequence set forth in SEQ ID NO: 7) (large circle); and (vii) Construct #2 (i.e., lacking c-Jun and comprising truncated CD19) (large square). The circled data points in each of FIGS. 3A and 3B represent titers used for a comparison between the various constructs as shown in the tables to the right of the graphs.

A first experiment was carried out (Tier 1; FIG. 3A). In this experiment, Construct 3 was shown to have the highest c-Jun expression while maintaining good expression of the anti-ROR1 CAR and EGFRt transgenes with only a slight reduction in transduction efficiency as compared to Construct 5, which also showed slightly lower but still good c-Jun expression, and the CD19t control. Construct 3 was selected and then compared to additional codon optimized c-Jun constructs in the Tier 2 experiment as shown in FIG. 3B. In the Tier 2 comparison, Constructs 3 and 8 showed high c-Jun expression while maintaining good expression of the anti-ROR1 CAR and EGFRt transgenes, with Construct 3 having the highest c-Jun expression. Construct 7 also showed good c-Jun expression but showed lower transduction efficiency, and ROR1 CAR and EGFRt expression.

In summary, numerous codon-optimized c-Jun sequences were generated and screened for their effect on transduction efficiency and c-Jun, R12 and EGFRt transgene expression. These experiments showed that Constructs 3, 8 and 12 (having codon optimized c-Jun sequences as shown in SEQ ID NOs: 1, 6 and 10, respectively) had high c-Jun expression with acceptable impact on transduction efficiency and transgene (R12 and EGFRt) expression. Construct 7 also had good c-Jun and R12 expression and a modest reduction in transduction efficiency and EGFRt expression. These candidate codon-optimized c-Jun sequences can be used, in particular, for reducing exhaustion in engineered immune cells for adoptive cell immunotherapy.

What is claimed is:

1. A polynucleotide comprising
a nucleotide sequence having at least 89% sequence identity to the nucleic acid sequence set forth in SEQ ID NO: 1;
wherein the nucleotide sequence encodes a c-Jun protein, and wherein the c-Jun protein comprises the amino acid sequence set forth in SEQ ID NO: 13.

2. The polynucleotide of claim 1, wherein the nucleotide sequence comprises the nucleic acid sequence set forth in SEQ ID NO: 1.

3. The polynucleotide of claim 1, further comprising a nucleotide sequence encoding a ligand binding protein.

4. The polynucleotide of claim 3, wherein the ligand binding protein comprises a chimeric antigen receptor (CAR), a T cell receptor (TCR), a chimeric antibody-T cell receptor (caTCR), a chimeric signaling receptor (CSR), T cell receptor mimic (TCR mimic), or combinations thereof.

5. The polynucleotide of claim 3, wherein the ligand binding protein comprises an antigen-binding domain, a transmembrane domain, a costimulatory domain, an intracellular signaling domain, or a combination thereof.

6. The polynucleotide of claim 4, wherein the TCR specifically binds a tumor antigen/MHC complex.

7. The polynucleotide of claim 1, further comprising a nucleic acid sequence encoding a truncated EGFR (EGFRt).

8. A vector comprising the polynucleotide of claim 1 and a regulatory element.

9. A composition comprising the polynucleotide of claim 1.

10. A kit comprising the polynucleotide of claim 1.

11. A vector comprising the polynucleotide of claim 2 and a regulatory element.

12. A vector comprising the polynucleotide of claim 3 and a regulatory element.

13. A vector comprising the polynucleotide of claim 7 and a regulatory element.

14. A composition comprising the polynucleotide of claim 2.

15. A composition comprising the polynucleotide of claim 3.

16. A composition comprising the polynucleotide of claim 7.

17. The composition of claim 9, which further comprises a carrier.

18. The composition of claim 14, which further comprises a carrier.

19. The composition of claim 15, which further comprises a carrier.

20. The composition of claim 16, which further comprises a carrier.

* * * * *